United States Patent
John et al.

(10) Patent No.: US 11,229,788 B1
(45) Date of Patent: Jan. 25, 2022

(54) SYSTEMS FOR IMPROVING NEUROSTIMULATION COMPLIANCE USING A PATIENT INTERFACE MODULE

(71) Applicant: EBT MEDICAL INC., Toronto (CA)

(72) Inventors: Michael Sasha John, Larchmont, NY (US); Paul B. Yoo, Toronto (CA)

(73) Assignee: EBT Medical, Inc., Toronto (CA)

( * ) Notice: Subject to any disclaimer, the term of this patent is extended or adjusted under 35 U.S.C. 154(b) by 0 days.

(21) Appl. No.: 17/249,775

(22) Filed: Mar. 12, 2021

Related U.S. Application Data

(63) Continuation of application No. 16/228,204, filed on Dec. 20, 2018, now Pat. No. 10,946,194, which is a continuation-in-part of application No. 15/678,824, filed on Aug. 16, 2017, now Pat. No. 10,556,107, which is a continuation-in-part of application No. 15/439,415, filed on Feb. 22, 2017, now Pat. No. 9,884,187, which is a continuation of application No. 15/160,468, filed on May 20, 2016, now Pat. No. 9,610,442, said application No. 15/678,824 is a continuation-in-part of application No. 15/160,585, filed on May 20, 2016, now abandoned, which is a continuation-in-part of application No. 14/553,427, filed on Nov. 25, 2014, now Pat. No. 10,549,087.

(60) Provisional application No. 62/608,540, filed on Dec. 20, 2017, provisional application No. 62/375,898, filed on Aug. 16, 2016, provisional application No. 62/171,549, filed on Jun. 5, 2015, provisional application No. 62/165,037, filed on May 21, 2015, (Continued)

(51) Int. Cl.
*A61N 1/36* (2006.01)
*A61N 2/02* (2006.01)
*A61N 2/00* (2006.01)
*A61N 1/05* (2006.01)
*A61N 1/04* (2006.01)

(52) U.S. Cl.
CPC ....... *A61N 1/36007* (2013.01); *A61N 1/0456* (2013.01); *A61N 1/0502* (2013.01); *A61N 1/0553* (2013.01); *A61N 1/0556* (2013.01); *A61N 1/3603* (2017.08); *A61N 1/3606* (2013.01); *A61N 1/36017* (2013.01); *A61N 1/36107* (2013.01); *A61N 2/006* (2013.01); *A61N 2/02* (2013.01); *A61N 1/36034* (2017.08)

(58) Field of Classification Search
CPC .. A61N 1/36007; A61N 2/006; A61N 1/0556; A61N 2/02; A61N 1/0553
USPC .......................................................... 607/41
See application file for complete search history.

(56) References Cited

U.S. PATENT DOCUMENTS

2003/0074037 A1\* 4/2003 Moore ............... A61N 1/36021
607/63
2008/0319272 A1\* 12/2008 Patangay ................. A61B 5/74
600/300

\* cited by examiner

*Primary Examiner* — Amanda K Hulbert
*Assistant Examiner* — Philip C Edwards
(74) *Attorney, Agent, or Firm* — Rosenberg, Klein & Lee

(57) ABSTRACT

Nerve stimulation systems and methods are disclosed for providing improved compliance of a patient to a pelvic disorder treatment regimen. A patient interface module is connected to a control module for providing compliance information related to compliance criteria for a set of scheduled events. Patient compliance is assessed and notification or treatment events can be scheduled, rescheduled or otherwise adjusted based upon patient compliance or noncompliance according to compliance rules and parameters of a treatment compliance module. Both compliance and noncompliance may lead to adjustment of the treatment regi- (Continued)

men, scheduled treatment events, and notifications to the patient or user operating the nerve stimulation system.

27 Claims, 19 Drawing Sheets

Related U.S. Application Data provisional application No. 62/024,912, filed on Jul. 15, 2014, provisional application No. 61/944,744, filed on Feb. 26, 2014, provisional application No. 61/909,679, filed on Nov. 27, 2013.

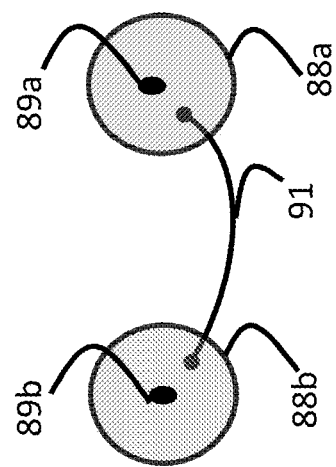
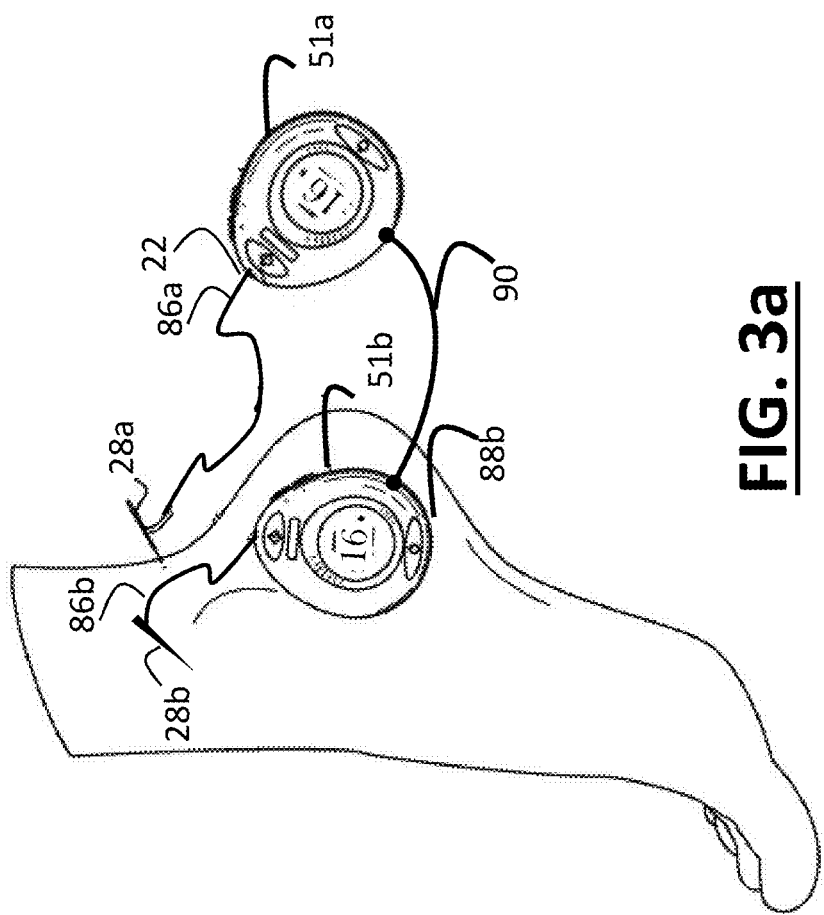

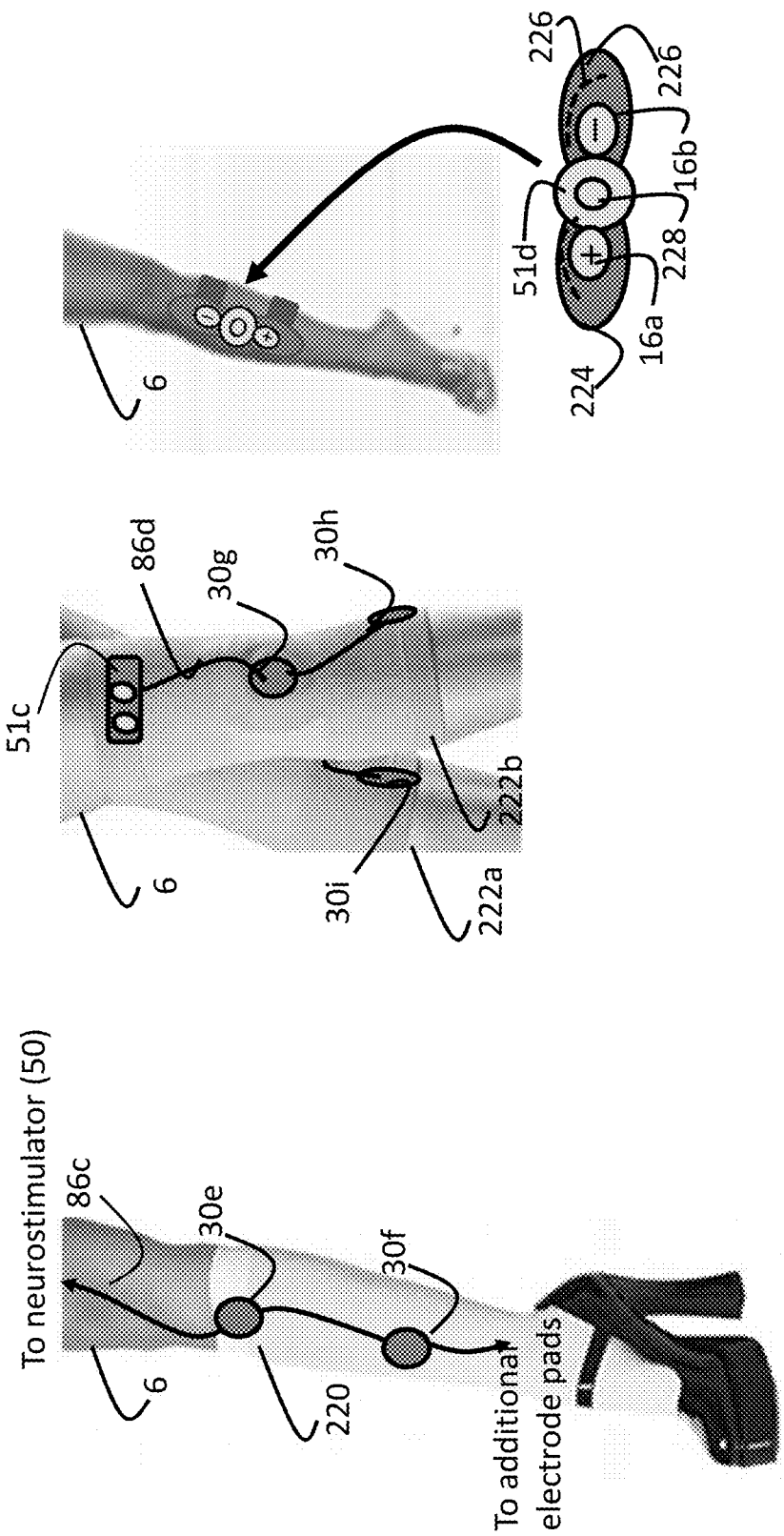

Treatment Regimen 350

| | Timing | Parameters | Time | Max | Min | Permission |
|---|---|---|---|---|---|---|
| Treatment | | | | | | |
| induction (Int) | 2/wk | 9=amp; 20 Hz | 1=30,0=60 | [] | | Doc |
| induction (ext) | 7/wk | 9=amp; 10 Hz | 1=30,0=60 | 10 hr | 4 session | Pat |
| maintainence (ext) | 3/wk | 0=free form; 1= M,W,F | 0=30,1=60 | | | Pat |
| Medication | [] | [] | [] | [] | [] | [] |
| Switch to maintenance | 4 wk; 8wk | OAB>19 OR BD-total>9 | | | | |
| Notification | | | | | | |
| Stimulation | 1/event | Tone; visual | 10=pre;30=post | | | Pat |
| Survey/Diary | 1/event | Tone; visual | 10=pre;30=post | | | Pat |
| Disposable Pads | 1/event | Tone; visual | 5 day=pre; 2 day=post | | | Pat |
| Treatment Events | | | | | | |
| bladder diary | 1=2 day,0=3 day | days 1,2, 30,31, 90-91 | | | | |
| QOL Full | [] | days 1, 30, 90 | | | | |
| QOL Short | [] | every 5 days | | | | |
| Virtual Clinic | [] | 30, 60 | | | | |
| Digital Tools | | | | | | |
| workbook | 2/wk | | | | | |
| Videos | | | | | | |
| apply electrodes | [] | week 1-2 | | | | |
| correct location? | [] | week 1-2 | | | | |
| planning ahead | [] | week 1-2 | | | | |
| Noticing changes | [] | week 3-4 | | | | |

FIG. 17

Notification Parameters and Rules

| Treatment | Timing | Parameters | Type | Max | Rule | Permission |
|---|---|---|---|---|---|---|
| induction (ext) | Before; After | 15 minutes; 1 hour | Text; text+tone | 3.5 | 1/2 | All |
| maintainence (ext) | Before; After | 15 minutes; 1 hour | Text; text+tone | 3.5 | 4/8 | All |
| Medication | Before | 15 minutes; 1 hour | text+tone | 1 | | Doc |
| Survey/Diary | Before; After | 15 minutes; 1 hour | text+tone+voice | | | All |
| Disposable Pads | Before; After | 15 minutes; 1 day | text+tone + voice+cart | | | [] |
| Treatment Events | | | | | | |
| bladder diary | Before; After | 15 minutes; 1 hour | text+tone+voice | 4 | | All |
| QOL Full | Before; After | 15 minutes; 1 hour | text+tone+voice | 2 | | All |
| QOL Short | Before; After | 15 minutes; 1 hour | text+tone+voice | 4 | | All |
| Virtual Clinic | Before; After | 15 minutes; 1 hour | text+tone+voice | 1 | | Doc |

Gamification Points

| | Timing | Positive | Negative |
|---|---|---|---|
| Treatment Behavior | | | |
| Provide treatment <1 hour from notification | always | 2 | -1 |
| provides >59 min | always | 1 | 0 |
| provides >119 min | always | 1 | 0 |
| Surveys | | | |
| QOL | 1/wk | 2 | -1 |
| Bladder Diary | 1/month | 20 | -5 |
| Symptom survey | 1/day | 1 | -3 |
| Watch Video | | | |
| How to stimulate | 1st month | 1 | -1 |
| Lifestyle changes | always | 1 | 0 |
| Pelvic Floor Exercises | always | 5 | 0 |
| Social | | | |
| Interact with Sapho community in app | always | 1 | 0 |
| VideoMedConsult | always | 7 | -3 |
| Behavioral | | | |
| Replace pads within 5 days of target | always | 1 | -2 |
| Reduction Coffee/Tea Intake | Always | 1 | 0 |
| Pelvic Floor Exercises | Always | 3 | 0 |

FIG. 20

SYSTEMS FOR IMPROVING NEUROSTIMULATION COMPLIANCE USING A PATIENT INTERFACE MODULE

REFERENCE TO RELATED APPLICATIONS

This Patent Application is a continuation of patent application Ser. No. 16/228,204 filed Dec. 20, 2018 which claims benefit of U.S. Provisional Application Ser. No. 62/608,540 filed Dec. 20, 2017 and is a continuation-in-part of patent application Ser. No. 15/678,824 filed 16 Aug. 2017 which claims the benefit of U.S. Provisional Patent Application Ser. No. 62/375,898 filed 16 Aug. 2016 and is a continuation-in-part of patent application Ser. No. 15/160,468, which claims the benefit of U.S. Provisional Patent Application Ser. No. 62/171,549 filed 5 Jun. 2015, and Ser. No. 62/165,037 filed 21 May 2015, and claims the benefit of patent application Ser. No. 14/553,427, filed Nov. 25, 2014 entitled Systems and Methods of Enhancing Electrical Activation of Nervous Tissue which is based upon of Provisional Patent Application Ser. No. 61/909,679, filed 27 Nov. 2013; Provisional Patent Application Ser. No. 61/944,744, filed 26 Feb. 2014; and, Provisional Patent Application Ser. No. 62/024,912, filed 15 Jul. 2014.

INCORPORATION BY REFERENCE

This Patent application hereby incorporates by reference, U.S. patent application Ser. Nos. 16/228,204, 15/678,824, 15/438,415, 15/160,585, 15/160,468 and 14/553,427, and U.S. patent applications Ser. Nos. 61/909,679, 61/944,744, 62/024,912, 62/165,037, 62/171,549, 62/375,898, and 62/608,540 which are hereby incorporated by reference in entirety for all purposes.

FIELD

The subject concept relates to the field of modulating biological tissue.

BACKGROUND

Nerve stimulation (neurostimulation) technology includes applications such as electrical neuromodulation, functional electrical stimulation, and therapeutic electrical stimulation. Nerve stimulation is an effective clinical tool used to treat various chronic medical disorders and conditions. Examples include (1) deep brain stimulation (DBS) for treating Parkinson's disease and essential tremor, (2) spinal cord stimulation for treating pain and voiding disorders, and (3) peripheral nerve stimulation for treating pelvic floor disorders and dysfunctions (e.g., overactive bladder), pain, obstructive sleep apnea, headache, migraine, epilepsy, depression, hypertension, cardiac disorders, and other disorders and disease states. Peripheral nerves may include, for example, the vagus nerve, occipital nerve, cranial nerves, spinal nerves, pudendal nerves, cutaneous nerves, and the sciatic and femoral nerves.

The peripheral nervous system provides a neural substrate that allows nerve stimulation to treat various disorders. Long-term viability of implanted neurostimulators can be complicated by issues related to repeated mechanical movement (e.g., lead fracture and/or component migration). Transcutaneous electrical nerve stimulation (TENS) can provide a more simple and non-invasive approach. However, selective nerve activation by TENS may not be readily achieved due to, for example, intervening tissue or distance between a nerve target and the skin surface. Accordingly, some therapies rely on percutaneous stimulation to stimulate a target nerve.

Advances in minimally-invasive nerve stimulation have been realized clinically. Wireless implantable electrode probes have been developed for achieving less invasive methods of selective nerve stimulation. The BION (Advanced Bionics) is a glass or ceramic covered electrode that can be percutaneously injected into a region of interest. It can be self-powered or passively charged by radio frequency (RF) pulses. Long-term use may be complicated by migration of the BION from its original implant location. This migration may cause both reduced therapeutic effects and increased stimulation-evoked side effects due to activation of other (non-target) tissue. Nerve stimulation systems (e.g., MicroTransponder Inc. SAINT™ System) which are smaller, less expensive, and/or less technically complicated than the BION may be advantageous in treatment of some disorders. StimGuard has developed injectable implantable neurostimulators, which use wireless power in the RF and/or microwave frequency rage and non-inductive antennas which receive electromagnetic energy radiated from a source located outside of the patient's body. Energous technology is developing wireless technology that utilizes multiple antennae to provide improved transmission and harvesting of wireless energy and is developing within the implantable device space. These innovative technologies will allow smaller form factors. Witricity is using wireless magnetic induction technology to power implanted devices. Alternatively, Valencia Technologies has developed a coin-shaped implantable neurostimulator disclosed, for example in US App Nos. 20140214128A1, US20140214144A1, US20150148864A1, (all to Peterson et al.), which has a battery which may not be rechargeable, and which can last 2-3 years when providing periodic stimulation for disorders such as overactive bladder.

Transcutaneous magnetic stimulators (TMS), termed "transcranial magnetic stimulators" when used for brain stimulation, are used to treat disorders such as migraine (e.g. those made by Neuralieve Inc. such as U.S. Pat. Nos. 7,294,101, 8,262,556) by using an external magnetic stimulation device to stimulate central or peripheral tissue targets. The fields induced inside the tissue by one or more pulses (e.g., such as may occur with pulsed electromagnetic stimulation) may be less localized than desired. The present invention may offer advantages related to enhancing the effects of externally applied magnetic and/or electrical fields near a target nerve.

In addition to pain treatment, TENS systems have been used to apply electrical fields to the brain to modulate sleep, anxiety, depression, pain, attention, memory, and various types of brain activity. TENS systems are being developed to enhance performance of athletes by stimulating a person's head, although the mechanisms of action are not fully understood. TENS is not currently used to reliably treat certain disorders such as overactive bladder. This may be due, at least partially, to the difficulty of modulating the posterior tibial nerve which may be too deep for sufficient portion of the TENS signal to modulate the nerve target. The disclosed systems and methods may allow a TENS system to stimulate novel anatomical areas and nerve targets in the treatment of overactive bladder.

The first largely available percutaneous nerve stimulation method and system for treatment of overactive bladder was provided by Uroplasty under the name "Urgent PC". The therapy involves posterior tibial nerve stimulation using a percutaneous needle electrode at a site above and posterior to the patient's medial malleolus which stimulates in conjunction with an electrode attached to the medial side of a patient's foot. The method and system has been described in U.S. Pat. Nos. 6,493,588, 7,668,598, 8,046,082, 8,812,114, 9,056,194, 9,265,941 assigned to Uroplasty. The Urgent PC system design incorporates a "use" status when the device is ready to provide therapy and a "do not use" status when the device is not ready. The device works with a lead set having a status flag element with a "use" status which converts to a "do not use" status at a predetermined time after starting the therapy. The status change includes blowing a fuse of the lead set so that the lead cannot be re-used for subsequent therapy. Single-use leads require a new lead must be purchased and used for each subsequent provision of therapy.

A more recent alternative percutaneous nerve stimulation method and system has been described in U.S. Pat. No. 8,660,646 entitled "Percutaneous tibial nerve stimulator" to Laing et al. The disclosure describes a system developed by Advanced Uro-Solutions and now distributed under the name NURO by Medtronic. The system uses a method that includes providing a computer system having a customer interface and a neurostimulator unit that is operated in conjunction with the interface. The neurostimulator contains a pulse generator that is electrically coupled to a transcutaneous electrode configured to be applied to skin of a patient (e.g. inner foot) and a percutaneous electrode for insertion at stimulation site of a patient which is the posterior tibial nerve. A microcontroller communicates with the pulse generator and allows for the monitoring of how many treatment credits are available to be used by the neurostimulator. If there is at least one treatment credit, the microcontroller allows for activating the pulse generator and decrements the treatment credit counter when a treatment is provided to a patient. The system also provides for a computer system that can receive a treatment credit request transmitted through the customer interface and adjusting the number of treatment credits available based on the number of treatment credits purchased. Accordingly, the system allows for treatment to be accomplished if the treatment has been paid for by obtaining a treatment-credit beforehand.

These prior art systems suffer limitations. These provide a single stimulator (e.g., configured to provide a single percutaneous electrode for insertion at a single treatment site near the ankle). More than one stimulation site may be beneficial and stimulating the saphenous nerve near the knee may have advantages. Stimulation systems may not allow for providing more than one treatment across an interval (e.g., 3- or 24-hours) although all treatments may be related to a single event or disorder, but with greater severity, requiring a larger "dose". For example, treatment credits are related to a single stimulation session lasting a defined duration.

The prior art percutaneous stimulation devices for treatment of OAB by stimulation of the posterior tibial nerve (PTN) suffer additional disadvantages and limitations. For example, they are designed for percutaneous stimulation of the PTN rather than for percutaneous or transcutaneous stimulation of the saphenous nerve, or for a combination of different stimulation methods (e.g., first percutaneous and then TENS, using a combination of external and implanted neurostimulators).

Another disadvantage is that prior art stimulators are not configured to adjust stimulation parameters for, and then provide stimulation with, signals provided at two or more percutaneous stimulators that are applied to the patient to provide stimulation of targets including, for example, both the PTN and the saphenous nerve (SAFN). There is no provision for display of different stimulation parameters related to two or more targets.

Another disadvantage is that prior art stimulators (e.g. percutaneous, magnetic, etc) used for treatment various conditions implement a pay-per-session paradigm. For example, in the treatment of OAB (or migraine) there is a charge to stimulate at a single stimulation site. This does not allow for stimulation using 1 or more neurostimulators or for nerve stimulation using needles at two stimulation sites. This also does not allow for requiring payment to activate a device for a single interval of use rather than for each of a plurality of uses within that interval (e.g. several therapy sessions on a single day).

Another disadvantage is that prior art TENS stimulators (which work either jointly, with or without, implanted components) are not configured to provide treatment related to overactive bladder with features that promote compliance and therapy benefit. Prior art TENS stimulators are also not configured to provide stimulation of the saphenous nerve in the treatment of overactive bladder or other pelvic floor disorder.

Systems and methods are needed which provide advantages for both clinic-based and home-based therapy such as one or more of the following: a) providing at-home stimulation treatment to patients contingent upon a subscription being valid; b) allowing for providing a selected number of treatments within the course of a selected, and programmable, treatment window such as a 6, 12, 24 or 48 hour period, or an interval of weeks or months; c) monitoring, recording, displaying, reporting, sending and operating upon usage data related to treatment times, durations, compliance, non-compliance, and other characteristics of patient use; d) alerting doctors, caregivers, or patients to promote compliance and/or when non-compliance or incorrect-use occurs; e) providing the selection of session-based, dose-based, interval-based, local-based and remote-based use-management; f) providing TENS systems configured for OAB treatment and/or stimulation of the saphenous nerve to provide treatment of other disorders or provide other benefit; and g) providing a gamification system that increases the fun and entertainment value of the treatment, augments compliance, and rewards the user for providing treatment in the intended manner.

SUMMARY

In an embodiment, a transcutaneous tissue stimulation system and method is provided which includes one or more electrical generators positioned external to a patient. Stimulators which are either needle or TENS electrodes are electrically coupled to the one or more electrical generators and are positioned on the surface of, or penetrate, the patient's skin. Multiple target nerves may be defined with different stimulation protocols as part of the treatment program.

In embodiments, systems and methods are provided for achieving effective therapeutic nerve activation of the SAFN with TENS of the medial portion of a patient's leg between approximately the knee and the medial malleolus which can enable a primarily home-based TENS therapy treatment for OAB to become a simple (e.g. first-line) treatment option similar to lifestyle changes, or a second line treatment option to be used rather than drug therapy, since this does not require ongoing, frequent clinic-visits for percutaneous intervention.

In embodiments, stimulation systems and methods are described for providing advantages related to increasing therapeutic efficacy of nerve stimulation, improving the comfort of a patient relative to alternative therapeutic solutions, increasing patient compliance, decreasing the cost of treatment, and/or providing for a simple treatment using external and/or implanted components.

In embodiments, an implanted, electrically conductive member is positioned on, or contiguous to, a target nerve tissue for stimulation of the target nerve tissue to modify the electrical field signals generated by the electrical generator and provided by the stimulator for the purpose of modulating signals from the nerve tissue to the brain, to the central or peripheral nervous system, or other target, of the patient. System and methods aim to avoid activation of non-targeted nervous tissue, which can both limit the overall therapeutic effects and exacerbate stimulation-evoked side effects. The implanted passive element is configured to allow therapy to achieve the same, or improved therapeutic benefit as that which would otherwise be achieved when using only transcutaneous nerve stimulation without an implanted passive element. The systems and methods for providing stimulation of tissue using complementary or "paired" configurations of external stimulation elements and subcutaneously implanted passive elements.

Another objective is to provide systems and methods for achieving effective therapeutic nerve activation with relatively lower stimulation amplitude and/or shorter pulse width than what is typically achievable using prior art methods (e.g., TENS).

While the systems and methods disclosed herein are generally oriented for peripheral nerve stimulation, these may also be applied to stimulation of other targets of the spine, brain, or body.

These and other objectives and advantages of the invention will now be disclosed in the figures, detailed description, and claims of the invention.

In the illustrated embodiments, any steps shown in the figures may occur in a different order, may be repeated, may lead to different steps of the method shown within each figure, or may lead to steps shown in other figures. Steps and components shown may be included or excluded from a particular embodiment, and this may occur conditionally, or according to the system or treatment protocol implemented by a therapy program. The therapy program may be implemented partially or fully by one or more processors of a medical system which may include an external, or a partially or fully implantable neurostimulator. The therapy program can be adjusted according to control by, or therapy plan implemented by, a patient, doctor, remote medical service, or caregiver.

BRIEF DESCRIPTION OF THE FIGURES

FIG. 3A is a view of a neurostimulation system having two neurostimulator devices applied to two portions of a single leg of a patient according to an embodiment of the invention;

FIG. 3B is a view of a TENS electrode linking system for linking the TENS circuits of two neurostimulator devices according to an embodiment of the disclosure;

FIGS. 11A,B,C show alternative TENS accessories and embodiments for use with the current invention.

FIG. 17 shows an example of a look-up table related to treatment regimen event parameters.

FIG. 18 shows an example of a look-up table related to notification parameters and rules.

FIG. 20 shows an example of a look-up table related to gamification points.

DETAILED DESCRIPTION OF THE PREFERRED EMBODIMENTS

Reference will now be made in detail to exemplary embodiments of the present disclosure, examples of which are illustrated in the accompanying drawings. Where possible, the same reference numbers will be used throughout the drawings to refer to the same or like components. When titles are provided for different sections of this disclosure these are merely to highlight certain themes and are not meant to limit the invention concept.

Figure 1:
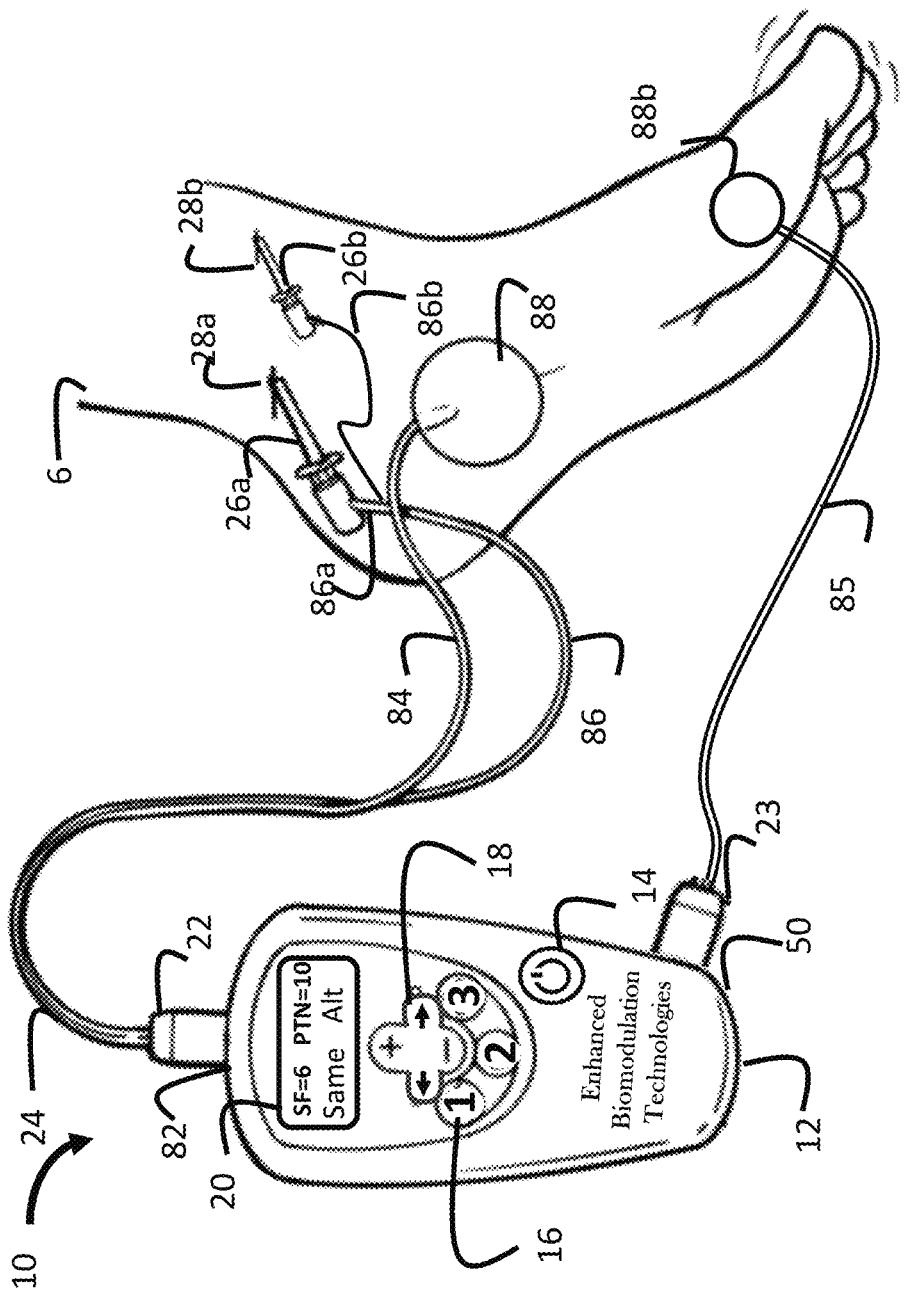
FIG. 1 is a view of a neurostimulation system applied to a patient for stimulating the saphenous and posterior tibial nerve targets according to an embodiment of the invention.

FIG. 1 shows an embodiment of neurostimulation system 10 applied to a patient for stimulating one or more targets in the leg of a patient 6 which in this example are a saphenous nerve target and posterior tibial nerve target. The neurostimulator 50 has a housing 12 and a power button 14 for turning the device on and off. A set of dedicated button controllers 16 (labeled 1, 2, and 3 in the figure) provide functionality such as for starting stimulation (e.g. beginning a treatment session that will last a selected time interval), pausing stimulation, and halting stimulation. The "pause" function can allow the therapy to be paused and restarted within a specified interval after the stimulation is started without blowing a fuse of the electrode lead set (Uroplasty type system) or decrementing the treatment credit (Nuro type system). This can allow for the needle to be repositioned if needed. A menu controller 18 operating in conjunction with the user interface module 80 allows a user to navigate through a set of menu options presented on the display 20 to select and/or adjust operation of the system 10. For example, a user can adjust a therapy protocol parameter such as the amplitude of at least one stimulation signal that may be selectively provided to one, two, or more stimulators such as a first and second percutaneous needle electrode 28a, 28b. The display 20 is configured to present a user with information about stimulation parameter values related to stimulation of at least a first target (e.g. SAFN) and also a second target (e.g. TN) when two or more stimulation targets are modulated during therapy for overactive bladder or other disorder.

A conduit connector 22 is formed as a plug that connects the neurostimulator 50 to a lead set 24. In an embodiment, the lead set connects to a first lead 84 which connects to a surface stimulator TENS electrode 88 and a second lead 86 which is multi-stranded and branches into individual wires 86a and 86b, which may be single or multi-stranded, and which provide the stimulation signals to two needle electrode clips 26a, 26b. In an alternative embodiment, stimulation is only delivered to the SAFN and a single wire 86b, clip 26b, and needle electrode 28b are provided. In other words, lead set 24 can communicate the stimulation signal to the TENS electrode 88 and only to one needle holder 26b, when only 1 percutaneous needle stimulator is used. The system 10 may also be designed so that stimulation signals travel between the two needle electrodes 28a, 28b and a TENS electrode 88 is not provided.

In the illustrated embodiment, needle electrode 28a is inserted percutaneously at a first location cephalad and posterior to the medial malleolus, while needle electrode 28b is inserted at a second location to stimulate the SAFN, such as a location cephalad and anterior to the medial malleolus. The surface electrode 88, is positioned on the medial surface of a foot of a patient 6 (other locations below or above the ankle are also viable).

The display 20 shows a setting of "6", reflecting amplitude or strength of the stimulation signal applied at needle electrode 28b for "SF" (i.e. SAFN) stimulation, while "10" reflects amplitude of stimulation applied at the PTN site. The user has selected a stimulation protocol parameter value of "Same" which indicates that the stimulation is supplied to the SAFN and PTN at the same time, rather than "Alt" which would cause the sites of stimulation therapy to alternate. Alternating may include, for example, periodically stimulating for 5 minutes at the first target site followed by 5 minutes at the second, and so on. Alternating can also include stimulating at 10 Hz at both SAFN and PTN, with two stimulation signals that are time lagged to be out of phase such that the combined signal of the 2 interleaved series of pulses is 20 Hz.

The display 20 can also indicate additional information such as a timer value showing the duration of the therapy that has occurred (or the duration remaining), remaining battery charge, stimulator and/or sensor impedance values, errors or faults (e.g., the neurostimulator did not receive a scheduled maintenance or calibration). Information about wireless data and/or power communication strength (or connection status), related to communicating power or data signals between different component of the neurostimulation system 10 and/or the neurostimulator 50 may also be shown. In addition to the display 20, the neurostimulator 50, can also use LEDs 92a/156 (e.g. see FIG. 6, and FIG. 11B) situated on the housing 12 in order to indicate a status of a measure such as impedance (e.g. green=good) or to alarm/alert the user about the status of therapy or device operation. The display 20 can be much larger than that shown in the figure, and may be supplied on a user programmer 70 to enable clear presentation of graphs and tables related to usage and compliance. In an embodiment, the display 20 can also display treatment credit information.

In alternate embodiments, either the graphic display 20 or some of the user interface controllers may be realized as detachable from the neurostimulator housing 12. For example, the neurostimulator 50 may be controlled by a user who has established wireless communication link between it and a smartphone, tablet, laptop or other device, that may serve as type of user programmer 70 (which is a device such as a computer having a control module with controller circuitry such as a processor, display, memory, power source, communication means, and other circuitry as is well known, see FIG. 2). Remote controlling of the device 50 can be provided in addition to, or as an alternative to, the user input buttons 18 and display 20 on the housing 12. The neurostimulator 50 can communicate using wireless signals (e.g., infrared, Bluetooth, WIFI) or by wired connection, and can send data over the internet. A user's laptop can be provided with a software application that provides instructions to a processor for linking with, and subsequently control of, at least one neurostimulator 50 as well as serving as a display/controller device. Either the neurostimulator or the linked device can operate to notify a user (patient or administrator) by sending a visual, sonic, or other alert signal indicating a status or parameter value related to the provision of treatment using the user interface module 80 and related alerting components 156.

In an embodiment, a stimulation signal with a fixed frequency (e.g., 20 Hz and a pulse width of 200 usec) is increased until a behavioral response is seen such as flexion of the big toe or fanning of all toes becomes visible, or until a subjective response is made (e.g., tingling sensation is reported radiating towards the foot or toes). However, in some patients, such as those with diabetes and various neuropathies, a subjective report may not be accurate or subjects may be unsure of whether a nerve is being stimulated for various reasons. According to an embodiment of the present invention, using sensor data enables the detection of a quantitative measure such as a motor evoked response. In an embodiment, a second connector 23 connects the neurostimulator 50 to a lead set 85 which connects to at least one sensor such as a disposable TENS surface electrode 88b. In order to monitor nerve or muscle activity (e.g., EMG), the TENS electrode 88b can be realized with two electrical contacts. Alternatively, two disposable TENS surface electrodes can be attached to the lead set 85. The neurostimulator 50 is configured to provide sensing and evaluation of a signal related to the provision of therapy, such as an EMG signal, using the sensing and processing modules 55, 58 to detect a person's foot muscle activation (e.g., toe flexion or extension) in response to the stimulation of the PTN. Alternatively, measuring "muscle twitch" activity could occur using a sensor (e.g. strain gauge or wearable electrode) embedded with a sock or realized in an adhesive band-aid like form factor (which may look like a surface electrode with one or more embedded strain gauges and use a bonded metallic strain gauge design on a flexible backing). Flexion or twisting of the strain gauge will cause change in voltages that signals efferent activation.

Figure 2:
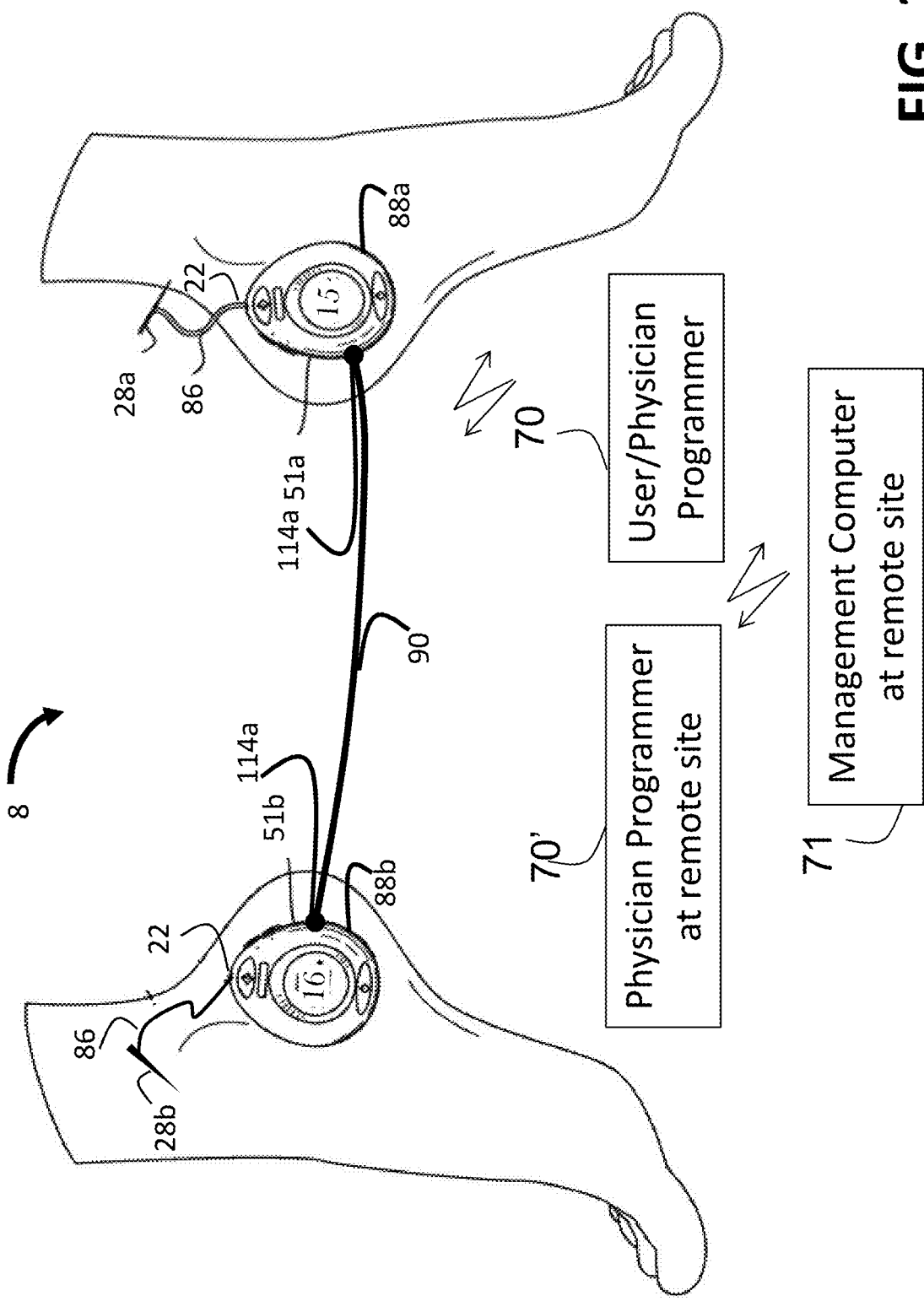
FIG. 2 is a view of a neurostimulation system having two neurostimulator devices applied to portions of separate legs of a patient according to an embodiment of the invention.

FIG. 2 shows an alternative embodiment of a neurostimulation system 8 for stimulating a first and a second nerve target in a first and second leg of a patient. In this case the first target is an anterior branch SAFN target on the first foot (left side of figure) and the second is a PTN target on the second foot (right side of figure). A first and second neurostimulator 51b, 51a are configured to provide stimulation to the SAFN via first needle stimulator 28b and PTN using second needle stimulator 28a (the end of the conduit 86 can be attached to a needle holder which, in turn, attaches to the needle 28, as in FIG. 1, but this is not shown to avoid cluttering of the figure). As shown, the front (i.e., "top") surface of the neurostimulator has displays and buttons. The neurostimulators connect with the patient through a disposable TENS electrode 88a, 88b that can be attached to the back (i.e., "bottom") surface of each neurostimulator 51a, 51b (e.g. the electrode can snap onto an electrically conductive snap on the back side of the stimulator). Attachment of both neurostimulators to the patient completes the stimulation circuit for each foot. This configuration may be useful, for example, in patients who are receiving stimulation therapy for both the SAFN and PTN, but who have trouble tolerating (or have difficulty in being able to distinguish or assess) stimulation of both targets in the same leg. In an alternative embodiment, stimulation is only delivered to the SAFN of both the left and right leg by neurostimulators 51a,51b.

Although a neurostimulator 51b and its associated lead set 86 can be designed to provide stimulation of two or more stimulators 28 (as shown for the system 10 of FIG. 1), there may be manufacturing and regulatory advantages to use a neurostimulator design that has already been approved by regulatory agencies for stimulation of a single site on one leg and also factors related to patient comfort. Additionally, using neurostimulators that have hardware, software, and protocols designed for stimulation of a single site may be easier than designing a more complicated stimulator and user interface to stimulate more than one nerve target using a single stimulator. For at least these reasons, the system 8 can use neurostimulator embodiments that provide for joint operation of, and/or connection between, two or more neurostimulators.

When two neurostimulators 51a, 51b use a pay-per-use, or pay-per-therapy-session, or other treatment-credit-based system, then a therapy protocol which includes stimulating two different targets in single patient may require certain features to avoid problems that would otherwise occur. For example, although two stimulators are being used during a single treatment, it may not be desirable or appropriate to charge for two different treatments and decrement the treatment credits by 2 rather than 1. Several solutions are provided by the systems and methods disclosed herein. In an embodiment a user/physician programmer 70 may communicate in a wired or wireless manner with the payments and permissions modules 202 of the first and second neurostimulators 51a, 51b such that both neurostimulators can be activated to provide a treatment but only one neurostimulator will have its treatment credit value decreased. In the figure the neurostimulator on the right side of the figure has had its credit reduced by 1, to 15, while the neurostimulator on the left remains at 16 credits during the provision of the current treatment. Alternatively, the user/physician programmer 70 may be responsible for management of the treatment credits and sends activation codes to the neurostimulators 51a, 51b which simply obtain permission from the user/physician programmer 70 to provide treatment. Alternatively, one of the first and second neurostimulators 51a, 51b is designated a 'Master' device while the other is designated a 'slave'. The designation can be implemented using either hardware or software or both, and may be realized as part of the payments and permissions module 202. For example, the master device keeps track of the payment credits and the slave device is controlled by the master device, and may not be used or controlled in the absence of the master device. In an alternative embodiment, a patient-specific tag signal (e.g., a low amplitude sinusoid modulated by a combination of two or more frequency components and one or more silent periods) can be transmitted by one stimulator and must be sensed by a second stimulator to ensure the two stimulators are attached to the same person. The signal is transmitted and received wirelessly using near range communication by the communication modules 68, or is transmitted by one stimulator 51a through the patient tissue and sensed by the other stimulator 51b, whose sensing module 55 is configured to detect this signal. Using a treatment credit system for payment may be more easily applied to stimulation of 2 or more sites since using a needle stimulator with a fuse increases the cost of treatment when 2 sites are used.

In embodiments, various limitations may be imposed by the payments and permissions module 202 to deter fraudulent treatment of two patients while only being charged for 1 treatment. For example, both stimulators can be simultaneously activated to provide therapy, but an operation limitation requires that the start of therapy must occur within 5 minutes of a communication session with the user/physician programmer 70 for both a first and second neurostimulator 51a, 51b. Alternatively, the first and second stimulators 51a, 51b can be required to periodically attempt communication with each other during the provision of a therapy session and if this is not successful (e.g., for at least 1 of 4 attempts) then it may suggest that the devices are being used in 2 locations with 2 different patients. If this requirement was not met, then the system 8 can be designed so that the "activation" of at least one of the two neurostimulators is halted so that it does not provide therapy or an alert signal is sent indicating that the two devices are not communicating correctly. Wired or wireless communication can be provided by the communication modules 68 of the neurostimulators, and also of the programmer 70. A near field wireless technology can be used to establish a communication channel that allows for approximately only, for example, a 1 to 2 foot range for communication in order to ensure that the two neurostimulators are in close proximity. Additionally, a conduit 90 such as a microUSB, or custom, cable can be inserted into one of the I/O ports 114a of each neurostimulator, and the two neurostimulators can communicate in a wired manner to allow the therapy to be delivered using the appropriate allocation of a single treatment credit.

The neurostimulators 51a, 51b and a user/physician programmer 70 can communicate to transmit data and/or power signals to each other. The user/physician programmer 70 can, in turn communicate with a remote management computer 71, and can relay communication between other system 8 components. The management computer 71 may be at least one computer, or part of a network of computers that operate software instructions under control of their processors to manage aspects of the therapy such as purchase and delivery of payment credits and/or recording, assessing, and reporting data related to times and durations when therapy was provided. The management computer 71 can set flags and operational values related to use, payment, and compliance, as well as other relevant data. In an embodiment the user/physician programmer 70 can communicate with a remote management computer 71 to transmit a signal over a computer network to submit a request for one or more treatment credits with associated reimbursement codes that are related to providing stimulation using either one neurostimulator or more than one neurostimulator (or one stimulator which is being used to treat one or more sites). In the latter case, in an embodiment, the remote management computer 71 can provide the user/physician programmer 70 with therapy credit that is designed to allow for the activation of two neurostimulators to be used in treatment of a single subject. In additional embodiments, rather than one or more neurostimulators keeping track of the therapy credits, the user/physician computer 70 can manage the treatment credit usage. For example, the user/physician computer 70 can provide an activation code signal to the two or more neurostimulators and then operate its processor to decrease the treatment credit value stored in its own payments and permissions module. For tracking purposes each treatment credit may have a unique ID value. The ID value may contain fields for information about when, where, and how the credit was purchased and/or used. The ID value accordingly may have a plurality of fields, some of which are modifiable by a programmer or neurostimulator.

In an embodiment, when the neurostimulators 51a, 51b are used in the setting of a patient's home or are otherwise used outside of a clinic setting to provide therapy stimulation then the user/physician programmer 70 can communicate with the neurostimulators 51a, 51b and with a remote management computer 71 that manages aspects of the therapy. This is true regardless of whether the therapy is at least one of: transcutaneous (e.g., via electrical, vibratory, magnetic, or other modality), occurs under control of an external device that provides control and/or power of an implantable device that provides therapy, occurs by the programmer 70 communicating with an implantable device to adjust the operations relate to therapy, or otherwise. Additionally, the user/physician programmer 70 in a patient's home may communicate with a remote physician programmer 70' at the patient's physician's office which may, in turn communicate with the remote management computer 71 in order to manage the patient's therapy. In other words, the physician programmer 70' at the physician's office can act as a relay between the user/physician programmer 70 at the patient's home and the management computer 71. The management computer 71 may be operated by a medical company that charges users or doctors for ongoing use, per-treatment use, time-based rental, purchase, and/or periodic activation of the neurostimulators for selected intervals of time (e.g. 1 hour or 1 month). The management computer 71 may in turn send and receive information with computers of insurance companies in order to carry out operations related to insurance monitoring and reimbursement. Rather than a user programmer 70 communicating directly with a medical company or insurer, a clinic may prefer the user programmer 70 to communicate with the physician programmer 70' at the clinic, which in turn communicates with the management computer 71. This indirect route of sending data over a computer network, by routing information through the clinic may be preferable for the clinic (who may wish to charge or monitor user treatment) and also for a medical company that may choose not to directly communicate with or receive data from patient devices. Additionally, during a periodic exchange of data related to device payment, data relating to device use (stimulation times, durations, and stimulation parameters) can be exchanged. The transmission of user data from user devices to a physician programmer 70' may provide a doctor with the opportunity to review the usage of a particular patient rather than requiring this information to be acquired during a patient visit. In some instances, this may reduce the need for more frequent patient visits. In an embodiment, user compliance data (e.g. whether a patient successfully self-stimulated at least a minimum number treatment sessions per week) can be at least periodically communicated with either a doctor's office (e.g. management computer 71) or an insurance company or both. The management computer at remote site can be a computer that is managed by an insurance company, or the management computer 71 may be part of, or communicate with, a network of computers operated by a reimbursement stakeholder.

When a needle-type electrode is used to percutaneously stimulate the saphenous nerve, it may be constructed using an electrically-insulating material that has an electrically-conductive contact located at the distal tip. Such a design would reduce the electrical activation of nervous tissue at the skin and minimize discomfort or pain felt by the patient in this area. In an embodiment, a pulse generator of a stimulation module 54 of the neurostimulator 50 is electrically coupled to both an electrode TENS pad 88 and a percutaneously inserted needle electrode 28b for stimulating the SAFN. During stimulation treatment, current pulses of the stimulation signal traverse the stimulation site by passing from the TENS electrode 88 to the conductive portion of the needle electrode 28b. Additionally, the subject system can be configured to operate a needle stimulator with two contacts (e.g., conductive annular rings) formed on an insulated needle that serves as a bipolar electrode. In an embodiment, two conduits can connect to two contacts on the top of the needle stimulator which respectively connect to the first and second annular ring. The needle does not need to be conductive and can be made of plastic or other suitable non-conductive material that has electrical routing disposed along its length provided by conduit means. When two needle electrodes are used on the same foot, the current pulses can pass between a TENS electrode and each needle electrodes 28a, 28b (see FIG. 3A). Alternatively, when two needle electrodes are used to achieve bilateral nerve stimulation, the current pulses can pass between each respective pair of TENS electrodes and needle electrodes 28a, 28b. In some stimulation protocols, the TENS electrode 88 and the needle electrodes 28a, 28b are designated as anode and cathode, respectively, while in others these designations change over time. In an embodiment, the TENS electrode is not used, and the current pulses can travel between the two needles 28a, 28b.

FIG. 3a shows an embodiment of neurostimulation system 8 applied to stimulate a first and a second target in the same foot of a patient 6. A first and second neurostimulator 51b, 51a are configured to provide stimulation to the SAFN using needle stimulator 28b and PTN using needle stimulator 28a. A disposable TENS electrode 88a is connected to the bottom surface of neurostimulator 51b to complete the stimulation circuit with needle stimulators 28b, 28a. There may not be sufficient surface area on the medial side of a patient's foot for both stimulators. Further due to patient comfort, or for other reasons, it is not preferable for the second neurostimulator to be placed elsewhere on the patient. Accordingly, a neurostimulation linking system can be realized using a communication cable 90 which connects to I/O connectors 114a provided in the housing 12 of each neurostimulator (see FIG. 2). In an embodiment, I/O connectors 114a connect to various components of the neurostimulators 51b, 51a including a circuit 145 (see FIG. 9) that electrically joins the circuitry of the stimulation module that connects to the TENS electrode used for the neurostimulator 51a, to the electronics connected to the TENS electrode 88a of neurostimulator 51b. This allows the disposable TENS electrode 88a of the first neurostimulator to serve as the return path for the second neurostimulator as well. The neurostimulation linking system can also be designed to enable data signals sent using wires of the communication cable 90 such as those related to the operation of the payments and permissions modules 202 of both neurostimulators. Communication cable 90 enable the modules of the two systems to collaborate to provide stimulation while also managing treatment credits appropriately (e.g., decrementing the treatment credits of only 1 of the neurostimulators due to the provision of a single therapy session).

An alternative system and method of connecting the two neurostimulators, which also does not require the second neurostimulator to be attached to the patient's foot, is shown in FIG. 3b as a TENS electrode linking system. In this example embodiment, two disposable TENS electrode pads can be attached via their electrically conductive snaps 89a, 89b to the bottom of the two neurostimulators 51a, 51b as would typically be done when providing therapy to a patient. The first TENS electrode pad 88b has a bottom side that makes contact with the patient's skin and a top side that snaps onto the first neurostimulator 51b to provide electrical connection from the neurostimulator to the patient's skin. The first TENS electrode pad 88b also has a connector for connecting to a second TENS electrode via a linking cable 91. The second neurostimulator 51a also has a TENS electrode pad 88a that can then be electrically and physically connected to the first TENS electrode pad 88b by a linking cable 91. In this embodiment, the second TENS electrode pad 88a is not attached to the patient and therefore does not require its bottom surface to be adhesive or electrically conductive, although it can be. In an embodiment, the second TENS electrode pad 88a is realized simply as a snap-type connector that snaps to the bottom of the neurostimulator 51a and connects to cable 91. Alternatively, when only one neurostimulator 51b is used, it may be designed to connect to electrode pad 88b to provide stimulation to a patient's skin, and may have 2 stimulation channels for stimulating at 2 different needle electrode sites, both of which are commonly referenced to the pad 88b.

Figure 4:
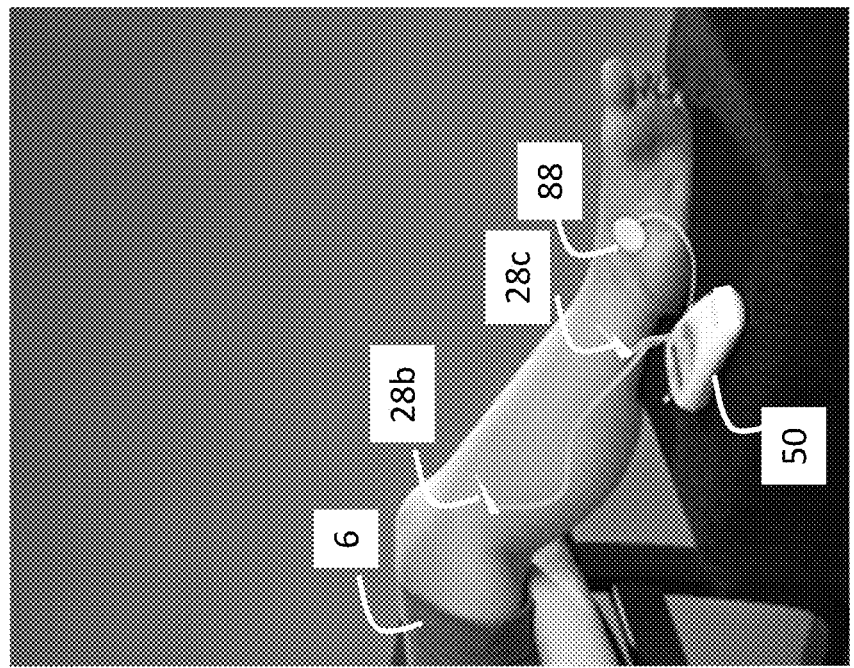
FIG. 4 is a view of a neurostimulation system applied to a leg of a patient for providing percutaneous stimulation according to an embodiment of the disclosure.

FIG. 4 shows an embodiment of a neurostimulation system applied to a leg of a patient 6 for providing percutaneous stimulation. The neurostimulator may be configured to provide stimulation of the SAFN using needle stimulator 28b at a first location near the knee—at a position 2-3 inches distal to the knee and on the medial surface. More specifically, the SAFN can be targeted by inserting a 34 G needle electrode within a 'notch' region located between the medial condyle of the tibia and the superior border of the medial gastrocnemius muscle. It is oriented in the anterior-posterior direction and has a width of approximately 1.5 cm. In a group of OAB patients the notch provided an easily identifiable and reliable region for providing SAFN therapy with percutaneous stimulation. Each patient could confirm activation of the SAFN by sensing electrotactile stimulation (paresthesia) radiating down towards the ankle, and even into their foot (MacDiarmid, John and Yoo *A pilot feasibility study of treating overactive bladder patients with percutaneous saphenous nerve stimulation*). Further in this study we found a robust treatment response with patients showing improvements in multiple bladder symptoms which appears clinical effective in the context of changes typically seen with OAB therapeutics. In a system and method of the current invention, this notch area is used to provide stimulation, or users are instructed to use locations within this area. Additionally, or alternatively, stimulation may be provided using needle stimulator 28c at a second location cephalad and posterior to the medial malleolus to electrically target the PTN. A TENS electrode 88 placed on the medial aspect of the foot (or between the two electrodes, near the tibia at about the level of mid-calf, not shown) may be used to complete the stimulation circuit in the case where one or more needle stimulators are used. Alternatively, the stimulation pathway may be defined simply by using the first and second needle electrodes 28b,28c. Additionally, the first needle electrode and the TENS electrode near the calf may define one circuit and the second needle electrode 28c and the electrode 88 may define a second stimulation circuit. Stimulation of the SAFN using a needle electrode near the knee has been previously shown as a means of guiding the percutaneous injection of lidocaine for achieving nerve block of the foot (Benzon et al. *Comparison of the different approaches to saphenous nerve block*. Anesthesiology. 2005 March; 102(3):633-8). Accordingly, methods for determining the location of the SAFN have been successfully practiced using imaging modalities such as fluoroscopy, ultrasound, and/or electrical stimulation techniques, which can also be incorporated into the currently disclosed therapy for overactive bladder or other disorder. Alternatively, however, subjective responses such as tingling (paresthesia) radiating away from the electrode and along the medial aspect of the lower leg being reported by a subject can be used to select and confirm appropriate locations for electrically targeting the SAFN in providing therapy. When electrically targeting the PTN, the observation of motor evoked muscle activity in the foot and/or the patient's report of sensation radiating along the sole of the foot can be used to select and confirm appropriate target locations for providing therapy. The anatomical sites for targeting the SAFN and PTN may be confirmed independently, and stimulation parameters determined separately, one after the other, prior to providing therapy. Further, a method for determining correct placement of an implanted device may include assessing candidate locations using percutaneous stimulation. The site producing the greatest amount of paresthesia or the lowest threshold of amplitude at which tingling is detected maybe as suitable site for implant. In each patient, the optimal site of percutaneous stimulation may be marked with permanent ink or a tattoo.

Rather than stimulating both the SAFN and PTN, stimulation can occur at two or more different locations along the SAFN and its branches as a means of increasing the therapeutic effects. One needle electrode can target the SAFN trunk (28b) while the second needle electrode 28c can target a different area of the SAFN trunk at a location about halfway between the knee and medial malleolus or the anterior SAFN branch located cephalad and anterior to the medial malleolus. The second needle electrode 28c can also be positioned to stimulate the posterior SAFN branch (and/or the PTN) at a location cephalad and posterior to the medial malleolus. Alternatively, the second needle can be located above the first and can target the infrapatellar branch or other SAFN target above, at, or below the level of the knee. The method of FIG. 13A can be used to position the needle electrodes when providing stimulation at two or more stimulation sites.

As the inventors have described previously (see U.S. Pat. No. 9,610,442), due to the different profile (i.e., frequency response curves) produced when rat SAFN and PTN nerve targets were stimulated, as well as the different spinal projections, it may be that the bladder reflex circuits of the SAFN and PTN are at least partially independent. Accordingly, rather than stimulating only the SAFN, additional improvement may be obtained when stimulating both the SAFN and PTN as part of treatment. It is also worthwhile noting that the acute and prolonged responses to bladder stimulation were different and suggest that individual patients may receive greater benefit when using SAFN relative to PTN (although potentially the opposite may be true in some patients), to treat acute urge incontinence symptoms, while greater prolonged response may be obtained when stimulating the other target.

Figure 5:
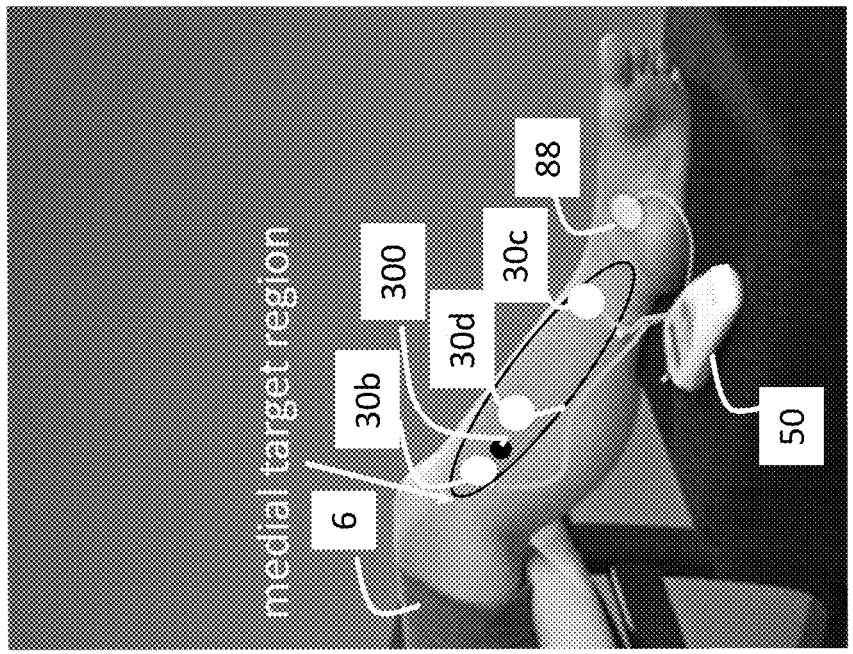
FIG. 5 is a view of a neurostimulation system applied to a leg of a patient for providing transcutaneous stimulation according to an alternative embodiment of the disclosure.

FIG. 5 shows an embodiment of a neurostimulation system applied to a leg of a patient 6 for providing TENS of the SAFN. The neurostimulator 50 may be configured to provide stimulation of the SAFN at a first TENS stimulator 30b at a location on the medial aspect of the leg near the knee, and/or a second TENS stimulator 30c at a location cephalad and anterior to the medial malleolus, and/or a third TENS stimulator 30d placed at a location midway between the locations of stimulators 30b and 30c (and also which may typically be positioned closer to the tibia to lessen concurrent simulation of calf muscles). A TENS electrode 88 can also be placed on the medial aspect of the foot in order to complete the stimulation circuit or pairs of electrodes on the leg may serve to provide two independent stimulation signals (e.g. between 30b and 30d, and between 30c and 88). Alternatively, the stimulation protocol may provide stimulation with a circuit that may only include two electrodes located in approximately the shaded medial region of the leg "medial target region". In an embodiment, additional TENS stimulators may be used along the medial aspect of the leg starting approximately at the level of the knee in order to stimulate the SAFN. While, electrodes can be positioned above the knee or on the lateral surface of the leg, but these may stimulate the sural nerve or other targets rather than the SAFN. This may cause disadvantages in some subjects. For example, if electrodes are placed on both the lateral and medial aspect of the leg, the stimulation pain threshold may be lower for the lateral site. In some people, this may limit the stimulation level that can be provided to the medial target.

The TENS stimulators on the leg 30b, 30c, 30d may be anode, and the TENS electrode on the foot 88 being a cathode (or vice versa), or this status can change with the characteristic of the pulses of the stimulation signal. Only two TENS electrodes on the leg may be used to provide stimulation. Alternative configurations for TENS electrodes (e.g. bipolar pairs, different sizes of TENS electrodes that change the current density, etc) are well known, have been described in the prior art related to providing TENS stimulation, and can be used with the claimed system.

In embodiments, any of the TENS electrodes 30b, 30c, 30d, can also be allocated to serve as a patient ground or be used to measure electrode impedance or nerve/muscle activity before or during stimulation treatment (e.g., between stimulation intervals).

Figure 6B:
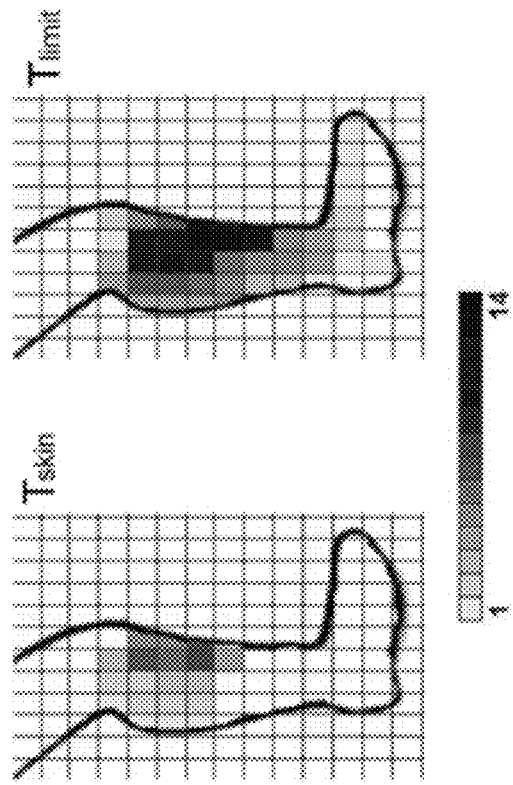
FIG. 6B Shaded anatomical plot of the sensation perceived during SAFN stimulation, showing that as the amplitude was increased from threshold skin (T-skin) to threshold where discomfort was experienced (T-limit), the evoked sensation spread across the entire medial aspect of the lower leg, down to the ankle (N=15 subjects).

SAFN stimulation using TENS with electrodes located at approximate positions 30b and 30d in the figure has been used to provide electrical stimulation of the SAFN in a study conducted by one of the inventors, where data was collected in healthy individuals who did not suffer from bladder disorders such as OAB. In 15 out of 15 subjects (100%), we were able to report a cutaneous sensation of tingling (paresthesia) radiating down their lower leg during surface stimulation (Eshani, Hunter, Hassouna, and Yoo, *Characterizing the transcutaneous electrical recruitment of lower leg afferents for the Non-Invasive Treatment of Overactive Bladder*, BMC Urol. 2018 Feb. 13; 18(1):10). Most participants indicated paresthesia down to the level of the medial malleolus, while some subjects indicated that paresthesia extended to their hallux. FIG. 6B. shows shaded anatomical plot of the sensation perceived during SAFN stimulation, showing that as the amplitude was increased from threshold at which skin receptors were activated (Tskin) to the threshold where discomfort was experienced (Tlimit), the evoked sensation was first felt at the surface electrodes and spread down the medial aspect of the lower leg, past the medial malleolus and even extending to the hallux, reflecting electrical recruitment of the SAFN (N=15 subjects, note: key=14 since there was not common overlap of sensation across subjects). These results suggest, for the first time in humans, that the SAFN trunk could be successfully activated by external TENS stimulators (which were oriented vertically and positioned medially on the lower leg), below stimulation amplitudes that can cause discomfort or pain to the subject. Furthermore, in a subject who did not detect this sensation at the initial stimulation location, moving the TENS electrode to a second target site and repeating the stimulation protocol resulted in successful electrical recruitment of the SAFN at stimulation levels below pain. Review of individual data suggested that while sensory recruitment threshold was lower than nerve recruitment threshold, and both of these were lower than pain threshold, it was not possible to predict one threshold from knowing the other (i.e. nerve recruitment threshold could not be easily used to accurately predict pain threshold). These results support that TENS-based SAFN stimulation at targets selected between the knee and cephalad to the medial malleolus is feasible in human subjects and may serve as an effective method in treating OAB.

Although the maximum amplitude tolerated by participants in this study ranged from approximately 20 mA to 60 mA, other stimulation parameters (such as frequencies between 2 Hz and 50 Hz, or stimulation duration between 15 minutes to several hours) may have different maxima and may be assessed, selected, and then used in patients during therapy, or changed as therapy progresses. In embodiments, the stimulation waveforms can be a carrier waveform with frequency in the kHz range, such as a 5,000 Hz-50,000 Hz (or higher), that is modulated by an activation signal delivered at 5 to 20 Hz. Additionally, other characteristics such as amount of body fat, edema, impedance of skin, and conditions such as diabetes that affects sensitivity to pain may require adjustments in the stimulation waveforms or sites used during therapy for individual subjects, and may be perceived differently than (or not perceived at all such as in the case of some diabetic patients or patients with other medical problems) the stimulation waveforms used in the above study in healthy, young subjects. Additional therapeutic benefit may be obtained by providing the TENS stimulation bilaterally in either a concurrent or alternating manner, with respect to a single treatment session or across individual treatments. Additionally, since the SAFN has been used to successfully produce paresthesia, TENS based stimulation may be used to decrease discomfort associated with foot pain as well as provide treatment in OAB. In an embodiment the maximum amplitude provided by a TENS neurostimulator may range from 100 mA to 200 mA.

Percutaneous TN stimulation therapy treatment sessions typically occur for about 30 minutes once per week during an induction phase, and approximately once per month during a maintenance phase. In contrast, during treatment with TENS in a home setting, subjects may provide SAFN stimulation for at least 30 minutes every day, every other day, or at least once per week during induction. This can occur just as frequently or less frequently, for continued benefit during maintenance. Therapy may also include providing TENS during sleep for least one night per week. Especially during long (e.g. >1 hour) therapy periods, the neurostimulator 50 may realize a stimulation protocol that provides intervals of non-stimulation between the stimulation intervals, for example, 30 minutes on, then 2 hours off, then 30 minutes on, etc. This may provide advantages of both less skin irritation and can also extend periods between recharging or decrease the size of a battery.

The neurostimulator 50 can be programmed with various "SLEEP" protocols and features. These can be selected by a patient at bedtime or be prompted or selected automatically by the system as a function of clock-time. The SLEEP protocol can cause the neurostimulator 50 to gradually increase to a selected therapy amplitude across a period of 1 hour, and/or delay onset by 1 hour, to decrease the risk of interfering with a subject's sleep. The protocol may also cause the stimulation amplitude to gradually ramp down after an interval that is defined to end an hour or so prior to when the subject is expected to wake up to deter early awaking. If the system is provided with, or is in communication with, a sensor (e.g. EEG, EKG, strain, or accelerometer sensor), and a processor is provided in a sensing module 55 that is able to algorithmically assess arousal level, sleep, or sleep stage based upon sensed data, then TENS stimulation may only occur when evaluation of sensed data meet a selected criterion. For example, stimulation may only be provided during certain sleep/arousal stages or only when the subject is experiencing restful sleep (e.g., leg movement measures remain below a selected threshold). A stimulation protocol that is defined for providing stimulation for longer periods (e.g. several hours at night) can use different stimulation signals than those used during a 30-minute therapy session. For example, the amplitude and/or pulse duration of the signals may be lower those used for 30-minute sessions.

Patient Safety Across Stimulation Type.

Stimulation signal amplitudes may be lower when the neurostimulator 50 uses needle electrodes rather than TENS electrodes. Accordingly, in order to provide for patient safety and deter unwanted or unintended stimulation signals from being erroneously used, a number of hardware and/or software safeguards can be used. For example, a lead set 24 that is attached to the device by plug 22 uses a lead set or plug for providing TENS stimulation that is different than that which is used to provide percutaneous stimulation, and may even connect differently to the system. Additionally, these two different types of lead sets/plugs can contain circuitry that adjusts the amplitude of the stimulation signal output by the device 50 so that it is appropriate to the therapy being delivered to the patient. The neurostimulator may allow users to toggle the control module 52 to operate in a percutaneous mode or TENS mode. Each mode has a set of one or more stimulation protocol parameters that create stimulation waveforms that are appropriate for the two different types of stimulators (e.g., voltage, current, pulsewidth, or duty cycle). However, for safety or other reasons it may be preferable to use two different lead sets that prevent a user from accidentally providing a stimulation signal that is higher or lower than what is intended. The plug 22, can also communicate, or otherwise operate in conjunction with internal modules of the device to adjust the amplitude, or maximum amplitude that is permitted while the plug is attached to the housing 12. In an additional embodiment two different plug+lead sets can be used, where the plug that is used during TENS stimulation fits a first connector of the system and a different shaped plug fits a second connector of the system. In an additional embodiment an adaptor can be provided for a plug that is used during percutaneous needle stimulation that fits a first connector of the system (and attenuates the stimulation signal by a selected amount) and the plug for the TENS lead set can be attached directly to a connector of the system 10. The lead sets used for percutaneous stimulation may have circuitry that attenuates the strength (e.g., voltage, current, pulse width) of the stimulation signal output from the device 50, while the TENS lead set does not have this additional circuitry. Alternative methods for providing patient safety are disclosed later in this specification.

Figure 6A:
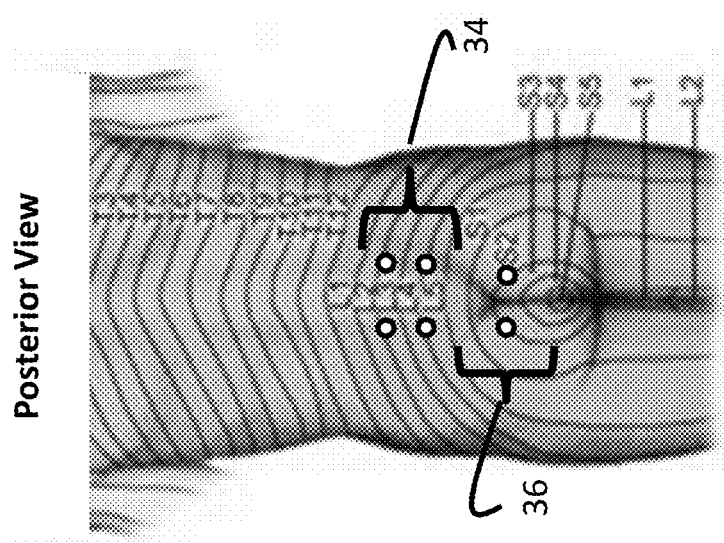
FIG. 6A is a view of target locations for a neurostimulation system applied to a back of a patient for providing transcutaneous stimulation according to an alternative embodiment of the disclosure.

FIG. 6A shows an embodiment in which TENS stimulators are applied to the back of a patient to stimulate either lumbar and/or the combination of lumbar and sacral nerves. Current investigations of sacral stimulation therapy using TENS (e.g. ClinicalTrials.gov Identifier: NCT01940367) instructed subjects to place surface electrodes, 2"×2" in size, over the sacral foramen S2-4, bilaterally, using 2 channels (4 electrodes total). Approximate locations are over posterior superior iliac spine and inferior lateral angle of sacrum. As is shown in FIG. 6A, using TENS electrodes more cephalad to the locations used to stimulate sacral targets 36, such as locations 34 over the lumbar sites L2-L5 can be used instead of, or in addition to, the currently evaluated approach to provide improved therapy. During the provision of therapy, stimulation may be provided using different patterns. For example, stimulation can be sequentially applied to contralateral electrode pairs (at the same level of the spine) rather than concurrently (e.g. L2 left and L2 right, then L4 left and L4 right), or ipsilaterally (e.g., L2 and L4 left, then L2 and L4 right), or can be applied to single targets (e.g., L2 left with an electrode placed on the patient's thigh to close the circuit). Additionally, in an embodiment, treatment using the lumbar TENS sites can be used in patients who do not respond to stimulation of other targets such as at sacral target sites.

Patient Compliance

In a trial, or clinic-based, setting the detection of non-compliance may allow for corrective measures and interventions that can ultimately cause therapy to be successful rather than fail. When providing stimulation at home, rather than in a clinic, monitoring and promoting patient compliance can be essential. Especially in more severe cases of OAB, an increased amount of stimulation may be needed in order to obtain therapeutic benefit, rather than 30 minutes once or twice a week. Patient compliance may be a challenge both for TENS, magnetic stimulators (e.g. TMS devices) and for 'implantable' therapies that are powered by, or controlled by, external components of the neurostimulation system. In therapy systems that stimulate targets such as the PTN or SAFN and do not provide for an internal battery in implanted components, the patient must remember to activate an external controller in order to activate the implanted neurostimulator. The provision of a compliance module 200 is important because it is well known that patients can be inaccurate about their actual compliance, and this can be a greater concern for older OAB patients. It may be important for a doctor to be able to accurately assess patient compliance, rather than simply relying on the reported compliance, to determine if a patient is not responding to therapy due to compliance issues or due to other reasons such as lack of a treatment response in a compliant patient. Accurately tracking compliance may also be important in assessing efficacy in clinical trials where subjects are expected to provide self-stimulation outside of a controlled setting.

In embodiments of the current invention the user/physician programmer works with an implantable neurostimulator. Examples include the Stimguard or Bluewind systems which are undergoing clinical trials and another is eTENS, which we have previously described in application Ser. No. 14/553,427. It is not useful for a doctor to assess compliance of patients self-treating themselves at home during a clinic visit, since patient compliance reports may not be accurate. Existing TENS systems do not allow a doctor to assess patient compliance outside of their clinic visits, such as by using remote monitoring. Accordingly, the system 8 is provided with functional modules that address current limitations related to managing and augmenting patient compliance.

In an embodiment, a compliance module 200 (see FIG. 8) is realized within at least one component of the system 8 such as the neurostimulator 50, and/or the user/physician programmer 70, and/or the management computer 71, and performs operations related to patient compliance. As will be disclosed, the compliance module 200 can operate, and work with the other modules of the neurostimulation system, to manage, monitor, track, promote, summarize, analyze, display, report, transmit, process, and alert to, aspects of patient compliance. Although existing TENS units can monitor patient usage in the form of total treatment time provided (e.g., in total hours) since the reset of a counter, there is no provision for other characteristics related to patient compliance. The compliance module 200 stores a detailed historical record of patient use and displays the actual usage, including metrics that reflect usage on a per-hour, per-day, or per-week basis. Some additional features and advantages of the compliance module 200 of the present invention, that address limitations of the use-counters of existing TENS devices are now further disclosed.

The compliance module 200 can alert a patient 6 by operating the user interface module 80 or communication module 68 to provide an alert signal to a patient about a scheduled therapy interval. The alert signal may be communicated from a device of the system 8 to a patient's smartphone or may be realized as a sonic or visual alert provided by the user/physician programmer 70. The alerts may be used to alert the patient (or physician or other intended recipient) to compliance failures when a compliance criterion is not met. A compliance failure may occur if a patient fails to provide stimulation for one or more scheduled therapy sessions within a defined time interval (e.g. within 24 hours after stimulation was supposed to occur), or in response to failing to meet other compliance conditions as will be disclosed. The compliance module 200 can also alert a user of an upcoming scheduled stimulation session/time.

In embodiments, compliance module functions can be realized, at least in part, by a customized application operated on a patient's smartphone. For example, an application miming on a processor of a smartphone according to instructions provided on computer readable media can cause an alert signal to be issued to a patient or caregiver to notify about a scheduled therapy. In order to promote compliance, the alert can be set to occur prior to a scheduled therapy time (as a prompt), or at a selected time after the therapy if the patient did not provide correct or insufficient therapy (as a reminder), or both.

A smartphone-based compliance application can be considered as one alternative embodiment of the compliance module 200, and may be operated independently or in combination with the compliance module 200 of the system. A smartphone compliance application that does not communicate and cooperate with the compliance module 200 of the neurostimulator may be limited and may simply serve as a reminder-system, since while the application provides reminders to a patient it may not be able to monitor and/or determine if therapy is provided by the system 8. However, an integrated system is preferred and wireless communication between the neurostimulator 50 and a patient's smartphone can occur via radiofrequency, Bluetooth, sonic, infrared, WIFI, or other one-way or two-way communication protocol.

Figure 7B:
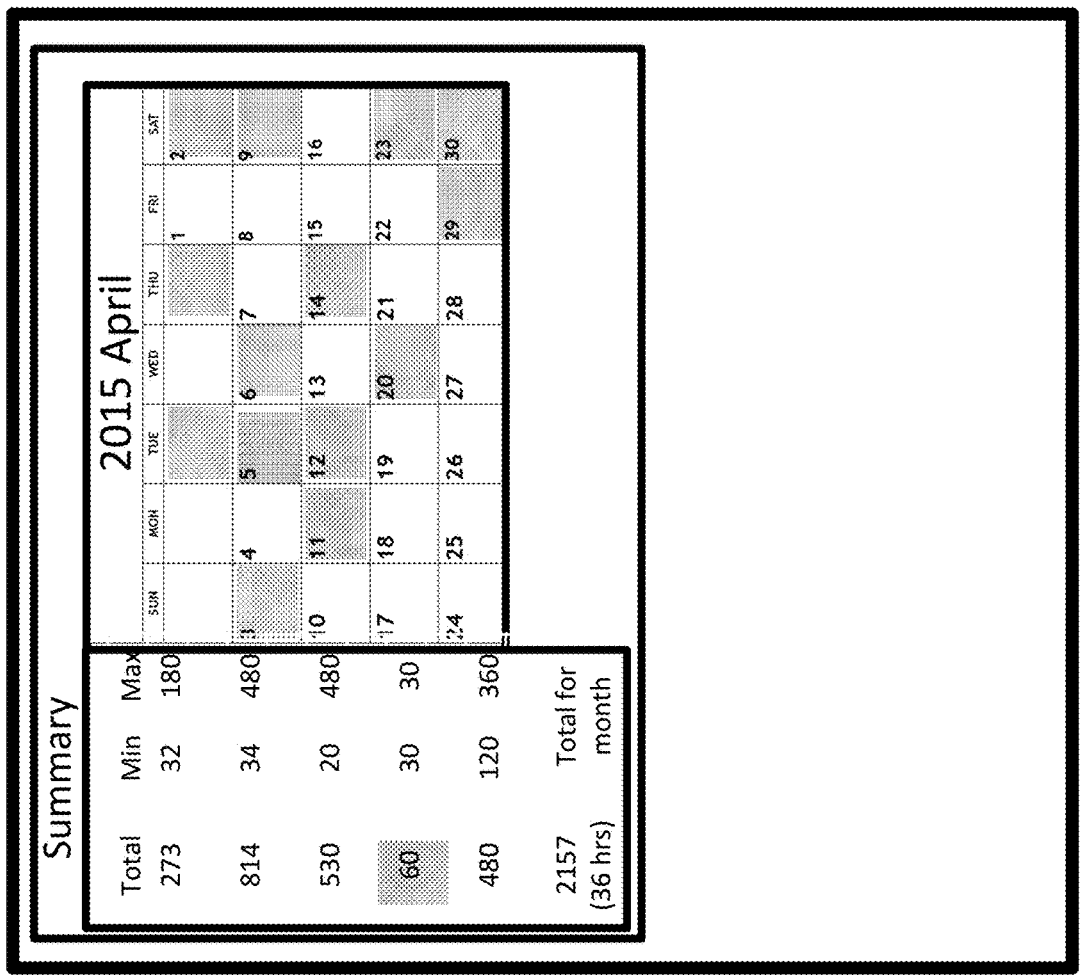
FIGS. 7A and 7B show two displays related to patient compliance that can be provided by a compliance module of a neurostimulator system.
Figure 7A:
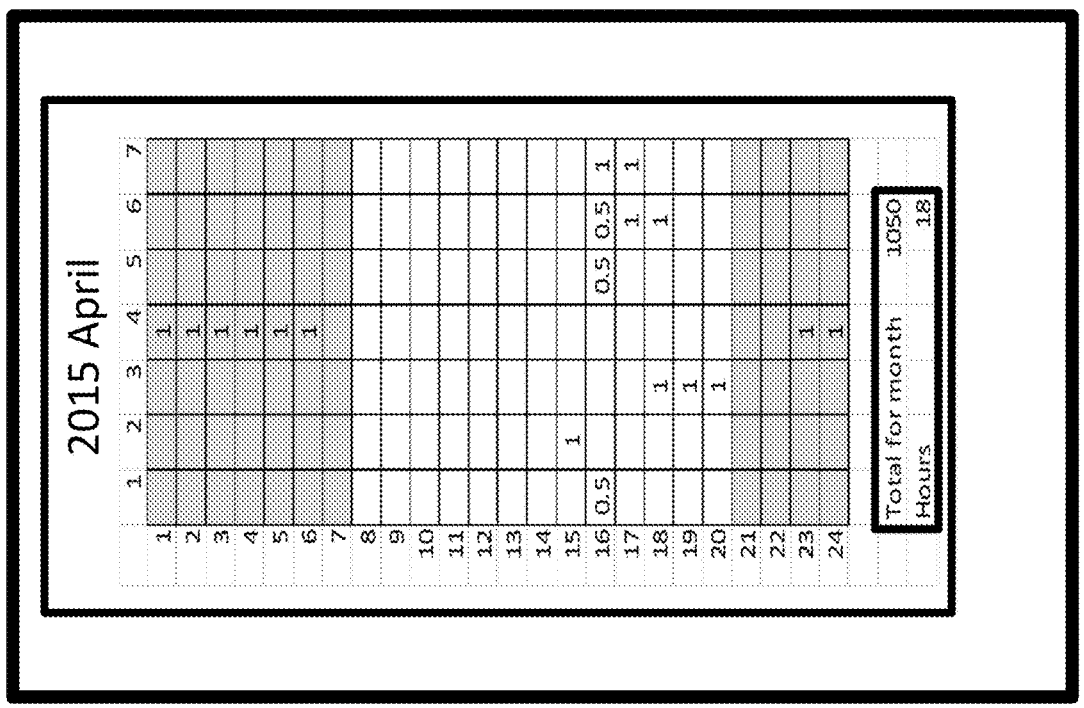

FIGS. 7A and 7B show two embodiments of compliance screens that can be provided using information generated by, stored, and operated upon by the compliance module 200. FIG. 7A shows a monthly calendar summary view that summarizes both total therapy per week (in minutes) as well as maximum and minimum durations during which individual therapy sessions occurred. The weekly summary statistics are presented in the therapy summary table on the left-hand side of the screen and include total minutes per week, and the minimum and maximum durations for stimulation sessions provided by the system. Also shown in the bottom row of summary statistics is the integrated time across the entire month, which provides a simple patient compliance measure that shows the total treatment time in hours.

There may be different compliance criteria that must be met for the patient to be considered compliant. For example, a monthly therapy compliance criterion may require that at least 2000 minutes of therapy be provided each month. In this example, the patient has met this criterion successfully (i.e. the patient provided 2157 minutes). Alternatively, a weekly therapy compliance criterion may include providing therapy for at least 120 minutes per week. In this case the patient did not meet this therapy compliance criterion in the $3^{rd}$ full week of April where only 60 minutes of therapy were provided. The compliance failure is reported by a shaded value of "60". A therapy criterion can also exist for a time of day, for example a therapy criterion can require a patient to have at least 3 sleep/night sessions of at least 5 hours each week. Therapy compliance criteria as well as contingent actions which occur if one or more criteria are not met can be selected or adjusted by a user, such as a doctor, caretaker, or patient. A password or other permission schema may be used to restrict access to the operations that allow therapy criteria to be adjusted. Additionally, summary statistics can be calculated and displayed by the compliance module 200 that compare the times and durations a patient provided therapy in relation to pre-set treatment schedules. Therapy compliance criteria can be set for minimum/maximum durations, stimulation amplitudes to be used during treatment, and other characteristics.

FIG. 7B is an alternative view of compliance data monitored, stored, analyzed, summarized and displayed by the compliance module 200 which in this example is shown in a calculated weekly view that also shows the hours of each day of the week that therapy was provided. This view can be obtained by a patient (or doctor) by clicking on any week of the calendar shown in FIG. 7A. Night time data (times when the patient is typically sleeping or as determined by analysis of sensed data such as accelerometer data) can be shaded in one color (e.g., grey boxes), and times when the patient is typically awake can be shaded in a selected color such as white.

Either an implanted neurostimulator or an associated external device that provides power/data signals to control therapy can operate a compliance module 200 to generate and log in the device memory a record of operation. It can further compare information regarding usage to compliance criteria to monitor, assess, transmit, promote, alert to, generate and store a log related to, and display compliance or lack of compliance.

The compliance module 200 can monitor and assess a patient's compliance using various compliance criteria, such as the following:

A daily compliance criterion can include a minimum amount of time per day during which therapy must be provided, for example, at least 30 minutes of approximately continuous stimulation, using a minimum amplitude, on a given day.

A nightly compliance criterion can include a minimum amount of time per night during which therapy must be provided, for example, at least 6 hours on a given night.

A weekly compliance criterion can include a minimum amount of time per week during which therapy must be provided, for example, at least 20 hours per week. Additionally, a weekly compliance criterion can include meeting the daily compliance criterion for at least a selected number of days (such as 3 days per week). A weekly compliance criterion can also require for example, at least 3 days of therapy and further require that a day with no-therapy occurs between each day of therapy. A weekly compliance criterion may also require that the daily compliance criterion is met at least twice over the course of a week and the nighttime criterion is met at least once.

A monthly compliance criterion can include a minimum amount of time during the month during which therapy must be provided, and may include additional compliance criteria such as that at least 2 of the 4 weeks are determined to meet compliance criteria.

Compliance criteria can relate to stimulation protocols rather than number of treatments or total therapy duration. For example, a compliance criterion may be managed by a user to adjust the criteria to require such characteristics as stimulating both legs instead of one leg at least once a week. A compliance criterion can require a patient fill out an electronic bladder diary, a quality of life survey, or provide responses to Likert-type scales that are provided by a device of the system 8 according to a schedule such as at least once every two weeks. A compliance criterion can be managed to require that more frequent stimulations such as every other day are provided at the beginning of therapy and after an interval such as one month, can then be decreased to require a less frequent schedule of stimulation sessions to be provided by the user. Compliance criteria can also relate to users who take medication and can be calculated based upon user input queries about whether they have taken their medication. Accordingly, compliance criteria which include both stimulation and medication criteria can be operated upon by the system.

In an embodiment, the system 10 is programmed with a stimulation program that is more frequent in the first days or weeks of therapy. This becomes less frequent only if the patient reports benefit. This can be reported by patient input such as patient responses to survey items provided by the user interface module 80. Additionally, the system may prompt the patient to answer questions about symptoms (under control of the patient survey module 61) and begin to decrement the frequency of the treatments after a minimum interval (e.g. 4 weeks) only if the patient rating data (e.g. selection of a value for a Likert scale) or patient answers to survey data that are provided in response surveys presented to the user are operated upon by the system 8 and show improvement (e.g. QOL scores improve over a selected amount). The patient alerting and compliance module 200 parameter values can then be adjusted according to this less frequent therapy. The SAFN may be more sensitive to, and offer an additional mechanism for, stimulation intended to modulate bladder activity. In the unlikely event that stimulation (e.g., SAFN or combination of SAFN and PTN stimulation) produces an unwanted side effect (e.g., causes or approaches urinary retention as reflected by patient response to certain survey questions or analysis of digital bladder diary data), then, in an embodiment, the compliance module will reduce the stimulation parameters (or prompt the user to do so) to permit titration of therapy. Adjustment of stimulation parameters may involve adjustment in one or multiple nerve stimulation targets.

In addition, compliance may relate to enforcement of compliance restrictions. For example, the compliance module may dictate that a patient cannot provide therapy more than a certain number of times per-day or other selected interval. The restriction can be assessed by comparing usage to interval rules that can limit stimulation for a selected interval. Further the restriction can be defined as a combination of time, number of stimulations, and treatment strength which is accomplished using an interval rule type referred to as an interval-strength rule. For example, a patient who uses larger stimulation amplitudes may be restricted to a lower number of maximum treatments within a selected time interval. In an embodiment, a sum of treatment times can be weighted by the stimulation strength. Unlike medication, where a patient ingests a certain number of pills over the course of a defined interval and must obtain refills at the end of the interval, there may be no evidence of patient over or under usage of electrical therapy in the absence of the compliance module 200. Accordingly, without a compliance module, detecting and deterring the occurrence of either over or under stimulation is difficult to accomplish.

The compliance module 200 allows doctors or patients to adjust how compliance is managed by selecting what the compliance criteria are for an individual as well as how and when the therapy schedule may change over time. Both usage and compliance can be tracked over time, and this can be displayed to a user or remotely to a doctor. The promotion of compliance can occur with setting reminder alerts to occur before a scheduled stimulation session, or after the time when this was scheduled if it did not occur, etc. Reports related to usage and compliance can be stored and transmitted over computer networks to allow for remote patient monitoring and management. The various features should improve patient compliance.

In the case of patient non-compliance various operations may occur according to the compliance module 200 in conjunction with the other system components and methods of the invention. For example, failure to meet a monthly compliance criterion for X out of Y months, or for a selected number of sequential months, can result in the compliance module 200 causing an alerting module 204 to cause a signal to be provided to the patient or medical care provider. Alternatively, a compliance module 200 algorithm may cause the neurostimulator to deny/restrict stimulation until it receives a reset signal from a remote physician computer 70'.

Additionally, the patient prescription status flag may be changed to inactive in the remote physician computer 70'. In other words, if a patient is not compliant and then wishes to use a neurostimulator then they may first have to meet with their doctor to discuss the non-compliance and have their device re-enabled. The doctor may need to submit the compliance record of the patient and evidence of a patient visit in order to obtain an approval from an insurance carrier to re-activate a neurostimulator of a patient. This may further be tied to requiring a new prescription be written and prescription status updated in the system.

The compliance module may operate to provide different alerting schemes for treatment of different disorders. For example, if the TENS system is used for providing transcranial direct or alternating stimulation (i.e. tDCS or tACS) in the treatment of depression or anxiety, failure to adhere to a treatment schedule may result in the system communicating with a computer 70,70' to alert a doctor or caregiver that a patient is not complying with a therapy regimen. Alternatively, if the tDCS/tACS is used to provide cognitive enhancement, then no such notification may occur. In an embodiment, compliance operations rely upon timing circuitry, such as a real-time clock, to calculate times and dates related to when and for how long stimulation was provided.

In an embodiment, the compliance module 200 is configured to generate reports based upon processing of compliance data to generate compliance summary data and usage date to generate usage statistics. The reports may be transmitted to a clinic or remote computer 71 or are generated by the remote computer using compliance or usage data. The system 8 generates reports according to a schedule or due to doctor request or due to periodic processing of the compliance data and detection of non-compliance. Non compliance can be detected when the compliance summary data are compared to, and fail to meet compliance criteria. The compliance statistics over time are displayed as trend graphs which allow the tracking of compliance and show periods and rates of compliance as therapy progresses. When presented as summary statistics the compliance may be reported for the last week, month, and since beginning of treatment (e.g. 100% compliant for the last week, 90% for the last month, and 95% since the beginning of therapy). A report of usage can include such statistics as number of weeks since start of therapy, total stimulation sessions, average number of stimulation sessions scheduled or provided each week, average length of stimulation sessions, average strength of stimulation sessions. A table can also be generated where the date, time, duration, and stimulation settings for each session are listed. When trend data is presented for patient input data such as urge scores, this may be presented separately for day and night as defined by user (e.g, day 8 a.m. to 9 p.m and night 9 p.m. to 8 am). When a user first operates the device 50 it may present the user with a set of treatment customization items that allow the user to adjust the schedules for providing patient input or treatment. For example, how many times a week survey questions should be asked as well as what time these should occur.

The payments and permissions module 202 can communicate with a remote management (e.g., a computer of an insurance company) or physician computer 70,70' to ensure that a patient is in good standing before enabling the provision of therapy. For example, a remote management or physician computer may assess whether 1. The patient has met various compliance criteria; 2. The patient has an active prescription for the therapy from their doctor which has an associated "active" status flag that is set in the neurostimulator; 3. Insurance is in good standing; 4. The account associated with the neurostimulator has not been flagged for any reason, such as a) doctor has failed to meet with the patient for too long a time since prior visit b) the neurostimulator is scheduled for calibration/maintenance/replacement or c) the neurostimulator has sent flags related to device operation, faults, failure to meet calibration and/or self-test routines etc.

Figure 8:
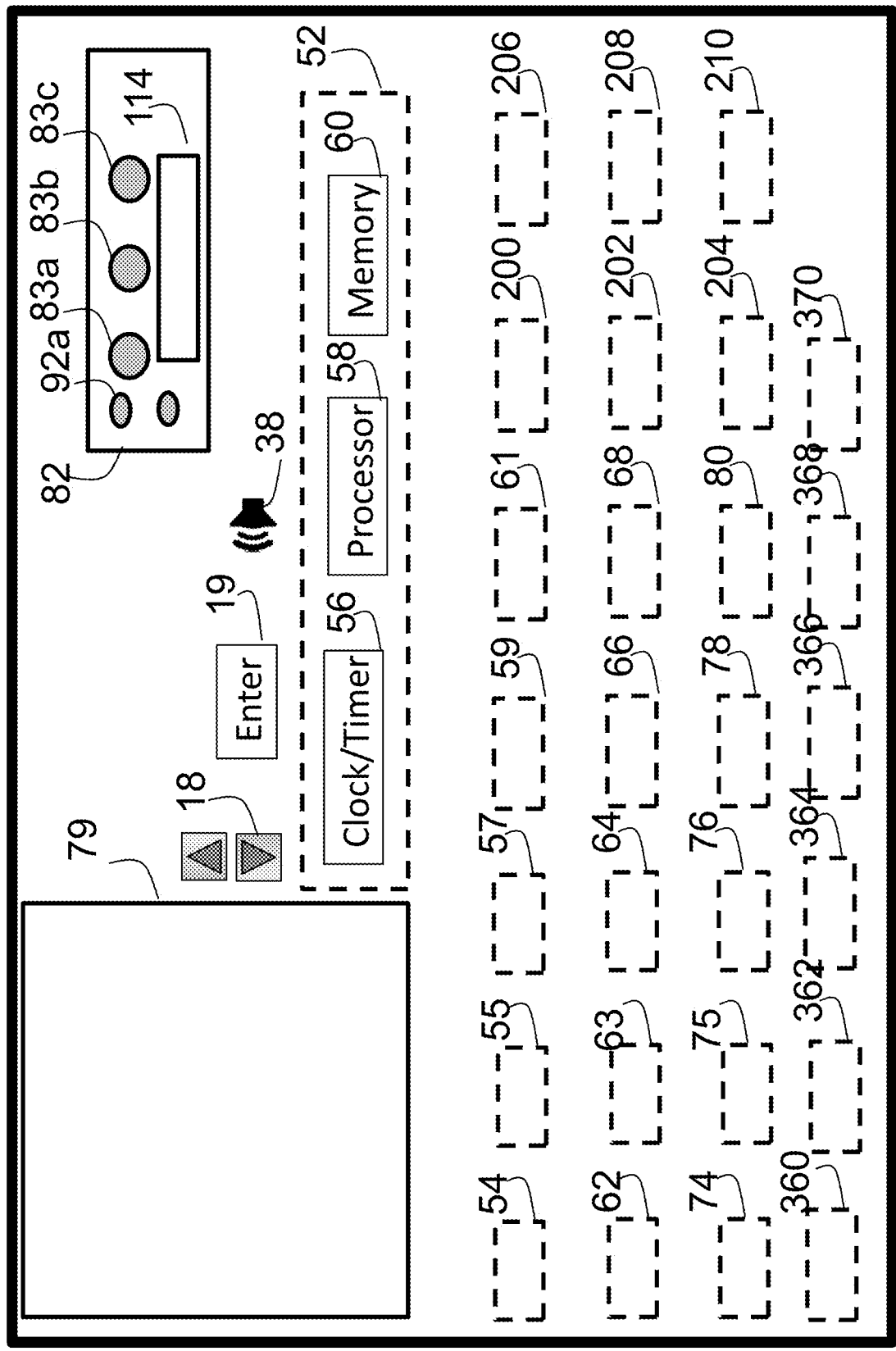
FIG. 8 is a schematic diagram of a neurostimulator system and functional modules which may be used to realize embodiments of the current invention including the provision of tissue stimulation.

FIG. 8 shows a neurostimulator device 50 that can be used to realize the methods and systems of the current invention. The neurostimulator 50 is illustrated with modules and components which may be included, omitted, or modified in various embodiments. The modules provide functionality to the neurostimulator and, while shown discretely, may share software and hardware components with each other. Further, each of the modules may be realized within the neurostimulator housing, outside of the housing, or both (i.e. in a distributed manner). Modules may be realized jointly between the neurostimulator 50 and an external device such as a user/physician programmer 70 and can be redundantly provided within different components of the neurostimulation system. For example, an alerting module 204 may be realized within an implantable neurostimulator, an external neurostimulator, a user/physician programmer, and/or a remote management computer (or a computer network of which it is a part).

The device 50 comprises a control module 52 with circuitry for controlling the various other modules of a neurostimulation system 8. For example, under its direction, the stimulation module 54 and sensing module 55 can be controlled according to user input commands and/or treatment protocols and parameters stored in the protocols and parameters module 66. Treatment protocols can include stimulation protocols, sensing protocols, alerting protocols and evaluation protocols. A non-transitory computer-readable medium is provided in the control module that is configured for storing one or more instructions configured to be executed as part of a treatment protocol by at least one processor of the system, which can be at least one processor of an electrical stimulation device 50 or a user/physician controller 70, or a remote physician computer 70' that communicates over the internet/intranet with rest of the system. These protocols may enable the control module 52 of the device 50 to responsively adjust its operation in relation to, for example, the evaluation of sensed data (e.g. accelerometer data) or detection of defined events as provided by the sensing module 55, patient input data managed by the user interface module 80, time intervals assessed by the control module 52, and other triggers that can cause the selection, provision, and adjustment of therapy as defined by the parameter values and algorithms related to a particular treatment protocol. The device 50 can also simply provide stimulation in response to user input when operated by a user.

The control module 52 has a timing module 56 including a real-time clock and a timer, a processing module 58 including at least one processor for operating software, and processing information and parameter settings that are stored in memory module 60 and which allow for control of device 50 operation. The real-time clock can be used to calculate dates and time to provide event logging and to provide operations related to the compliance module 200. The current date and time can be compared to the date and time of the last stimulation that was provided and the patient can be alerted if a selected amount of time has passed indicating that a treatment is due or has been missed. The time and date can also be used to define and/or realize interval rules which determine, for example, the minimum interval that must occur between subsequent stimulation periods. The date and time can also be used by the payments and permission module 202 to determine if the device is still operating within an interval allowed in relation to payment. The stimulation module 54 can control at least one waveform generator/signal processor such as simulation module 62 that contains circuitry for generating pulses or arbitrary waveforms for output including alternating current (AC) and/or direct current (DC) signals to be used by one or more electrical, magnetic, optical, sonic, ultrasonic or other types of stimulus transducers.

The sensing module 55, may be realized as part of the AD/DA module 64 when AD/DA circuitry (including AC-to-DC, DC-to-AC, and DC-to-DC converters, and allows for both signal generation and acquisition. The sensing module 55 contains circuitry and protocols for conditioning and analyzing sensed data and can also for providing power to, and/or communicating with, various sensors including, for example, position, acceleration, electrical, electromyographic (EMG), electroneurographic, pressure, optical, sonic, and other sensors that may be used by the system. The processing module 58 enables the assessment of sensed data and can provide detection of events that are defined to cause delivery or adjustment of stimulation. Responsive stimulation may occur in a closed loop manner, via rules or control laws, or may cause information (information about the sensed data) or signals (a flashing light) to be presented to a user of the device 50, such as by an external patient device 72 or physician programmer 70, to prompt provision or adjustment of therapy. The processing module 58 may be configured to store data in memory 60 such as historical sensed data records to track patient data, or assessment of sensed data along with usage and compliance data.

An AD/DA module 64 allows for conversion of input and output signals as well as amplification, digital signal processing, filtering, conditioning, and also contains safety and regulation circuitry to ensure patient and device safety. The AD/DA module 64 may also contain circuitry for multiplexing signals across different sensors or stimulators, and can contain switches and controllers for routing and controlling electronics of the system.

The apparatus 50 also includes a communication module 68 for providing wired and/or wireless communication with other system components (e.g. RFID identification to communicate between system components) such as a user/physician programmer 70 or management computer 71. The communication module 68 can communicate with a computer at remote medical facility 70' (to allow data communication and programming to occur remotely) either directly or by way of the user/physician programmer 70. The communication module 68 can provide signals to transceivers which provide one-way or two-way communication of wireless power and/or data signals to implantable components such as neurostimulators. All wired or wireless communication can be realized at least partially using the internet, or a local area network. Communication may also include means for magnetic, radiofrequency (RF), optical, sonic, and/or other modes of data and power communication with other devices. The communication module 68 may include circuitry, hardware, and protocols for providing WiFi, Bluetooth, cellular, magnetic, magnetic inductance, microwave, RF, electrical, optical, sonic, RFID, or other types of communication using communication/interface ports 82, 144. For example, the ports 82, 144 may connect to a system component which provides for wireless communication of data or power signals.

The communication module 68 is configured for use with USB connectors (e.g. 83c) and the like which may be provided as part of a user interface panel 82. The communication module 68 of the device 50, as well as communication circuitry may operate to send or receive signals using near field, far field, induction, magnetic resonant induction components, coils (e.g. an inductive coil assembly for powering an implantable device), antennae, and/or rectennae, optical sensors and stimulators, sonic stimulators and sensors, etc. This allows for successful communication of identification, data or power signals between any external and internal components of a particular embodiment of the invention. The apparatus 50 also has a power supply/recharge module 74 which can include components such as a battery, AC and DC converters, diodes that function to rectify wireless power signals harnessed by rectennae and circuitry related to the conversion or provision of power which may be related to harvesting or transmission of wireless signals, and can include a power cord for connecting to a wired power source through at least one of the communication/interface ports of panel 82.

The interface ports 83 may be connected to communicate with and/or power various sensors, such as sensors that are configured to measure bladder activity, bladder pressure, bladder fullness, foot twitch, or other characteristic related to a condition or disorder being treated. In an embodiment, urodynamic measurements can be assessed before and after stimulation to determine the effectiveness of a given set of stimulation parameters.

A signal routing module 63 provides components and switches that operate to route signals between components and modules of at least one neurostimulator 50. For example, when a TENS protocol is selected the module 63 may route the stimulation signals to a first connector 22 on the housing of the device 50, while when a percutaneous signal is used then this is routed to a second connector of the device 50. Signal routing may also be used when two or more stimulation targets are stimulated to route the signals to the appropriate set of needle electrodes or TENS stimulators. Signal routing may also be used to send signals to a subset of TENS electrodes.

The I/O interface module 75 can contain circuitry and protocols for routing signals and controlling communication related to various input and output ports such as USB or other ports and can further contain safety circuitry and regulators that protect the patient and device 50 from other devices that may be connected to the neurostimulator 50.

The communication module 68 can cooperate with the user interface module 80 which contains hardware and software for presenting information to a user (e.g. patient or physician) and obtaining information/input from the user. Although the device 50 may communicate with a physician or patient programmer 70, or external patient device 72, such as may be realized by a specialized device, smartphone, tablet computer or wearable device, the device 50 may also have at least one signaling module 78 (which can be part of the alerting module 204) with related circuitry and control a display 79 for presenting visual data in both text and graphical format. This may also be used to present a user with visual alarms related to the provision of therapy and/or to operate a speaker 38 for presenting auditory signals such as instructions to patients related to the therapy (e.g., an instruction may inform a patient that a TENS pad may need to be re-applied or replaced because the impedance value is too high). The signaling module 78 can have a Bluetooth enabled sound system that communicates with a speaker 38, or sound transducer such as a hearing aid by way of the communication module 68. The device 50 can also contain patient interface module 80 that permits operation of, and includes, controls such as a keyboard, microphone, nobs, switches, etc. to allow a user to provide input. Input can be confirmed, for example, by an "enter" button 19. The interface module may also provide for a menu guided system that allows for adjustment of device operation. It is obvious that various modules such as modules 78, 79, and 80 can also be realized within the physician or patient programmer 70,70'.

In an embodiment, the device 50 or user interface module 80 is configured with an algorithm that operates according to rules or an artificial intelligence (AI) program that is operated upon by the processor 58 that collaborates with the user interface module 80 to verbally instruct the user on how to set-up, adjust, and use the stimulator. For example, the system instructs a user to put the device on their leg and then delays further instruction until the expiration of an interval or until the impedance circuit indicates the device 50 is acceptably connected to the patient's skin. If the impedance value is not acceptable then the device provides additional instructions to the user. The device also is programmed with an option to communicate with a voice service (e.g., Alexa) to allow interaction with the user via voice prompts as well as sensors on the device 50 such as impedance and accelerometer sensors. The AI program of the interface module 80 is further configured with algorithms to assist with determining treatment characteristics such as selecting stimulation parameters that are suitable and comfortable for the user, and also providing instructions and answers in response to questions posed by the user.

In an embodiment, the system 8 incorporate or is adapted for use by electrostimulation devices, designed to treat symptoms of diseases and disorders such as incontinence by stimulating muscles (and/or nerves) in the pelvic area. For example, muscle stimulators serve to provide exercise and feedback to the receptors and muscles of pelvic area of users suffering from incontinence. In embodiments, the system is also adapted to control or communicate with devices that stimulate the pudendal nerve to contract the external urethral sphincter muscles, or other devices that serve to provide stimulation inside or outside of the body to stimulate muscles to assist with symptoms such as incontinence.

Both the control module 52 and the waveform generator module 62 may be configured with safety hardware and software routines, and can operate in combination with calibration routines of a calibration module 61 to calibrate the apparatus 50 and to ensure proper functioning In embodiments, the control module 52 allows stimulation programs to be implemented according to protocols stored in the device memory and according parameters that can be adjusted by a user's manual input obtained by the patient interface module 80. The safety routines of the safety module 208 may limit the adjustments made by a user to ranges that are safe.

The interface port panel 82 allows for connection to various system components. The device 50 may use at least a first stimulator conduit 84, a second stimulator conduit 86, to communicate signals to a first stimulator 28b and second stimulator 88. Conduits can comprise single or multi-stranded electrically conductive, insulated electrode lead wires. The first conduit 84 has a first end connector that may contain a plug that electrically couples to a first stimulator interface port 83a of the interface 82. When the device 50 is used to provide stimulation using non-TENS modalities the third stimulator interface port 83c may be configured to be connected to a TMS device to control the provision of magnetic stimulation as part of the system and method of the current invention.

Alternatively, the wired interface port 83c can allow for connection to sensor components. When the stimulators are TENS electrodes, then these can serve as both stimulator and sensor, typically at different moments in time. Stimulation electrode 88 can serve as sensor when the sensing module (or impedance module) rather than stimulation module is operationally connected to a specific port during a selected period. However, other types of sensors may also be used.

In an embodiment, the interface port panel 82 may only consist of one or two connections that are distributed on the device housing. For example, the neurostimulator 50 can be realized in the form factor shown by neurostimulator 51a and utilizes a transcutaneous electrode pad such as those commonly used to provide TENS, which may have bottom surface that is an adhesive and conductive surface (for attachment to a patient) and a top surface configured with connector 89a which may be realized as an adaptor such as a metallic snap to be connected and disconnected to a connector either on the bottom surface of the housing of the neurostimulator 51a, or to connect to the end of a lead set. The neurostimulator 51a may have a lead set 86 containing a single lead wire for electrically connecting a single needle electrode 28b or TENS electrode 88, to the neurostimulator via connector 22. Alternatively, the lead set 86 can contain multiple lead wires for electrically connecting one or two percutaneous needle electrodes, and a TENS pad to the neurostimulator via connector 22.

The alerting module 204 provides functions related to patient alerting and can include providing alerts using sounds emitted by a speaker 38 or visual alert signals provided by displays 79 or communication signals sent using the communication module 68.

The impedance module 206 operates to promote impedances of the leads used during stimulation are below an acceptable threshold level such as by providing a user with an alert if the impedance data is above this level. This is important for home users because stimulation will not be effective if the TENS pads do not have good contact with the patient's skin. Patients may not be well trained to notice incorrect placement of TENS electrode or the occurrence of bad skin contact.

The patient safety module 208 can provide operations and control hardware related to ensuring patient safety. For example, if the module assesses that a calibration or maintenance date stored in the module has passed it may set a flag and provide a message to a user or may not allow device operation until the flag is reset when the indicated operation is provided. The safety module may also not permit certain operations such as providing patient treatment when the device 50 is connected to a recharging power source.

Payments and Permissions

The payments and permissions module 202 provides for management of device operation. This can include setting what operations and values are permitted to be accessed by a user. Passwords or biological/biometric markers (e.g., EKG or face recognition) may be required to grant access. The module 202 can also allow a user to provide information related to using and purchasing of treatment credits. In an embodiment this includes medical billing information, reimbursement codes, credit card account numbers, user or clinic information, and other information related to payments or treatment credits. For example, submission of current procedural terminology (CPT) codes can allow for appropriate coding of the service with diagnosis using ICD-9 code as determined by the Centers for Medicare and Medicaid Services (CMS). These relate to determination of associated fees for providing stimulation. The reimbursement codes are based upon treatment characteristic such as if SAFN or PTN targets are being stimulated, and if the stimulation protocol being used is for one leg or for both legs. Reimbursement codes used by the system 10 may be country or region specific. Additionally, the payments and permissions can be modified according to region or state. For example, certain states may cover costs related to certain types of stimulation protocols while other states may not and so the operation provided by the system 10 or the type or amount of a charge associated with a particular treatment credit may be adjusted accordingly. Information related to a patient or a patient's insurance may also be used in the processing of the treatment credit information. This can allow the cost for severe or moderate patients, who may need more stimulation sessions, to pay the same amount as patients who need less.

In an embodiment, a neurostimulator 51a is preferably configured to communicate with a computer system 71 which provides a treatment credit purchasing system and also allows for monitoring the status and usage of a neurostimulator. For example, the neurostimulator 51a can communicate with the computer system wirelessly or through an input/output connector 144a which may be realized as a USB connector. Information can also be provided to the neurostimulator 51a using a portable digital storage device such as a USB flash drive. The USB flash drive may allow two way data exchange between the computer system and the neurostimulator or may only be used to update information in the neurostimulator.

If wireless communication is not available near a user of a neurostimulator, a user is not technically savvy, or if there are other reasons (e.g. regulatory) why a neurostimulator may not be provided with wireless connectivity, it may be advantageous to provide a physical key, such as a USB memory key. In an embodiment, the key is programmed to be read by the neurostimulator and to provide a selected number of treatment credits, or to allow the neurostimulator to operate for a selected amount of time or until a specific date. The USB memory key may fit into an I/O port 144 of the neurostimulator, which can then read the USB key and update its internal parameters. In an embodiment the USB key may be required to be attached to the neurostimulator during use. The USB key and the neurostimulator may be matched 1-to-1, via the payments and permission module 202 which may be programmed to only read a USB key having a particular ID code: the USB key can only be used with a particular neurostimulator. A patient can receive a USB key in the mail and can mail back a previously sent USB key. Alternatively, a patient can be mailed a code that can be manually input by a patient to re-activate the neurostimulator for a duration or to provide additional treatment credits, according to a prescription or otherwise. Alternatively, a smartphone running specialized application software can communicate with a remote computer 71 and the neurostimulator 51a to manage treatment credits. This allows the neurostimulator to remain relatively simple, and the circuitry and hardware of the smartphone may be relied upon.

In embodiments the neurostimulator 51a includes a control system 52 with a microcontroller/processor 58 which operates the payments and permission module 202 to manage and store information relating to payment credit status, historical usage, compliance data, and other parameter values of the neurostimulator 51a. The payment status and usage information may be transferred between the neurostimulator 51a and the computer system 71 when the neurostimulator is in communication with the computer system 71. The control system 52 monitors the value of a treatment credit counter which indicates a treatment credit value associated with the number of treatment credits that are available.

A treatment credit can correspond to allowing for various types of therapy provision. For example, a treatment credit can be set equal to a treatment session of, for example, 30 minutes of continuous stimulation, and after a treatment session is completed, the number of available treatment credits is decreased by 1. Further, a therapy session may have to be interrupted or paused. Accordingly, in an embodiment a treatment session can have a minimum duration defined before a treatment credit is used, such as 15 minutes. The treatment sessions can also be defined as a selected interval of total provided stimulation (e.g. 30 minutes). The interval may be allowed to occur within a selected interval (2 hours). This can allow for 1 or more interruptions or pauses to occur during treatment. If there are no more treatment credits available to the neurostimulator 51a, then the processor 58 operates in a manner that prevents the neurostimulator 51a from providing a session of treatment. For example, this can be done by preventing operation of the stimulation module 54 and also presenting a user with a message or alert using the alerting module 204. In this case, additional treatment credits can be purchased and uploaded into the neurostimulator 51a to allow for subsequent treatment sessions to occur.

In an embodiment the compliance module 200 works with the payment and permission module 202 to realize gamification of therapy. For example, if a patient is compliant by providing patient input about their symptoms or providing therapy in response to a defined treatment schedule then a treatment point value is increased. and if they are not compliant according to one or more defined compliance rules, then a treatment point value is decreased. Treatment points can be defined to contribute to different treatment point categories, such as compliance, length of treatment, rate of entering patient input data. For example, if a patient typically provides self-stimulation within 1 hour of their scheduled time then that could be 2 points. If the treatment occurs on the right day, but many hours after the scheduled time, then they can get 1 point. If they skip the treatment 1 point is subtracted, and if they skip 2 sequential treatments 2 points are subtracted. Points can also be given for answering questions, such as those prompted by the device in the morning which questions the user about nighttime voids or leaks. The set of treatment points are calculated upon to generate ratings or user status levels such as "Excellent patient", "Very good patient", "Good patient", "Late Patient", "Uncooperative Patient", etc or are used to calculate one or more scores. The treatment points can be assessed over an interval such as a day, week, or month. As with gamification schemes, selected scores can result in winning prizes or awards which may be purely symbolic. Alternatively, prizes or awards for certain treatment point categories can be used to further incentivize patients with economic incentive. For example, points can result in "winning" a free treatment credit or a discount code which can be used to order supplies such as replacement TENS electrodes. The treatment game rewards may be managed by the payment and permission module 202, or otherwise. In an embodiment, the discount is applied automatically to a shopping cart feature of module 364 of the software application operated in the user device.

If the neurostimulator 51a is not used during an interval defined for treatment, or is used less than a minimum selected amount (e.g. 15 minutes) then the payment and permission module 202 of the neurostimulator 51a can automatically increase the stimulation-credit value by 1 to the prior value. When multiple patients are treated by the neurostimulator, the physician can enter the patient ID into either a physician computer or the neurostimulator so that a particular patient is associated with the stimulation session.

In an embodiment, the neurostimulator is permitted to provide stimulation therapy-sessions while the treatment credit value is zero or negative, as long as the stimulation credit value of the neurostimulator is above a defined payment threshold such as −50 units. Further, a treatment credit rule can be implemented by the payments and permissions module 202 of the neurostimulator 51a, whereby the negative value reflecting a treatment credit deficit must have lasted less than a selected interval such as 90 days. This feature can be important for some clinical practices since a clinic may not be paid or reimbursed for a treatment session until several weeks or months after a treatment is provided to a patient. In this manner, a clinic does not have to pay in advance for credits that may not be used for some indeterminate time in the future.

For various disorders or treatment regimens, a session-based stimulation paradigm may not provide an appropriate unit of therapy. For some patients and disorders more than one session will occur during a particular day. For example, when the neurostimulator 51a is used for providing treatment related to pain, migraine, headache, sleep apnea, etc., rather than for treatment of overactive bladder, then several treatment sessions can be needed to relieve symptoms. The patient and/or clinic should not be required to use multiple treatment credits. If a treatment credit allows providing only a single session then problems will occur in some patients worry about cost. Certain patients will use less treatment credits rather than providing themselves with additional needed therapy.

In embodiments each treatment credit enables stimulation therapy to be provided multiple times across a selected interval such as a single day, week, or other defined period. Further, the neurostimulator payment and permission module 202 is configured so that a maximum number (e.g., 10) of treatment credits can be delivered to a neurostimulator 51a at a particular time. This provides for an advantage that a patient must contact a doctor or service provider after a period of, for example, two months. Further, although at least one treatment credit is available, the payment and permission module 202 of the neurostimulator 51a may not allow therapy to be provided in selected circumstances. This may occur if a compliance criterion is not met or, for reasons related to patient safety, a certain number of stimulation sessions, or total stimulation time, may only be allowed to occur within a selected interval such as 1 day.

In an embodiment, the user notification module 360 provides notifications to a user or remote medical personnel using light and sound transducers of the neurostimulator 52a or user/physician programmer 70, or other system component. It communicates with a computer at a remote location 71 such as a doctor computer using wired or wireless communication The web-meeting medical assistance module 362 provides software application, and multimedia hardware (e.g. video camera and microphone of a smartphone miming the treatment application software of the system) which support virtual online meeting capability and also permits a medical professional to view the treatment log of a user to assess treatment history.

The digital shopping cart module 364, allows for in-app purchases using a digital shopping cart and allows for purchasing of treatment credits, subscription fees, ordering of replacement stimulation pads or other payments associated with use of the system. This module also allows for the provision of discount codes and rebates to be applied against payment as may be obtained due to a user achieving selected treatment goals monitored by the compliance or gamification modules.

The video and multimedia module 366 provides users with videos that can be relate to providing the neurostimulation treatment correctly 368.

The gamification module 370 allows for points to be allocated to users scores as a function of compliance or non-compliance or in return for the user performing operations that are conducive to obtaining therapy benefit such as providing longer stimulation sessions than are necessary or watching videos related to positive lifestyle changes they can make to decrease unwanted symptoms of a disorder.

Figure 9:
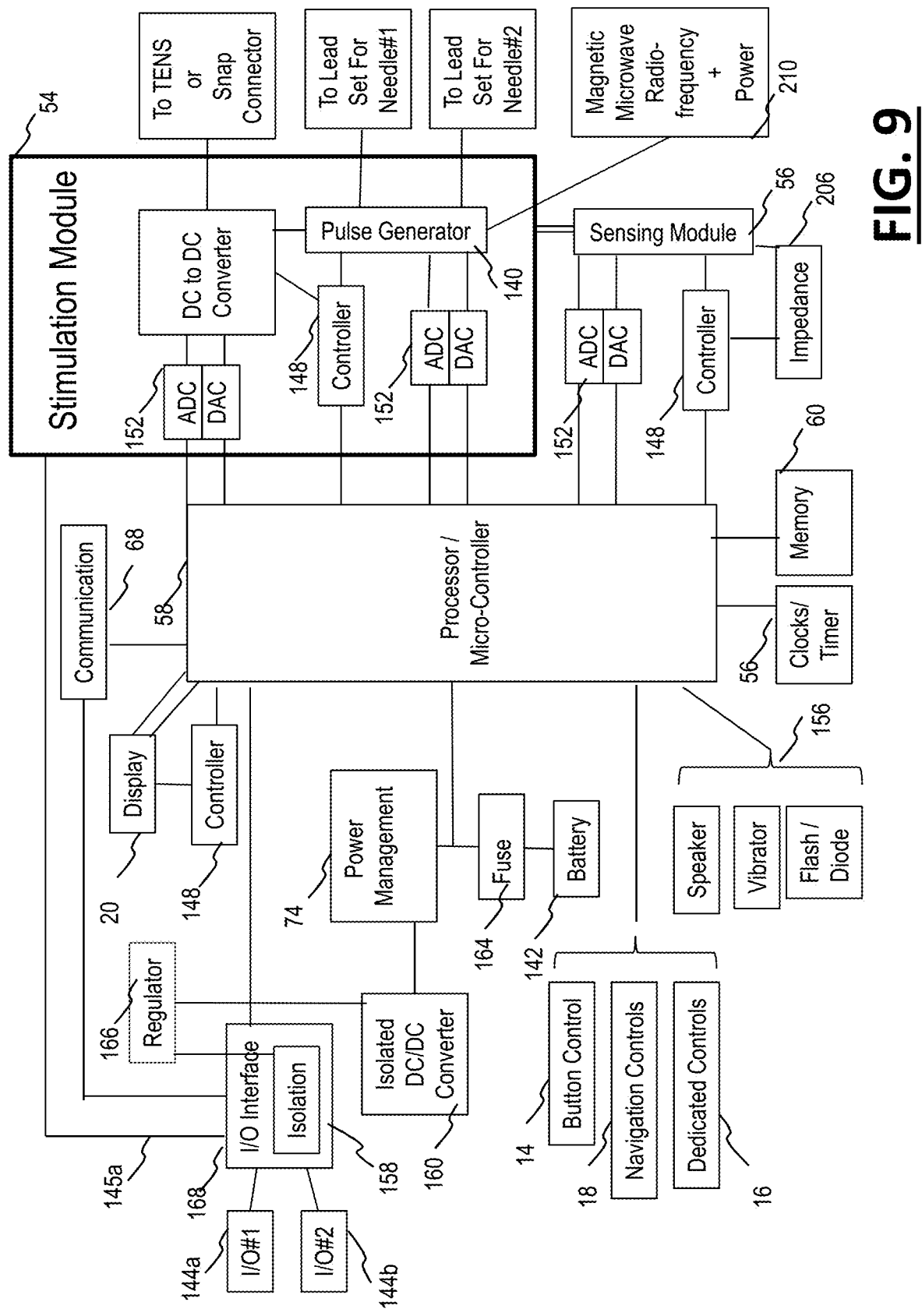
FIG. 9 is a schematic block diagram of circuitry that supports the functional modules of an embodiment of a neurostimulator system.

FIG. 9 shows a block diagram of circuitry modules provided in an embodiment of the neurostimulator 51a. A graphic display 20 such as an LCD visually presents information related to operation such as neurostimulation parameter values or information about compliance as shown in FIGS. 7A, 7B, power levels, elapsed time of stimulation, and treatment credit information. Patient input control can be realized using buttons such as power button 14, dedicated buttons 16 (e.g., start/pause/assess button), navigation controls 18 to assist a user in controlling the operation of device 51a via the processor/microcontroller 58 of the control module 52. The "assess" button allows the assessment of different stimulation parameters such as amplitude prior to providing therapy. The processor 58 controls operation the stimulation module 54 which includes a high voltage supply (DC to DC converter 154), pulse generating circuitry 140 and presents values of related operational characteristics on the display 20 using control circuitry of the control module 52 including a set of controllers 148. The pulse generating circuitry 140 can also provide circuitry that cooperates with the lead set to blow a fuse after the provision of simulation as is done in commercial systems that utilize single use paradigms. The controllers 148 can act as sets of one or more switches or be otherwise realized to adjust and control the operation of components of the stimulation module 54 including, for example, a DC to DC converter module 154 (or realized as any other signal conditioning module), digital-to-analog/analog-to-digital converters 152 under control of the DA/AD circuitry module 64. The controllers 148 can also act as sets of one or more switches or be otherwise realized to adjust and control the operation of the sensing module 56 to provide sensing at one or more sensors. The stimulation module also communicates with the wireless module 210 to provide power and/or data wirelessly to components of the system 8, such as an implantable neurostimulator or directly to human target tissue as may occur in TMS treatment for disorders such as depression, migraine or headache. One or more alerting components 156 may include a vibrating buzzer, speaker, light emitting diodes, etc. may be provided for notifying a user or patient about information relevant to therapy. This can include an indication, for example, that a treatment session is completed or is scheduled to occur, an impedance value is above a selected amount, a time has elapsed, the power has fallen below a selected amount, or other problem has occurred with the neurostimulator 51*a*.

In an embodiment, at least one port 144 enables communication to occur by way of the communication module 68 between the device and other components of the neurostimulation system 10 such as a USB, micro USB, or conductive cable connects to an I/O interface 168 module that can have isolation electronics such as an isolator 158 and isolated DC-to-DC converter 160 in order to electrically isolate at least one of the I/O ports 144*a*,144*b* from the other circuitry and components of the neurostimulation system 8. The neurostimulator 51*a* can also include a power management/ charging module 74 with a power management circuitry to regulate power operations. The power management/charging module 74 can include, and be disposed between, a battery 142 and the processor 58. The power management module 74 can have components to charge the battery 142, such as a wireless power harvester (e.g. induction coil configured for receiving energy by magnetic induction or rectennae configured for receiving RF or microwave energy) and associated circuitry, and/or can be configured for recharging the battery 142, using power from an I/O port 144*b*. One or more fuses can provide for both patient and device safety, such as fuse 164 disposed between the battery 142 and processor 58, or battery 142 and the other components of the power management/charging module 74. Regulators can be provided such as regulator 166 for maintaining a constant supply voltage to the I/O interface 168 when I/O ports 144*a* and/or 144*b* are connected to external equipment. Although shown as portable devices, the neurostimulators shown herein may be configured to be recharged using power converter that is plugged into a wall socket, with appropriate safety.

Figure 10A:
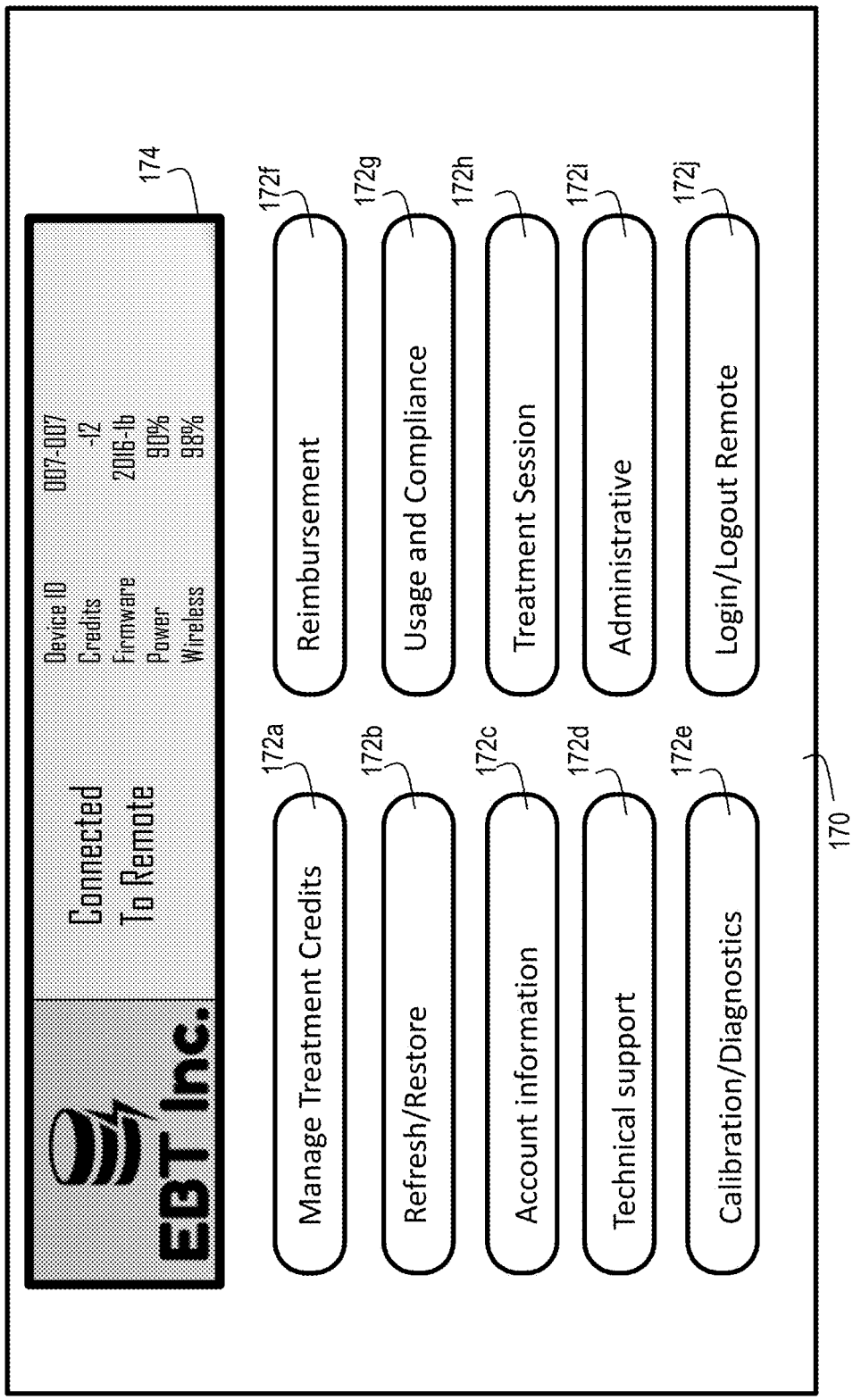
FIGS. 10A and 10B are views of example displays that serve as user interfaces in an embodiment of the system.

FIG. 10A, shows a menu screen of a computer system such as a computer in a medical clinic that is connected to the internet. In an embodiment related to use of neurostimulators 51*a* in a clinic, the computer may serve as a user/ physician programmer 70. The menu screen 170 is a user interface and includes virtual buttons that allow selection of operations related to managing one or more neurostimulators 51*a*. Each virtual button of the menu screen 170 can be supported by a corresponding module which includes all software and hardware required for implementing related tasks. For example, the manage treatment credits button 172*a* is part of a module that allows for purchasing treatment credits to be used with a particular neurostimulator 51*a*, and can operate with the payments and permissions module 202 of the system.

The user of the menu screen 170 may be a patient, doctor, technician, health care professional, office employee (with sufficient permissions), or anyone that manages treatment sessions with patients. The menu screen serves as a user interface that allows for user input and may be configured differently for different users. Pop-up dialogue boxes with fields for user ID and passwords can be presented to a user for making certain selections or adjustments. Clinic staff can enter ID codes assigned to the clinic to modify, view, and selectively adjust values related to a patient account, including managing payment credits, patient customer's account and related to programing and/or setting operating parameters of a neurostimulator 51*a*. The menu screen 170 is accessible from web-based application using a physician programmer 70 or computer.

A screen component shows status settings 174 related to one or more devices being adjusted by a user operating the menu, including device identification and use/connection status.

A button control, and associated module, is shown for managing treatment credits 172*a*. This selection invokes additional screens for managing and purchasing treatment credits, requesting treatment credit refunds, and for viewing a history of treatment credit transactions. It can also include dates and times of treatment credit purchase, download, therapy provision, patient ID and reimbursement code information, and other information. In an embodiment, a treatment credit can contain data fields having information about characteristics of the therapy to be provided such as the maximum treatment session duration, or can contain an interval or date during which the stimulation may be provided. Treatment credits may be provided with an expiration date after which they can no longer be used and become "expired". These may be exchanged for new treatment credits or "refreshed" using the module.

A button control, and associated module, is shown for refreshing/restoring 172*b* which will update the values on the status screen 174 to reflect for example, the current number of treatment credits for one or more neurostimulators 51*a*. The selection can also provide screens with options to, for example, restore a device to its default values, clear device memory, etc.

Additional selections that are provided include a button control, and associated modules, for adjusting account information related to a clinic or patient 172*c*.

Additional selections that are provided include a button control, and associated modules, for providing technical support such as viewing manuals or instructions on how to operate the device, or providing a chat window with a customer service representative 172*d*.

An additional selection that is provided is a button control, and associated module, for performing a calibration or diagnostic routine and displaying the results including whether the device passed various tests 172*e*. The selection can allow for running diagnostics such as a diagnostic check on a device 51*b* using a USB or other cable (loop-back cable), or by sending instructions and receiving data related to calibration and system test results wirelessly and if necessary requesting technical support 172*d*.

An additional selection that is provided is a button control, and associated module, for managing or requesting reimbursement for treatment by a patient's insurance company 172*f*.

An additional selection that is provided is a button control, and associated module, for viewing usage and compliance 172*g*. This permits obtaining, viewing, and managing historical data records related to usage, and further presented in relation to compliance criteria. Menu screens invoked when this button is selected can provide for a graphical or table view of the usage of one or more neurostimulators 51*b*. This can include information on patient ID, number and ID of associated treatment credits and reimbursement codes and payment information associated with the credits. This can include screens of patient usage as shown in FIGS. 7*a* and 7*b*. This can also include screens that allow for programming of compliance criteria such as weekly treatment goals as well as what to do in the case that criteria are met or fail to be met. Options related to how, when, and what information is queried of the patient (e.g., about symptoms, medication compliance), and scheduling presentation of survey items is also provided.

A button control, and associated module, is shown for allowing a user to adjust or run a treatment session 172h using an invoked menu interface to select or adjust a stimulation program and control the neurostimulator 51a to provide treatment. The treatment module 172h and control module of the neurostimulator may both contain non-transitory machine-readable storage media configured to store machine-executable instructions that is executed by processors of the system and can also include, for example, a look-up table, formulas, algorithms, a database having a matrix of treatment protocols and values associated with the protocols. For example, each column associated with a particular treatment contains parameter value settings such as frequency, amplitude, duration, duration of therapy, stimulator at which the signal is applied, inter-therapy intervals during which stimulation is not provided, number of maximum treatments allowed per day, number of total time allowed per day, maximum stimulation strength allowed, and any other operational parameter related to treatment with neurostimulator that is external, percutaneous, or implanted.

An additional selection is an "Administrative" button control 172i, and associated module, for providing administrative operations which invokes additional screens that allow for changing passwords and/or user IDs, for defining allowed ranges for stimulation parameters, for registering a neurostimulator to a particular patient (which can include options for viewing and modifying device information of the neurostimulator 51a).

An additional selection is a "Login/logout" button control 172j, and associated module, for allowing the device 51b, user/physician programmer 70, or remote user/physician programmer 70', to establish and terminate communication with each other or with the Management Computer 71.

Figure 10B:
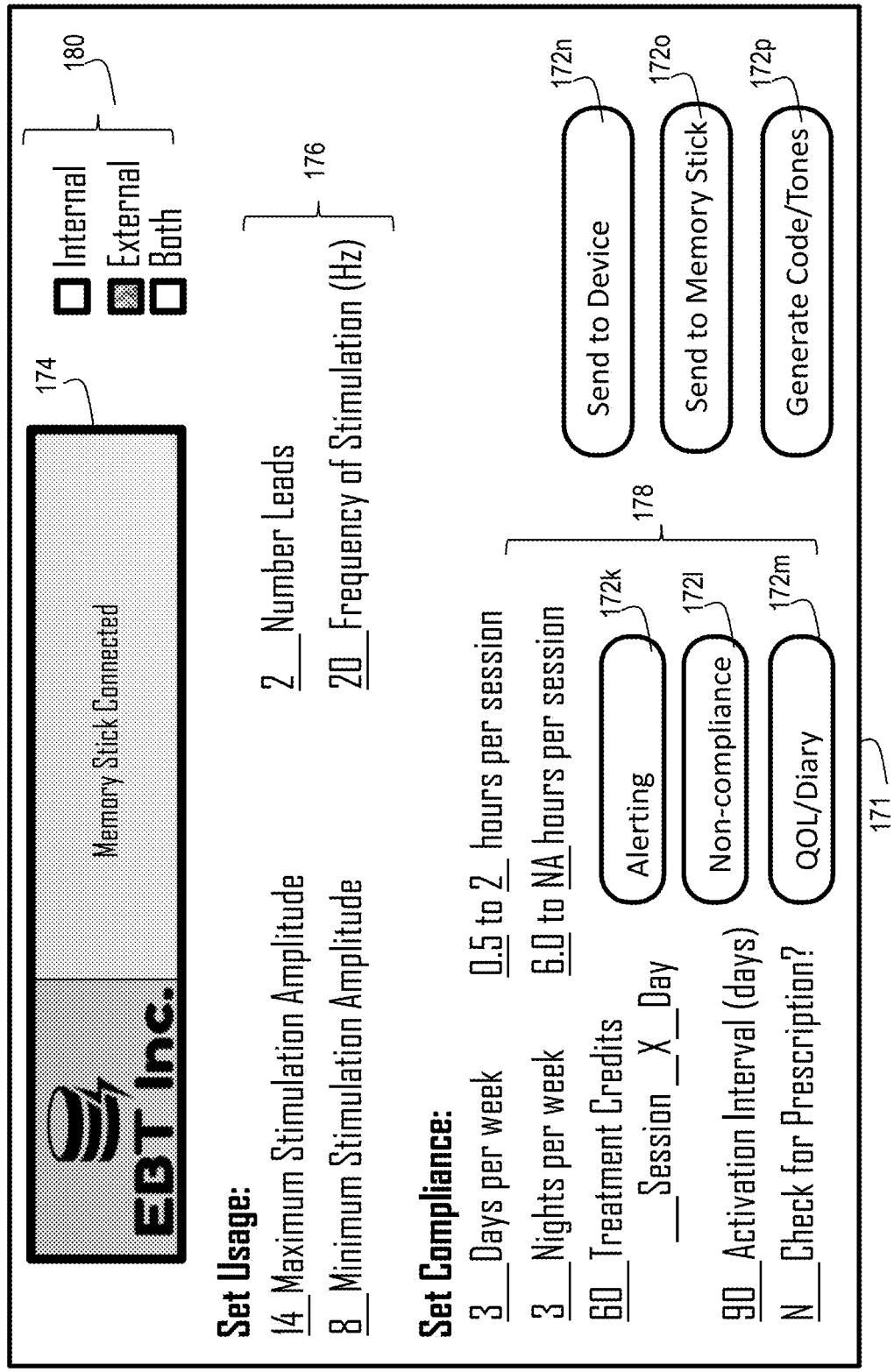

FIG. 10B, shows an embodiment of a menu screen of a computer system device of the system 10, which can be used for setting usage and compliance parameters. Usage parameter values 176 can be set for maximum and minimum amplitudes used during stimulation as well as the number of leads through which stimulation is provided (which may be allowed per treatment credit) and the frequency at which stimulation occurs. Additionally, parameters may include inter-stimulation pauses during which stimulation is not provided, ramping up or ramping down intervals which allow for smoother therapy onset and offset in order to deter disturbing a sleeping subject, maximum duration or # stimulations allowed for a given interval "dose", and any of the other stimulation parameter settings or limitations disclosed herein. Settings related to compliance 178 can be adjusted including, for example, number of days per week that stimulation should occur during the day (and the minimum and maximum time for each session). In this example, since the maximum amount of time is 2 hours the device may be set to not allow stimulation to occur longer than 2 hours in any particular 24 hour period if a "number of sessions per day" is set to 1. Compliance can also be set for the number of nights per week that stimulation should occur (and the minimum and maximum time for each session—in this example there is no maximum time limit). Compliance restrictions may also be related to dose-based criteria, for example, a higher amplitude stimulation signal can be associated with a shorter allowable interval (or total duration "on" over a selected interval) so that the "dose" remains approximately similar. Dose-based compliance relationships can be linear, such as doubling the stimulation amplitude (or number of pulses provided by a TMS coil) which can result in a halving of the maximum allowable duration or number of stimulation sessions allowed per unit time. Alternatively, strength/duration dose relationships may be non-linear and non-proportional. For example, in the treatment of depression, if the neurostimulator includes a TMS coil that delivers "N" pulses of "S" strength, and the user increases the number of pulses to 3N, then S may be reduced to 90%. The strength/duration, strength/number of treatments per unit time, or strength/number of stimulators used to provide stimulation, relationships defined by compliance criteria or other restrictions related to the provision of stimulation (e.g., defined in the payments and permissions module) may be defined in various manners. It may be defined by a prescription of a patient that is written by a doctor and realized in electronic form by the system, by findings of a safety study, by the severity of a disorder, by patient response to therapy, according to answers of survey questions, according to improvement seen during therapy, by drugs taken concurrently as part of treatment, by the patient's measured tolerance for pain, or otherwise and may be stored in a look-up table or defined by an equation of the set compliance module 178 which works with the compliance module 200 and other modules of the system.

The treatment session credit field of FIG. 10b shows that there are 60 treatment credits remaining prior to the device no longer allowing the user to provide stimulation sessions. A selection has been made to configure the system to cause a decrement of one treatment credit each day that the user provides at least one stimulation session. If "session" had been selected, then each time the user provided a stimulation session lasting longer than a selected amount (e.g. 5-30 minutes) then the treatment credit value would be decremented by 1. If the user stops before a minimum time limit (e.g., 5 minutes), then the session may not count and the treatment credit is not adjusted. An activation interval is also shown and the value is 90 days. This indicates that the neurostimulator will remain activated for 90 days from the current date. The treatment credit or activation interval fields may contain values or be left blank. If an interval of activation limitation is used without a treatment credit limitation, then the device will continue to provide stimulation treatment until the end of the interval. In an embodiment, in the case where no maximum is defined for the day/night stimulation fields (e.g. currently set at 3 and 3, where "3+" would signify "at least 3") then the user would be allowed to use the stimulator as many days as desired before the expiration date defined by the 90-day interval. There may also be compliance rules set up combination rules that utilize "if", "and", and "not" logic, such as a rule which does not allow stimulation to occur during the day if stimulation was provided the preceding night. In embodiments, the system 10 or neurostimulator 51 may be required to check (either periodically or before each use) for an active prescription (in a wired or wireless manner) to ensure that a doctor intends stimulation to be available. Like the treatment credit information, the prescription data stored in a computer 71,70' can also set limits for the maximum number, or length, of stimulation sessions per day. The current settings can be compared to the prescription if the "check prescription" value is set to "Y", which sets an operational flag in the payments and permissions module 202.

An "Alerting" button control 172k, and associated module, allows for setting alerting parameter for system components including device 51b, user/physician programmer 70, remote user/physician programmer 70, can also be used to alert a patient's smartphone, a customized EXD-pager type device worn by the patient, or remote Management Computer at a remote site 71 to send an alert (e.g., via e-mail or text message) to a patient to alert to various events including an upcoming therapy session, or to remind a patient if the therapy session was missed.

A "Non-Compliance" button control 172*l*, and associated module, allows setting parameter values and operations that contingently occur due to various types and thresholds of non-compliance. For example, alerting may also be set up to send an alert from the user programmer 70 to a clinic's computer 70' if the patient is severely non-compliant and device usage data meets a non-compliance threshold criterion established for the compliance module 200, for example, the data shows a failure to provide any therapy over the span of a month.

Another selection that is provided is a "QOL/Diary" button control 172*m*, and associated module, for allowing setting of operations related to obtaining quality of life (QOL) data and/or bladder diary data. For example, survey items for an electronic bladder diary may be presented to a patient on a defined schedule such as once a week. The data may be processed in different manners such as being used to generate summary statistics and trend graphs related to symptom improvement over time. The QOL/Diary/symptom data may be transmitted with other data to a computer in a clinic 70' so that this can be reviewed by a doctor prior to, during, or after a patient's clinic visit. The bladder diary items may be presented to a user visually in textual format with graphics where appropriate, or can be presented through a speaker of a device using text-to-voice technology or using pre-recorded messages. User response can be obtained by a user interacting with the neurostimulator or patient programmer 70 to select a score (e.g. choosing between 1 and 7, on a 7 point Likert scale), or by voice, if the device is configured with voice-to-text recognition. A user's responses can simply be digitally recorded and analyzed at a later time by a transcriber service. The non-compliance criterion can also be defined for the provision of QOL, bladder diary, or other survey responses data. User response data can occur across 1 or more scheduled sessions. Although QOL and bladder diary information are used in this example, the neurostimulator 51*a* can be configured to provide any type of assessment instrument or survey items related to a disorder suffered by, or condition to be modified in, a patient. This may include the assessment of depression, migraine, memory, pain, sleep apnea, anxiety, hypertension, tremor, concentration/attention/focus, sexual desire or performance, reaction time, etc.

A "Send to Device" button control 172*n*, and associated module, allows the user to update the neurostimulator 51*a* and/or the programmer 70 with the new settings.

A "Send to Memory stick" button control 172*o*, and associated module, allows the system to enable the updating of the neurostimulator 51*a* by providing the information on a memory stick that is given to the patient. When a patient does not want to visit a doctor's clinic and does not have access to internet or cellular coverage, or who may not be comfortable operating a computer, a memory stick may be provided which can simply be plugged into an I/O port 114 of a device 51*a*. This will provide an update to the device data and allow for continued treatment of a patient. Routines in the communication module 68 can allow upload of all device information (including usage and compliance) to the memory stick. This can then be sent back to the doctor's office so device data can be reviewed.

A "Generate Code/Tones" button control 172*o*, and associated module, allow for a code to be generated which can be printed out and sent (mailed/e-mailed) to a patient who can then enter the code into the neurostimulator 51*a* or programmer 70 using the user interface module 80 in order to allow for continued treatment of the patient. The code may extend the duration during which the device may be used, or increase the number of treatment credits which are present in the device. In embodiments, instead of a code, a barcode or the like (Data Matrix and QR Codes) can be printed out and the programmer 70 can read the code via a digital camera in order to re-activate the device. In embodiments, a computer can use a sonic protocol as is done by facsimile machines co communicate with a device 51*a* over a phone line, with appropriate modulation, handshaking, and demodulation implemented within the transmission protocol.

In an embodiment, operation of the menu screens shown in FIGS. 10A and 10B displayed to a user by a computer system, allows patient selections that cause a first processor of the control module 52 of the user/physician computer 70 to transmit data signals to a second processor of a remote computer 70' (or 71) which has been configured with communication 68 and control 52 modules designed to receive and operate upon the information data sent from the first processor. Further, the second processor is configured to access information values stored in memory 60 such as in at least one table that can be related to treatment of a patient such as: parameter values for a stimulation program, treatment credits, activation interval during which the device 51*a* is permitted to operate, values related to a status or limitations of a prescription of a patient, compliance data and/or criteria of a patient, payment information of a patient, insurance information of a patient, payment and identification information of a clinic, rights and privilege information that is related to a user of a neurostimulator, maintenance information related to a neurostimulator, and/or geographic location information related to a neurostimulator if the neurostimulator (or other system component) has GPS or uses other geo-location technology.

The information can be operated upon by the processor of the remote computer according to algorithms and rules related to compliance, payment, and provision of stimulation therapy by at least one neurostimulator 51*a*. The second computer can then transmit the result data of this processing as an information data result to the physician computer 70 in order to select, update, adjust, allow, disallow, or otherwise operate upon the settings that effect operations of a neurostimulator 51*a* in a manner that adjusts the provision of therapy for at least one patient. As is the case for the patient programmer 70 and other components of the subject invention, the components shown in FIGS. 10A and 10B can be used for stimulation systems which incorporate TENS and percutaneous stimulators as well as those having fully or partially implantable stimulators, and systems using implantable stimulators powered by external components. Combination systems can also be supported, such as providing TENS from an externally worn controller which also provides power to an implanted neurostimulator.

During a communication session when the neurostimulator 51*a* communicates with the computer 70, a processor can cause information to be updated and stored in the memory of the neurostimulator 51*a*. This can occur contingently based on user input operating the menu screen 170. For example, if one or more treatment credits are purchased, or are otherwise renewed (e.g., based upon the user meeting compliance criteria), then the treatment credits are sent by the computer 70 and received by the neurostimulator 51*a* processor and the number of available treatment credits is updated in the payment and permission module 202 in order to enable treatment sessions to occur. When the neurostimulator 51a is in communication with the computer 70 or a computer system network that communicates, in a wired or wireless manner, with the computer 70, then parameter values used by the neurostimulator 51a during operation (e.g. a permitted range of values for various parameter settings) can be adjusted.

The stimulation treatment regimen may be defined for use with an implanted neurostimulator, and external neurostimulator, or a treatment regimen that includes the combination. The treatment compliance module 200 operations are adjusted accordingly. The determination of whether the regimen includes implanted, external, or combination neurostimulation is adjusted using controls 180.

TENS System and Method Embodiments

Although the SAFN or PTN may be stimulated using generic TENS stimulators having at least a first and second TENS electrode that can be placed to provide stimulation of these nerves, recent TENS technology has moved towards specialized systems which are wireless and which use pads or electrode arrays and also provide features which promote better treatment response and easier patient experience. FIG. 11A shows an embodiment of a system for providing SAFN TENS stimulation of a patient 6 which includes at least two adhesive TENS pad electrodes 30e, 30f that are disposed within a leg applicator accessory 220 which may be a garment configured for positioning at least one electrode on the medial upper calf area. The garment maybe a customized sock, wrap, or similar type of shaped garment that can be worn by a user. In this embodiment, the leg applicator accessory 220 serves to position at least two TENS stimulators within the material and along the medial leg surface with the first positioned approximately several inches below the knee and the second located about midway between the first electrode and the medial malleolus. Although the accessory 220 is shown here forming a sock, the accessory 220 can be designed extend distally only to a location cephalad to the medial malleolus and does not need to cover the foot. A lead set 86c can travel within the garment or be routed along the garment and communicates the stimulation signals to the electrodes 30e, 30f from a neurostimulator 50 (not shown), which may be strapped to a patient's leg, worn around the patient's waist, or disposed in a pocket on the top of the accessory 220. The electrodes can operate in a bipolar manner with electrodes 30e, 30f or these can both be referenced to an additional electrode, which may be on the bottom side of the neurostimulator. Rather than both electrodes being below the knee, one can be above and the other below as may occur with a knee sleeve electrotherapy garment with dual electrodes. Typically, when a conductive fabric is used, these should be formed within a garment as specific, electrically-active areas that are formed to electrically target specific anatomical areas so that stimulation can be applied to the SAFN without stimulating other targets such as calf muscle or the sural nerve on the lateral side of the leg. A shaped area of electro-conductive garment 31 is shown around electrode 30f.

FIG. 11B shows an alternative embodiment of a system for providing SAFN TENS stimulation of a patient 6 which includes at least two adhesive TENS pad electrodes 30g,h and 30i,j (j is not shown) that are disposed within each of two upper leg applicator accessories 222a, 222b, made of a formed and/or elastic garment material that can be worn by a patient and which serves to position the stimulators along the medial leg surface approximately at or below the knee to 3 or 4 inches below the knee (although in embodiments it may extend to just above the medial malleolus). The stimulation provided by the embodiment in 11B may be suitable for stimulating the infrapatellar branch of the SAFN, which may be less comfortable for some users and may also be more difficult to assess with respect to confirming correct placement of the electrodes. A lead set 86d communicates the stimulation signals from a neurostimulator 51c which here is shown disposed on the top of the accessory 222a (it can be configured to be snapped onto the garment or held in a pocket disposed in the garment), to the electrodes 30g, 30h. An electrode pad 301 is shown on accessory 222b which communicates to another neurostimulator (not shown), in order to provide bilateral stimulation. Alternatively, all electrode pads can be connected to a single neurostimulator using a wire that runs up one leg and down the other. When two neurostimulators are used, they may communicate in a wired or wireless manner in order to synchronize the stimulation of both legs so that the signals applied to the first and second leg occur at a desired lag, which may be a delay of zero as set by the stimulation protocol. When a 10 Hz stimulation signal is applied to each leg 180-degrees out-of-phase, then the stimulation may be functionally equivalent to 20 Hz at central nervous locations commonly innervated by the peripheral signals from each leg.

FIG. 11C shows an alternative embodiment of a system for providing SAFN TENS stimulation of a patient 6 which may be simpler because it does not have free-standing lead wires. The neurostimulator 51d can be realized in a basic embodiment that has only a few controls and no wires. The neurostimulator 51d has a first wing 224a having a top side with a first control 16a which is a plus symbol "+" and a second wing 224b having a top surface with a second control 16b with a negative symbol "−". The neurostimulator 51d components are contained within a housing having a center region with a battery compartment 228 for accepting at least one rechargeable or disposable battery 142 which powers the neurostimulator 51d. The control module 52 of the neurostimulator 51d is connected to the first and second user interface controls 16a, 16b. The user can turn on the device 51d, under control of the control module 52 by pressing the user interface controls according to defined patterns. For example, pressing the first and second button 16a, 16b for 3 seconds can turn the unit on and doing this again will turn it off. The user can increase the stimulation by pressing the first control 16a or decrease the stimulation by pressing the second control 16b. In an embodiment, after the device is turned on and connected to a user with acceptable impedance levels, it will provide a timed stimulation session which lasts a selected interval such as 30 minutes, after which the device may power down. Alternatively, the device may continue periodically (every 2 hours) provide additional stimulation sessions (e.g., pulse rate 5 to 50 Hz and pulse width 150 μs) as long as it remains connected to a user. The first and second wings are made of a flexible material such as rubber or silicon and have snap connectors 89a, 89b on their bottom surfaces (that receive stimulation signals by a lead set 86e that resides within each of the first and second wings) which attach to an electrode array comprising two electrodes provided as a reusable adhesive electrode pad that has the same shape as the device 51d and which snaps onto the connectors 89a, 89b of the first and second wings. Signal transducers for providing alert signaling 156 can include a led diode or speaker provided on the top surface of the first wing in order to notify the user about the start or stop of stimulation therapy and also can provide a warning alert if either electrode pad is not attached correctly as can be measured by an impedance module or other electronics that can detect this problem. The unit can use codes such as "a single long high beep" or "two long high beeps" where high is 1000 Hz or a low buzz (500 Hz) if, for example, the power management 74 indicates that the battery 142 is low. Voice messages can also be used. A communication module may also be provided to enable the stimulator 51*d* to wirelessly send and receive data and be controlled by a smartphone which can serve as a user/physician programmer 70. Additionally, diodes or an LCD can allow signaling of information such as battery charge.

In order to maintain the neurostimulator 51*d* in position at least a first strap 229*a* is provided which is attached to the first wing 224*a* and configured to wrap around the calf area to secure the first wing to the user's leg. Additionally, a second strap 229*b* may be provided which is attached to the second wing 224*b* and configured to wrap around the calf area to secure the second wing to the user's leg. The straps act to secure the neurostimulator 51*d* in position and apply compression to bias each of the wings and the TENS attached to the bottom surface of each wing against the user's leg. A strap can also be configured to be attached to the housing of a neurostimulator or an electrode array rather than the two wings. The strap is configured with a length and fastening means which allows for the strap to wrap around a leg circumference of between 30 to 48 cm corresponding to that expected in the calf area of an adult user (McDowell et al Anthropometric Reference Data for Children and Adults: United States, 2003-2006).

In an embodiment, when the neurostimulator 51*d* is configured to work jointly with an implantable neurostimulator which is controlled by an external controller, then conduits 86*a* conduct energy to power either RF or magnetic transmitters to power the implanted device. Alternatively, the RF or magnetic transmitters are located in the housing of the neurostimulator 51*d* and the neurostimulator 51*d* is configured to also provide TENS either concurrently or at a different time that the implantable neurostimulator provides stimulation. The neurostimulator 51*d* can be controlled by a user programmer 70, which also controls the implantable neurostimulator either by communicating directly or by working jointly with the neurostimulator 51*d*.

Figure 12:
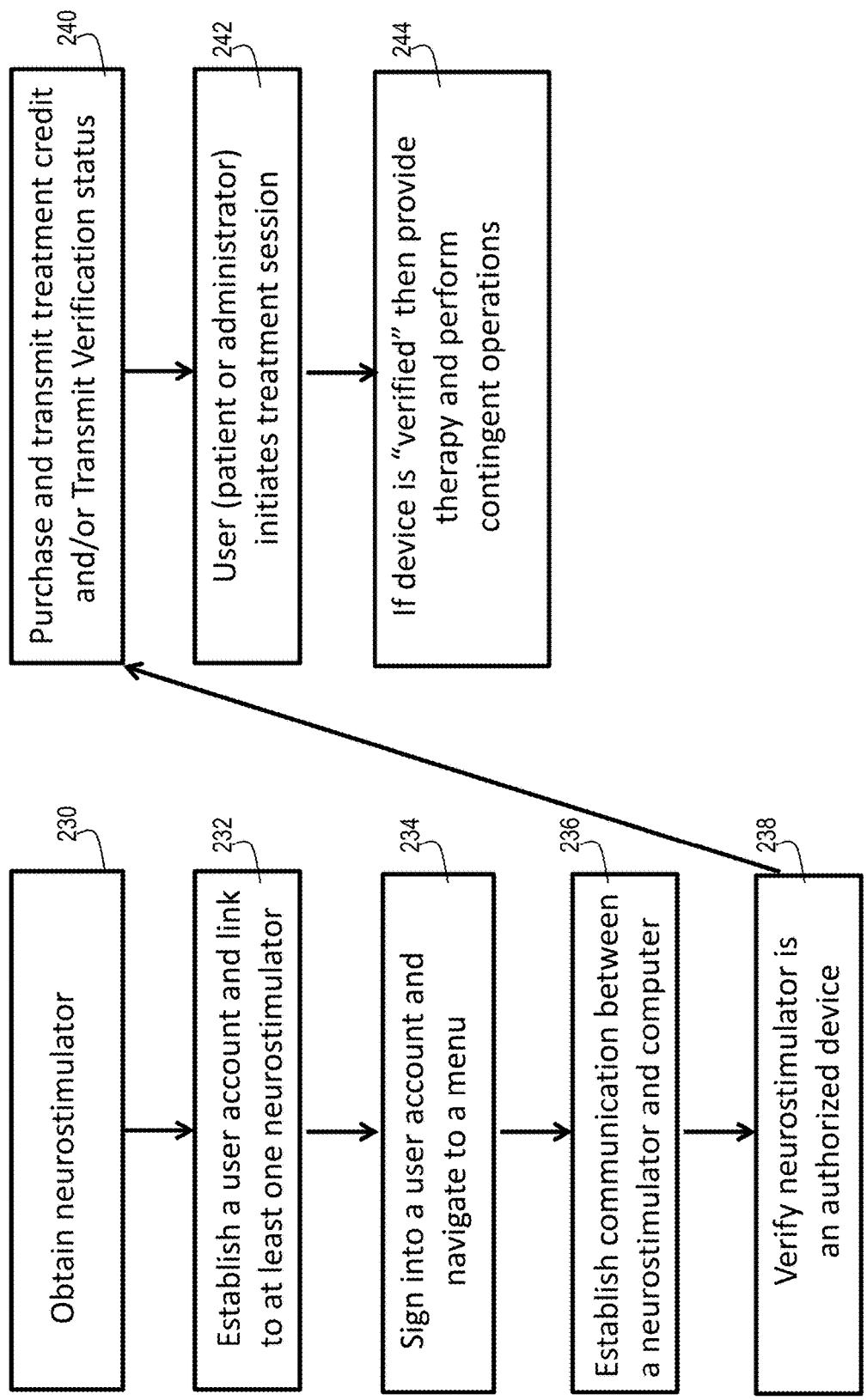
FIG. 12 shows a flow chart of a method for providing therapy.

FIG. 12 shows an embodiment of a method for performing OAB treatment such as a SAFN stimulation treatment session using a neurostimulator 51*a*. Various steps may be performed in a different order, omitted, or repeated. In a general embodiment the steps of FIG. 12 can occur so that the device is operated based upon a verification-treatment basis. This means that when one or more defined verification criteria are met, stimulation treatment can be provided to a patient. The verification step can simply entail assessing if a per-treatment session payment credit is available, and if not then a payment must be made before the neurostimulator 51*a* is "verified". For example, during verification the number of stimulation-credits of the system 10 is assessed and must be above a selected value for verification to be true. Once verified the device is granted permission (i.e., set a verification status flag to true) to provide stimulation. The stimulation treatment credit value is decremented by a value of 1 either in a device 51*a* or in a user/programmer 70 before, during, or after the stimulation is provided. The permission flag may have a time limit such as a subsequent interval of one hour, 2 hours, one week, or other defined interval. The decrement in treatment credit value may only occur after a stimulator 51*a* has been used for a minimum amount of time, such as 7 minutes, to avoid charging a user for an "incomplete" stimulation session that does not last a minimum duration. In step 230, a user (patient or physician) obtains a neurostimulator 51*a* and performs the additional steps to set up the hardware for providing treatment.

In step 232, a user establishes a user account on the computer system. If the neurostimulator 51*a* has not been previously used by the user then the user can link the neurostimulator 51*a* with a user account and/or user ID. The user ID may be for a clinic when the device is used in a clinic or may be for a patient who will be treated by the clinic. The User ID can be for a user when the device will be used at a patient's home. Preferably, the payment and permission module 202 of a neurostimulator has, or is assigned, a unique identification number by which it is identified during communication/transaction with a computer system.

In step 234, a user can sign into a user account, navigate to a menu 170 and select, for example, a choice of "manage treatment credits" 172*a* that enables the purchase of one or more treatment credits. Each purchased treatment credit that is uploaded to the physician programmer 70, and/or the neurostimulator 51*a* preferably includes data and a unique identification number.

In step 236, communication between a neurostimulator 51*a* and a computer system (which may include any of 70, 70', 71 and communication therebetween) is established using wired or wireless communication. Communication can also occur between the computer and a memory stick which will then be used to transfer data and credits to the neurostimulator during a separate step. The modules can be stored and operated on a server computer having a processor and control module configured to provide user accounts that can also allow management of user and device information. The communication can include reading and/or adjustment of initial parameter values that are set for the device 51*a* at the start of the communication session and final parameter values that exist at the end of the communication. Step 236 can include a step of providing information to a user on a display 174 of the physician programmer or on a display 79 of the neurostimulator 51*a*.

After verification that the neurostimulator 51*a* is an authorized device 238 that has been associated or "linked" with a particular user account and/or user ID, in step 240 the computer system transmits one or more treatment credits that are available or which may be purchased to the neurostimulator 51*a*. Alternatively, as has been disclosed, information could be transferred between the computer system and the neurostimulator 51*a* using a digital storage device such as a flash drive as part of step 240. In step 240 a code can be generated that is simply manually entered or optically scanned into the neurostimulator 51*b* by a user and operation of the payments and permissions module 202 has been previously programmed to interpret the code to provide appropriate functionality.

Transmission of a purchased treatment credit between an external computing device and the neurostimulator 51*a*, can include one-way or two-way communication of information related to number of remaining treatment credits available (if any), the total number of treatment sessions (and associated times and intervals) which have already been provided, or which are scheduled to be provided by the neurostimulator 51*a*, a count, including details, related to "incomplete" treatment sessions that did not last longer than a minimum amount (and related details), information related to the use of a particular treatment credit based on a unique serial number and any associate information related to a user account, user ID, patient ID, and other operational information. Instead of treatment credits and especially in the case where a user of the neurostimulator is used by a patient rather than a physician, if the device is "verified" due to patient data and/or payment information meeting all relevant criteria (i.e., a patient has met all defined compliance criteria and the patient is paid up through the current month, etc) then the device may simply be verified and information is sent which allows the neurostimulator 51a to operate for an upcoming period such as another month, after which the user must "renew" the neurostimulator 51a.

In step 242, the patient or administrator operates the neurostimulator 51a to provide a treatment session. In step 244, the neurostimulator 51a determines whether the device is "verified" which may simply entail determining if a treatment credit is available. However, even if a treatment credit is available, if the patient has not met compliance criteria or if a prescription for the patient using the device has expired then the device 51a may not provide stimulation. If the device is verified then the neurostimulator may provide treatment and perform contingent operations such as managing a parameter value associated with treatment credits. If it is determined in step 244 that there are no more available treatment credits or that the device is not "verified", then the user must return to step 240 to purchase additional treatment credits before another treatment session may be performed or the device may be otherwise verified.

If a treatment credit is available, and the device is verified then the nerve stimulation 51a performs a treatment session using one of the treatment credits purchased and transferred to the neurostimulator 240. In performing the treatment session, the neurostimulator 51a activates the pulse generator so that current pulses of a stimulation signal traverse the stimulation site during the treatment session by passing between stimulators such as from the TENS electrode 88 to the percutaneous electrode needle 28. If the device is operated on a pay-per-session basis then after a treatment session is performed, the number of available treatment credits is reduced by one. Step 242 is then repeated when another treatment session is desired. In embodiments, the system allows for devices to be verified although a treatment credit value may be negative reflecting a treatment credit deficit.

Figure 13B:
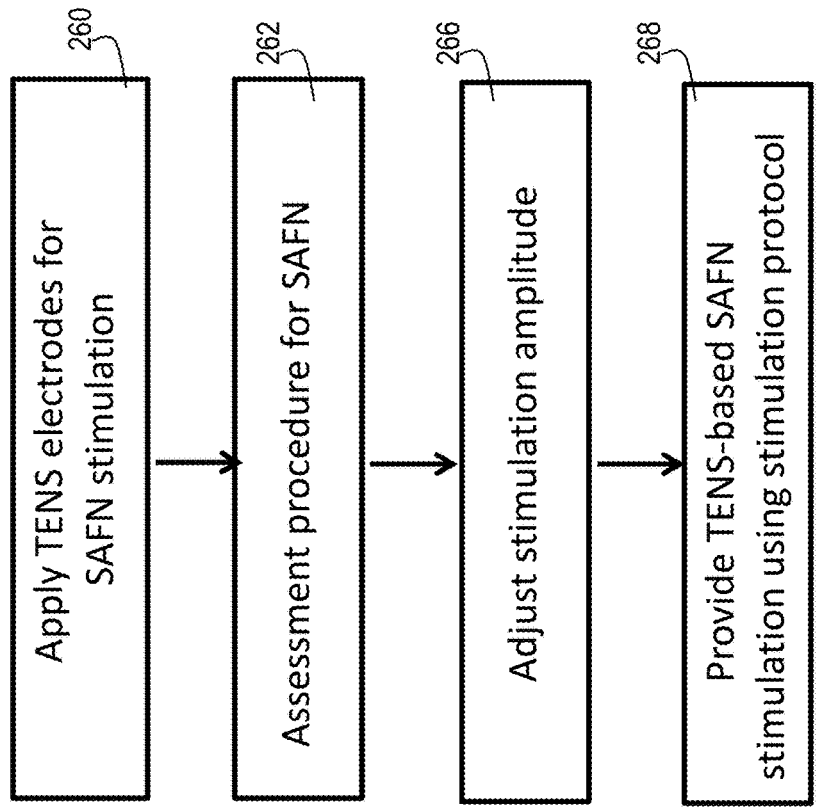
FIGS. 13A and 13B show additional flow charts of a method for providing therapy.
Figure 13A:
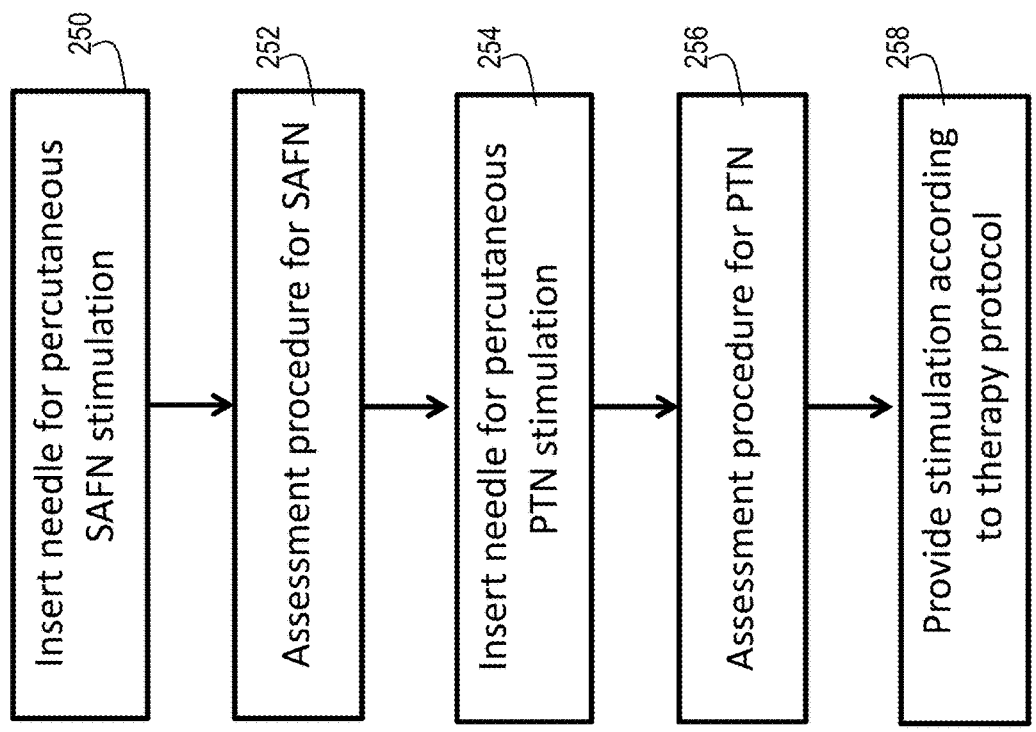

Methods for providing therapy are shown in FIG. 13A, where in a first step 250, a needle electrode is percutaneously inserted in the leg at or below the knee at a position known, or determined to be, appropriate for stimulation of the SAFN.

In a second step 252, an assessment procedure is performed wherein the signal provided by a neurostimulator 51b is increased in steps (e.g., 0.5 uA, 50 uA, or 0.5 mA) from a starting value to a value at which the patient experiences tingling, warmth, pressure, vibration or other similar sensory event which has been determined to indicate that the SAFN is stimulated. It is expected that this typically should include a sensation that radiates away from the site of the electrodes and often will spread down the leg and even towards the hallux medial malleolus, ankle, or into the foot, or toes (or up the leg if a stimulator is located near the foot). The stimulation level is then increased from above nerve recruitment threshold to a level that is greater but not painful to the subject and is provided during treatment. If the patient is not able to feel "tingling", or if it occurs at an amplitude that is higher than what is expected for that patient (compared to previous sessions of that patient) then the needle electrode may be re-oriented or inserted in a new location, and the assessment is repeated. The stimulation is then typically halted while the assessment is done for the PTN stimulation site. An assessment mode of the device may provide an assessment signal which increases its amplitude or pulse width to allow the patient to better sense the electrical recruitment of a target nerve.

In some embodiments for combined SAFN and PTN stimulation, a step 254 may be done in which a needle electrode is percutaneously inserted in the foot or leg at a position known, or determined to be, appropriate for stimulation of the PTN.

In step 256, the signal provided by the second neurostimulator 51a (or a second stimulus generator of neurostimulator 51b) is increased in steps from a starting value to a value at which the patient experiences a foot motor response which indicates that the PTN is stimulated. That level is the used to adjust the stimulation amplitude that is provided during treatment. If no foot twitch is seen or measured from a sensor, or if the subjective sensation of a muscle response occurs at an amplitude that is higher than what is expected for that patient then the needle electrode is removed, inserted in a new location, and the assessment is done again. After a successful location is found the stimulation can then be halted for the PTN stimulator until combination treatment is initiated.

In the fifth step 258, combination stimulation is provided to both the SAFN and the PTN according to a selected therapy protocol whereby the signals for the first and second stimulators are provided and therapy continues for the selected therapy interval. For example, the stimulation may alternate between the SAFN and the PTN, may occur simultaneously, or may occur as otherwise designed. A variant of this method can include using two stimulation sites which are both SAFN. Sites can be selected on the same or different leg. Although this method is oriented for percutaneous stimulation, a similar method can be used for combination TENS therapy (or other type of stimulation) where the stimulation of the SAFN and PTN are assessed separately before stimulation therapy is provided.

As shown in FIG. 13B, in a first step 260, at least a first TENS electrode is attached to a subject's leg at a position known, or determined to be, appropriate for stimulation of the SAFN, while at least a second TENS electrode is placed nearby, preferably lower on the medial surface of the leg or at a location such as the inner sole of the foot.

The TENS approach to electrically stimulating the SAFN for the treatment of OAB will typically involve placing at least one pair of surface electrodes placed on the medial aspect of the lower leg (e.g. step 260 of FIG. 13B), with one electrode slightly below the knee. Placement of the electrodes may target the SAFN branches that travel subcutaneously from the level of the knee down to the ankle but electrodes on the medial aspect of the sole of the foot may also be found to provide effective bladder modulation. Anatomical studies in human cadavers report a high degree of variability in the anatomical location of the SAFN branches (Wilmot, V. V. and Evans, D. J. R. (2013), *Categorizing the distribution of the saphenous nerve in relation to the great saphenous vein*. Clin. Anat., 26: 531-536). As such, the optimal electrode configuration may vary from one patient to another. In general, the SAFN emerges as either single or multiple fascicles at the level of the knee, immediately posterior to the medial condyle of the tibia. These travel along the medial aspect of the leg and can be located either anterior or posterior to the saphenous vein. Anatomically, the saphenous vein is located along the posterior margin of the tibial bone. Therefore, the main SAFN may be located more anterior or posterior to the posterior margin of the tibia. Placing the electrode too posterior to the tibia may result in the electrode being directly over the medical gastrocnemius muscle, which may be electrically activated during stimulation. This unintended muscle activation may cause discomfort to the patient. If this occurs, the electrode should likely be repositioned and stimulation tried again to avoid this.

In a second step 262, an assessment procedure is performed wherein the signal provided by a neurostimulator 51b is increased in steps from a starting value to a value at which the patient experiences a tingling sensation radiating along the leg which indicates that the SAFN is being modulated. That level can then be used to adjust the stimulation amplitude that is provided during treatment 266. If the patient is not able to feel the expected sensation, or if it occurs at an amplitude that is higher than what is expected for that patient (compared to previous sessions of that patient) then at least the first TENS electrode is removed, applied to a new location on the medial aspect of the leg, and the assessment is repeated. Rather than moving a single electrode, an electrode array or neurostimulator having pairs of electrodes can be moved or stimulation elements of the array may be selected to change the spatial stimulation area.

During assessment of the SAFN 262, a doctor or patient may be instructed that correct electrode placement and electrical stimulation of the SAFN may be determined if a patient can confirm a "tingling" sensation that radiates below the site of stimulation. If stimulation evokes a foot motor response, then the selected electrode placement and/or selected stimulation signal may be (co-)activating the tibial nerve. In this case, it may be beneficial to change the location of one or more electrodes and re-assess.

With respect to adjusting stimulation characteristics 266, amplitude is typically set at the maximum value that is tolerated by the patient in the case of PTNS treatment. This may also occur in SAFN therapy, or the SAFN stimulation protocol may be distinct. For example, the protocol may instruct a user to determine the maximum stimulation and then reduce the amplitude by 10%, 20% or 50%, as long as nerve activation still occurs. In order to ensure that TENS is effective, it is likely that the minimum amplitude used for treatment will be defined by the amplitude at which the electrodes (e.g., location 29b) evoke a sensory percept that spreads away from the distal electrode down the leg. This indicates that the subcutaneously located SAFN fascicle(s) are activated by the TENS electrodes.

In an embodiment, at least one surface electrode will be placed within the upper one-third of the lower leg to target the main fascicle(s) of the SAFN. The return electrode may be placed at more distal locations, such as the mid-point between the knee and the foot (29d or anterior to this location), 5 cm cephalad to the medial malleolus (29c), or the medial aspect of the sole of the foot (location 88). When stimulation characteristics of the signal are adjusted 266, polarity can be assigned as part of the stimulation protocol. The polarity of each electrode may be set to positive (anode) or negative (cathode), or this may be adjusted depending on the preference indicated by the patient based upon subjective comfort, or this may change during the stimulation.

In the fifth step 268, stimulation is provided to at least the SAFN of one leg according to a selected stimulation protocol for the selected therapy interval such as 30 minutes. The method can also perform the assessment or treatment bilaterally or choose the leg that shows stronger recruitment of the SAFN or its branches.

Figure 14:
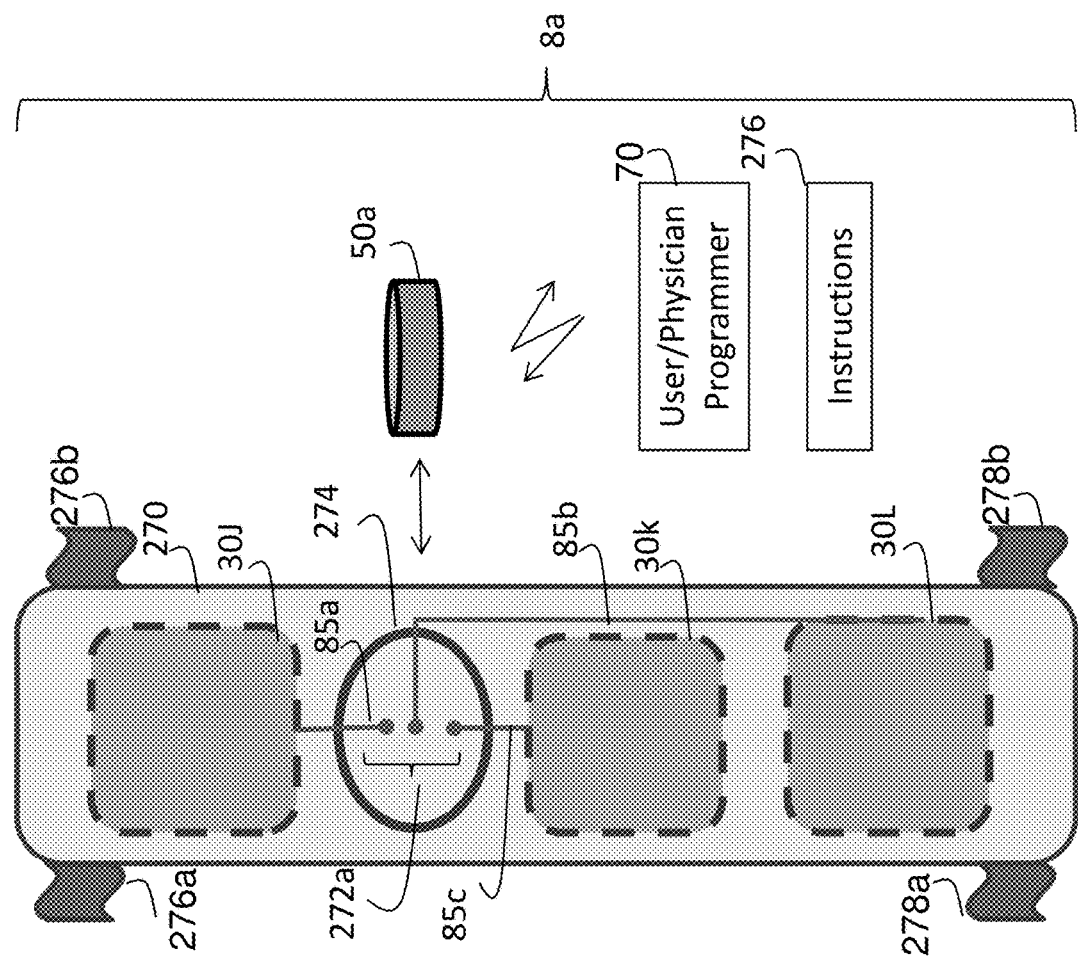
FIG. 14 shows a TENS system having an electrode array and a neurostimulator.

FIG. 14 shows a system 8a for providing TENS stimulation including an electrode array 270 having three TENS electrodes 30j,k,l which are connected by conduits 85a,b,c to three connector sockets 272a which reside within a receptor base 274. Rather than connector sockets a connector can contain routing circuitry and other electronics which can be under control of the neurostimulator 50a or the programmer 70. A first strap 276 can be configured as first 276a strap portion and second 276b strap portion which are connected to the array 270 on their proximal ends and which have fastening portions on their distal ends (e.g. Velcro) or which may be made of a sports wrap type material that allows the strap portions to grip each other without sticking to the leg of the user 6. A second strap 278 may also be provided on the bottom end of the array 270. Rather than being connected permanently to the array 270 the straps can be configured to snap onto the array. The receptor base can be formed of plastic or rubber and is shaped to receive a neurostimulator 50a which snaps into the connector sockets 272a so as to reversibly attach the neurostimulator 50a to the electrode array 270. In an embodiment, the array is fabricated using foam, silicone, or rubber material which is flexible and which provides for routing of the conduits 85 to the TENS electrode pads 30. The view shown is the top side of the array 270 and the bottom side is disposed with 3 areas of electrode hydrogel or conductive material provided on the TENS electrodes for connecting to the user's skin. There is also provided a user/physician programmer which may be realized as a smartphone on which a software application has been downloaded or by a customized user interface device (a battery powered remote control) which communicates with the neurostimulator 50a or electronics provided on the array 270 in a wired or wireless manner. When provided as a kit, the array 270, neurostimulator 50a, programmer 70, and instructions for use 276 may be included. In an embodiment, the array 270 is designed to be disposable and provide for approximately 1 month of use.

In an embodiment, the stimulation protocol can stimulate by referencing the first TENS electrode 30J to the second and third electrodes 30k,l if the patient can tolerate this. Alternatively, combinations of stimulation circuits which include electrodes 1 and 2, 2 and 3, 1 and 3, or 1 referenced to 2 and 3 (or 2 referenced to 1 and 3) can be selected based upon patient comfort or the success of different electrode combinations to recruit the SAFN and produce a tingling sensation that radiates down a subjects leg from the upper-calf where the array is positioned during use. Allowing a user to selectively and programmably activate unique pairs from the 3 electrodes based upon user input can allow a patient to select a stimulation montage that stimulates the SAFN without having to physically remove and replace the array to obtain successful positioning of electrodes. It also may be that in some subjects increasing the size of the electrode field serves to recruit more nerve branches/fibers, while for others only 2 electrodes work better. In an embodiment, only two TENS electrodes (or more than 3) are provided on the array. Electrode combinations can be determined during assessment 262.

Figure 15:
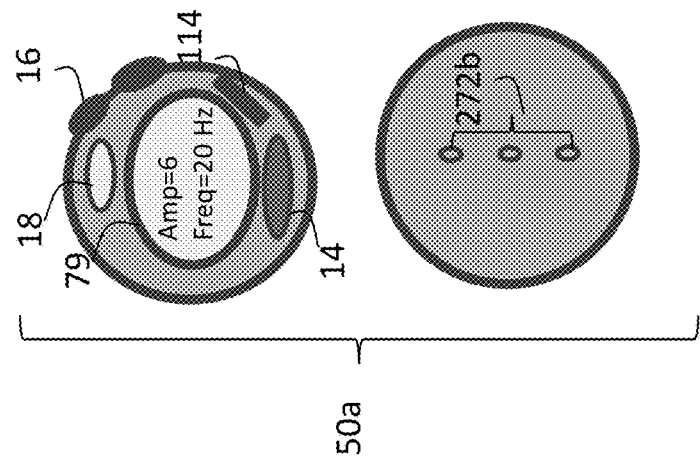
FIG. 15 shows a top and bottom portion of a neurostimulator.

FIG. 15 shows front and back views of a neurostimulator 50a on the top and bottom of the figure, respectively. The front side of the neurostimulator shows a display 79, a power button 14, a menu control 18, and dedicated buttons 16 which may be used for example, to increase or decrease stimulation amplitude. Interface port 114 allows for powering the device or for wired communication with other system components. The back view shows three connector sockets 272b which connect to the corresponding sockets 272a on the neurostimulator. Although the neurostimulator 51b shown in FIG. 2 only has one connector on its bottom surface for connecting to a TENS electrode, the other 2 connectors can simply be inactive during percutaneous stimulation when that stimulator is designed to be used for providing therapy both percutaneously and transcutaneously.

In this system patients can begin OAB treatment by receiving percutaneous stimulation in a clinic for a number of sessions and then the neurostimulator can be used by the patient to provide TENS by interfacing with an electrode array. While the treatment credits can be used to manage in-clinic percutaneous stimulation, these can also allow for a month of TENS treatment per credit, when the neurostimulator is used at home by a single patient rather than in the clinic by multiple patients.

Kits and Methods for Providing TENS of the SAFN for OAB Treatment.

In an embodiment, the invention is realized as a kit having at least two TENS electrodes 88 configured to receive a stimulation signal from a TENS neurostimulator 50*a*. The stimulation signal can be provided according to a stimulation protocol that is defined for stimulation of the SAFN for the treatment of overactive bladder. The kit also includes instructions 276 for using the neurostimulator for the treatment of overactive bladder disorder which includes instructing a user to apply at least one of the 2 stimulators on the medial aspect of the leg below the knee such as for the treatment of OAB by electrical stimulation of the SAFN. In instructions 276, it may alternatively include instructions to place at least one of the two TENS electrodes on the inner side of the leg in the area near the upper calf and then provide a stimulation signal to determine if at least one of a tingling, vibrating, buzzing, pressure, electrotactile tactile sensation, warmth, or tickling sensation (or other paresthesia) is experienced as radiating away from the location of at least one of the two electrodes. Further, the instructions direct a user in the case where the sensation is not experienced, and the application of the stimulation signal fails to produce a radiating sensation indicating that the SAFN has been stimulated, then performing the step of either increasing the stimulation signal or adjust the position of at least one of the two TENS electrodes. In the case where the sensation is experienced then provide a stimulation session using a stimulation strength that does not cause pain.

In one embodiment, determining if a sensation occurs includes determining if the sensation is radiating away from an electrode and down the leg towards or into the foot. Alternatively, instructions may also include directions to place a second lower electrode near the medial malleolus or the sole of the foot and determining if a sensation occurs includes determining if the sensation is either radiating away from the first electrode and down the leg, or away from the second lower electrode an up the leg.

The instruction 276 can include or be provided on paper or as part of the user interface module which has multimedia ability for providing instructions via the neurostimulator 10*a* or the programmer 70.

In an embodiment, the at least two TENS electrodes can be realized as part of an accessory such as a garment or an electrode array that positions the electrodes on the medial aspect of a patient's leg with at least one electrode positioned approximately 1-4 inches below the patella or within approximately 1-4 inches of the medial condyle of the tibia.

An external patient programmer can be configured to communicate with and provide user control of the neurostimulator and at least one of the neurostimulator and external patient programmer are configured to monitor usage and assess compliance with respect to a treatment program that is related to treatment of overactive bladder and to provide patient alert reminders related to a stimulation program that is defined for the treatment of overactive bladder.

In an embodiment, the stimulation signal is defined to be a pulse train modulated at 10 Hz, 20 Hz, or can be a signal that roves between 10 and 20 Hz. The stimulation signal may be defined to be at least one of: slightly above (e.g. 0.5 or 1 mA) skin threshold (Tskin) which is the level at which the stimulation is first felt and slightly below maximum tolerance (Tmax) which corresponds to the level at which a user experiences discomfort or pain. A signal may also be defined to rove between Tskin and Tmax, by continuously or periodically adjusting amplitude, stimulus pulse width, and/or period as may be defined for a sinusoidal waveform.

In an embodiment, a system component such as the neurostimulator or programmer determines the therapeutic protocol for a given week or longer periods using a predefined schedule stored in its memory. The schedule may be modified according to various factors such as time since the first therapy session, number of stimulation sessions provided since the start of therapy, rate of stimulation sessions provided since the start of therapy. Additional adjustment may be made based upon assessment of patient input data which indicates improvements, worsening, or no change in symptoms as calculated upon patient input data.

In embodiments, at least one system component operates at least one accelerometer and is configured to analyze the accelerometer data to determine if a user is active or ambulatory using at least one of activity data and orientation data. The accelerometer data maybe analyzed to determine if the patient is, for example, walking, getting out of bed, moving with a gait that is over a selected rate. In this case, a modification to the system may adjust operation such as pausing or decreasing the provision of stimulation until the accelerometer data indicates that the user has stopped being active (e.g. the data remains below a selected movement threshold for a selected interval).

In embodiments, the instructions may also incorporate methods and guidelines reviewed in other parts of this specification. Additionally, because SAFN stimulation at the level of the knee can be used to treat individuals with pain, the kit may be indicated for providing relief from both pain and OAB symptoms. In this instance the instructions that are provided within the kit may instruct a user select the treatment mode related to the desired therapy and may also instruct to position electrodes or an electrode array differentially.

In an embodiment, a method of treating an overactive bladder of a person suffering symptoms of the disorder includes the steps of applying TENS electrodes for stimulation 260 which can include establishing at least two transcutaneous electrical neural stimulation (TENS) electrodes 30 and establishing a neurostimulator 10*a* configurable to provide a treatment stimulation signal to the TENS electrodes according to a stimulation protocol that is defined in, or selectable using, a stimulation module 54 for stimulation of the SAFN for the treatment of the patient's OAB symptoms. This also includes positioning at least one of the two TENS electrodes on the inner side of the patient's leg 6 in the area near the upper calf. An assessment procedure 262 can include the steps of actuating said neurostimulator 10*a* to provide a test stimulation signal and assessment to determine if at least one of a tingling, vibrating, buzzing, pressure, electrotactile tactile sensation, warmth, or tickling sensation is experienced which radiates away from the location of at least one of the two electrodes. In the assessment 262 two steps may occur which include (1) when application of the test stimulation signal fails to produce a radiating sensation indicating that the saphenous nerve has been stimulated, then performing the step of either increasing the test stimulation signal or adjusting the position of at least one of the two TENS electrodes and (2) when the test stimulation signal produces the radiating sensation, then providing stimulation treatment 268 using a stimulation signal strength which is not painful to the patient. The strength can be iteratively assessed or adjusted during therapy in the case that the patient's threshold for pain changes.

In the method, the step of determining whether a sensation occurs may include the step of determining if the sensation is radiating away from an electrode and down the leg towards or into the foot. Alternatively, the application step may include the steps of providing instructions to place, or placing, a second lower electrode so that it is vertically displaced from the first electrode and near the medial malleolus or the sole of the foot and determining if a sensation occurs which can be either radiating away from the first electrode and down the leg, or away from the second lower electrode and up the leg. The term "vertically displaced" signifies that one electrode is offset longitudinally along a limb relative to another i.e., it is more caudal or distal.

The method may also include the step of providing user instructions, or instructing a user directly, and these can be related to actuating said neurostimulator to provide a test stimulation signal and perform assessment 262 and providing stimulation with various protocols 268. The user instructions can include at least one of: written instructions; illustrations of the leg with graphical depictions of the location on the medial surface of the leg where the TENS electrodes should be placed; illustrations of the leg with graphical depictions of the location on the medial surface of the leg where a TENS array should be placed; instructions provided by a mobile device app or a mobile device; an audio-message of instructions; verbal instructions; instructions to use a device such as an ultrasound, infrared, or electrical impedance device in order to locate the saphenous nerve or saphenous vein; instructions provided in combination with either a virtual reality or holographic display; instructions provided by a mixed media technology such as a DVD, and, a website address where user instructions are provided. User instructions include directions to use landmarks such as anatomical landmarks or markings made on the skin (e.g. tattoo) that indicate the positioning for at least one TENS electrode.

In the method, at least two TENS electrodes can be realized as part of an accessory such as an electrode array 270 that positions the electrodes on the medial aspect of a patient's leg, or a garment 220. Additionally, when the at least two TENS electrodes are realized within an electrode array 270 that is designed to be connected to at least one band 276 that is configured to be wrapped around the calf of a patient and to position the array vertically along the inner side of the leg and the first electrode is above the second electrode. The band may be configured to wrap around the area of a patient's upper calf to secure and bias the electrode to the calf. The band or garment 220 can be configured to be attached to at least one electrode and to wrap around the area of a patient's upper calf, mid-calf, or entire leg to secure and bias the one electrode to the area between the upper calf muscle and the tibia.

The method may further include providing or operating an external patient programmer 70 which is configured to communicate with and provide user control of the neurostimulator and at least one of the neurostimulator and external patient programmer are configured to monitor usage and assess compliance with respect to a treatment program that is related to treatment of overactive bladder and to provide patient alert reminders related to a stimulation program that is defined for the treatment of overactive bladder. Additionally, at least one of the neurostimulator and external patient programmer are configured with a user interface module 80 configured to query about bladder activity, bladder pressure, urinary leakage and/or urgency episodes measured by wearable or implantable sensors. In an embodiment, at least one of the neurostimulator and external patient programmer are configured to query the patient about a symptom characteristic such as urgency, urge incontinence or frequency related to overactive bladder symptoms and to store the responses. Further, at least one of the neurostimulator and external patient programmer are configured to allow the patient to input information related to a bladder diary, including if a void event was associated with urgency or leakage. These may also be configured to query the patient to input information about whether any voiding events occurred during sleep, whether voiding events awoke the patient, or whether voiding events were accompanied by urgency and/or leakage.

The method can further include setting, instructing, or providing instructions related to setting a stimulation protocol that is defined for stimulation of the SAFN for the treatment of OAB which includes setting the stimulation signal to be at least one of: a signal between 5 and 20 Hz, a 10 Hz signal, a 20 Hz signal, and a signal that roves between 10 and 20 Hz. The stimulation signal can be defined in the stimulation module 54 to be at least one of: skin threshold (Tskin), maximum tolerance (Tmax), and a signal that roves between Tskin and Tmax, by continuously or periodically adjusting amplitude, stimulus pulse width, and/ or period in the case of a sinusoidal waveform.

The method can also include an external patient programmer 70 that is further configured to graphically display data related to overactive-bladder-related symptoms as summary statistics or trend charts. The external device or programmer 70 can also determine the therapeutic protocol for a given week or longer periods using rules or lookup tables of the compliance module 200 based upon factors such as time since the start of therapy, number of stimulation sessions provided since the start of therapy, rate of stimulation sessions provided since the start of therapy, and improvements, worsening, or no change in symptoms as calculated upon patient input data.

The method can also include providing and operating an accelerometer for at least one system component and the system 10a is configured to analyze the accelerometer data to determine if a user is active or ambulatory by using at least one of activity data and orientation data. The accelerometer data may be analyzed to determine whether the patient is, for example, walking, getting out of bed, moving with a gait that is over a selected rate. In this case, the system may modify operation such as pausing or decreasing stimulation until the accelerometer determines that the user has stopped being active.

In an embodiment a system for transcutaneous electrical nerve stimulation in humans includes a housing 12 a stimulation module 54 having stimulation generator mounted within the housing for electrically stimulating nerves and an electrode array 270 releasably mounted to the housing and connectable to the stimulation generator, the electrode array comprising a plurality of at least two electrodes 30 for electrical stimulation of nerves. The user interface module 80 can provide at least one user control 16 mounted to the housing and electrically connected to a user interface module 80 working with the control module 52 to control the stimulation generator for controlling at least one characteristic of a stimulation signal generated by the stimulus generator. The sensing module 55 can provide monitoring circuitry mounted to the housing 12 and electrically connected to the stimulation means for monitoring impedance in order to assess electrode contact with patient skin 6. A user interface module 80 mounted within the housing 12 and electrically connected to the control module 52 for controlling the stimulus generator. A user display can be part of the interface module 80 and mounted to the housing and electrically connected to the control user interface module 80 and the monitoring circuitry of the sensing module 55 for displaying the status information related to the device 50a. At least one strap 276 can be attached to at least one of the housing and the electrode array 270 and the strap is configured to hold at least one of the housing 12 and the electrode array 270 so that the array stimulates a specific anatomical location to treat OAB by stimulation of the SAFN using at least two longitudinally displaced electrodes 30. Preferably, the location is the medial surface of the upper calf area between the calf muscle and the tibia.

In an embodiment, a treatment regimen compliance system has a control module 52 with a processor configured for providing the control operations to occur according to a treatment regimen. The treatment regimen includes a treatment schedule with days and times related to when therapy events are scheduled to occur such as the provision of stimulation, taking of medication, surveying of the user with selected survey materials, presentation of videos that may reinforce healthy habits, behaviors, or cognition, use of digital health tools such as software programs that engage the user and which relate to therapy for various disorders, and even the presentation of digital games that reinforce concepts related to therapy. At least one neurostimulator 50a, 300 is functionally coupled to the processor and configured to communicate data or control signals to and from the processor. For example, the neurostimulator may keep a log of use and can communicate this log to the control module so that the compliance module can update the history of therapy and evaluate the history to determine if one or more compliance criteria are being met. The processor can be part of the neurostimulator 50a or exist in other system component such as the user/physician programmer 70. The control module 52 is configured to access an established treatment regimen for a patient, or allow the establishment of a programmable treatment regimen and to control a compliance module that is configured for calculating a measurement of compliance for at least one characteristic of the programmable treatment regimen. The programmable treatment regimen is defined for at least neurostimulation provided by at least one neurostimulator 50a. Further, at least one user notification module 360 which operates as part of the user interface module 80 is functionally coupled to the control module 52 and configured to provide a notification signal to a user related to compliance of the programmable treatment regimen. The notification signal is sent responsive to at least one notification rule. The system also includes at least one external patient/physician device 70 configured to present notification signals, accept user input data, and communicate data or control signals with the processor. The compliance module 200 is realized as a module of a neurostimulator 52a, patient/physician device 70, or other system component 70' and can be realized as distributed across both the neurostimulator and patient/physician device.

Figure 16:
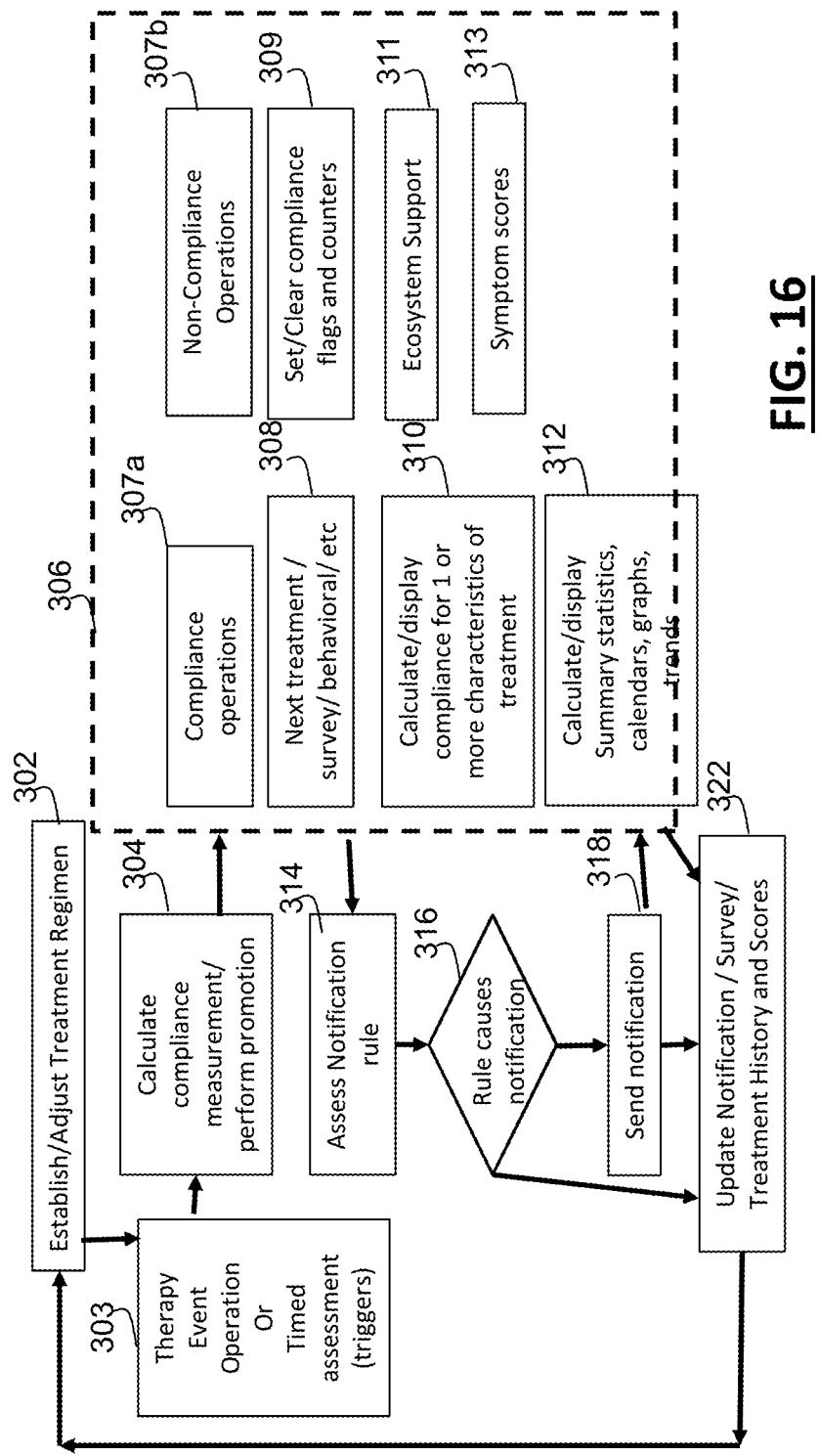
FIG. 16 shows an example of a method for assessing compliance and contingently adjusting treatment events and operations.

In an embodiment, as shown in FIG. 16, in step 302 a treatment regimen is established or updated which includes regimen parameter values related to, for example, when treatment events occur or how many of a particular treatment event should occur. The treatment regimen defines a minimum required or maximum suggested dose of stimulation to occur over an interval, such as 30 minutes at least twice a week. Alternatively, the regimen is defined more specifically such as including a treatment schedule associating particular days and times with treatment events. The compliance module 200 analyzes data in the programmer 70 or neurostimulator to assess compliance for a given compliance measurement. For example, a neurostimulator 50a is functionally coupled to the processor and configured to communicate data which is analyzed by the compliance module 200. The neurostimulator 50a keeps a log about treatments it has provided which is communicated to the control module 52 so that the compliance module can update and assess the history of therapy for a user. The control module 52 operates the compliance module 200 according to triggers 303. For example, the triggers can occur periodically, when a therapy event occurs, or is scheduled to occur in the near future (e.g. 1 hour in the future), or in a time/scheduled manner so that it evaluates the history of treatment events to determine if one or more compliance criteria are being met 304. When the compliance module calculates a measurement of compliance for at least one characteristic of the programmable treatment regimen, then contingent operations occur 306.

The compliance module 200 is configured to operate according to compliance rules defined for contingently modifying system operations 306, such as the operation of a neurostimulator, user/physician programmer, or other system component based upon assessment of compliance 304. For example, various operations are defined contingently such as compliance operations 307a that occur when one or more compliance criteria are met and non-compliance operations 307b which occur when one or more non-compliance criteria are met. A contingent step may be defined to occur both in the case where a compliance criterion is met or where a non-compliance criterion is met. For example, in step 308, a next scheduled treatment event may be rescheduled in the case where a stimulation treatment session was not provided by a user within 2 hours of the scheduled time. Alternatively, step 308 can cause a scheduled stimulation session scheduled for the late afternoon to be cancelled if a user provided a stimulation session earlier on that same day. In step 308 the earlier stimulation session would permit the compliance criterion to be met and also prevent a reminder alarm from being triggered later in the day at the time of the originally scheduled treatment session. In step 309, counters and flags are set, reset (i.e., cleared), or updated in the user log of memory module 60 so that the compliance criterion are evaluated as true or false according to the current status. A historical record of flag parameter settings is also be updated in the user log in this step. In step 310 compliance status for at least 1 characteristic of the treatment regimen is calculated and displayed. For instance a scheduled treatment for a particular day may be given a status of compliant if the patient has provided stimulation above a minimum threshold value. Additionally, in step 312 summary statistics for compliance as calculated across multiple treatment events are derived and displayed.

The evaluation of compliance and non-compliance criteria may occur using rules defined in look-up tables, algorithms, equations, and can combine across multiple criteria using Boolean logic. For example, a non-compliant contingent operation may be defined as part of a rule of step 307*b* which triggers a subroutine of step 311, which includes ecosystem support operations such as presenting a short video to the patient on the importance of compliance. This may be triggered only if a treatment criterion requiring a minimum of three stimulation treatments a week is not met AND also this criterion was not met for the prior week.

The control module the implements step 314 where a notification rule is assessed by a notification module 360. If the rule determines that notification should be sent according to a notification rule, then a notification signal is provided to a user 318 that is related to compliance status. The notification signal is sent responsive to at least one notification rule, for example, the rule may specify that if non-compliance exceeds a selected threshold then a notification is also transmitted to a doctor, insurance company, or medical service, rather than only to the patient. The notification can occur using the external patient/physician device 70 that is configured to present notification signals, accept user input data, and communicate data or control signals with the processor, can be provided on the neurostimulator 50*a*, and/or other system components. The notification module 360 operates at least partially under control of the compliance module based upon assessment of at least one parameter defined for treatment regimen operations or events according to the notification rules. Alternatively, if the rule does not dictate that notification should be sent step 322 occurs where the history treatment events (e.g. stimulations, notifications, surveys) and compliance flag status's are updated and housekeeping of parameters values occurs.

In an embodiment, a parameter defined for treatment regimen that is assessed in step 304 is a compliance measurement that assesses whether a defined stimulation dose (e.g. a duration of stimulation using at least a minimum stimulation amplitude) has been provided within a selected time interval. For example, two stimulation sessions each lasting at least 30 minutes have occurred over a prior interval such as the past week. Alternatively, the compliance measurement 304 assesses compliance about whether a defined set of questions has been provided and then answered sufficiently to meet a criterion (e.g. questions about bladder symptoms such as bladder urgency were answered within a selected time interval such as 10 minutes from when the user was prompted and/or at least a percentages such as 75% of the questions were answered). Alternatively, the compliance measurement 304 evaluates compliance for playing/viewing a defined set of training videos, multi-media clips, or verbal or textual instructions and reminders. If a criterion such as that one or more of these should be provided to the user at least 3 times within a selected time interval such as the first 2 weeks of treatment then in step 311*a* video may suggested to the user. Training videos include use of a neurostimulator during treatment (e.g., application of electrodes, setting stimulation signal parameters, how to use features of the software, such as video-conference with medical service support (and what to expect), replacing disposable components, etc) or management of a disorder. In the case of overactive bladder, the videos may promote lifestyle changes such as drinking less before bedtime, anxiety, the videos may be designed to promote relaxation. In the case of depression, the videos can provide cognitive behavioral therapy. In the case of non-compliance, after a user is provided with a notification 318, the user can then be prompted to correct the non-compliance such as by allowing a non-compliance operation to occur 324, such as viewing a video, providing treatment, etc. as provided by the multimedia module 366. Training videos may also be supplied by the ecosystem module 368 which provides ecosystem features such as video instruction, virtual meetings, lifestyle reminders and other features in collaboration with other modules of the system. In the case where a user provides an amount of stimulation that exceeds maximum suggested dose, the non-compliance operation that is contingently invoked is that a video may be presented to the user that explains harm that may occur due to exceeding the recommended stimulation dose such as skin irritation or bladder retention in the case of treatment of OAB. The video may be presented on the programmer 70, or may be viewed on a smart-TV which sends a signal to the communication module 68 of the system so that this therapy event is registered. Similarly, if the video is requested through a voice service (e.g. Alexa) to be viewed by a user, then the system may communicate with the accessory providing the voice service in order register the occurrence of the therapy event.

In an embodiment, another parameter defined for treatment regimen operations for which a compliance measurement is assessed 304 is for a defined set of messages about lifestyle changes that is scheduled to be viewed a selected number of times within a selected time interval. For example, during the first month of therapy which serves as an induction period, the regimen has a parameter value that is set which dictates that treatment includes viewing messages concerning lifestyle adjustments conducive to treatment benefit (e.g. avoiding coffee) at least twice a day. This parameter value can be can increased or decreased depending upon changes in symptoms that are input to the system as user input data over time.

In an embodiment, another measurement of compliance that occurs in step 304 relates to at least one characteristic (e.g., duration of uninterrupted stimulation, stimulation signal amplitude, stimulation provided during sleep) of a programmable treatment regimen for at least one neurostimulation treatment defined in the regimen for at least one neurostimulator, and includes determining if a compliance criterion has been met which includes a minimum stimulation dose delivered across a selected time interval or a minimum number of treatment sessions (e.g., 3) lasting minimum defined period (e.g., 30-180 minutes) have been delivered within a selected interval (e.g., one week).

In an embodiment, the notification rules, definitions of compliance and non-compliance criteria, contingent operations, and rules to assess measurements of compliance and non-compliance of at least one characteristic of a programmable treatment regimen occur using operations and parameter values defined in one or more lookup tables. The compliance measurement definitions allow for determining, for example: compliance in not exceeding maximum number of treatment sessions lasting a minimum defined period within a selected interval; compliance in not exceeding a maximum defined dosage within a selected interval; compliance in alternating stimulation sites between the two sides of the body or two sites after a selected interval of stimulation, as defined by a stimulation location criterion; compliance in replacing disposable stimulation pads within a selected interval, as defined by a replacement of disposables criterion; compliance in executing a scheduled a doctor visit at a clinic or a virtual visit using a web-meeting medical assistance module 362 within a selected interval, as defined by a check-up criterion; compliance in performing a minimum number of defined behaviors such as such as performing kegal exercises, electrically assisted intravaginal stimulation, within a selected interval, as defined by a user behavior criterion; compliance with respect to a medication regimen that is intended to occur over the same time period as the neurostimulation, as defined by a medication criterion; compliance with respect to a digital health regimen that includes being engaged daily or weekly using digital health software programs, as defined by a digital health tools criterion; compliance with respect providing stimulation within selected intervals of scheduled treatment times, as defined by a latency criterion; and, compliance with respect providing stimulation according to a minimum number of scheduled treatment times that are scheduled to occur at night, as defined by a therapy criterion.

In an embodiment, the measurement of compliance 304 is for neurostimulation defined for at least one neurostimulator, and includes determining if a compliance criterion has been met for at least one stimulation session and graphically displaying a status result that indicates whether the criterion was met or not as defined in the compliance operations 306.

In an embodiment, the measurement of compliance 304 includes determining if a compliance criterion has been met relating to a treatment regimen operation that occurs contingently based upon at least one of the following: according to a calendar schedule, or according to the presence, absence, severity, change, or trend of patient symptoms. A change or trend in patient symptoms is evaluated for a history of at least one reference data value such as provided by user input or sensed data. The compliance criterion can also be assessed according to both a calendar schedule and symptom changes from a previous period. For example, compliance to the calendar schedule is assessed with more "relaxed" criteria (e.g. allowing for a greater number of scheduled stimulation treatments to be missed before non-compliance flagged by the system) if a patient has experienced a larger improvement from baseline and will still experience symptom improvement even if not fully compliant with treatment.

In an embodiment, the measurement of compliance 304 is evaluated for receiving user input data to or more questions contingently presented to a user for example, based upon history of symptom improvement, time since beginning the course of treatment, or the combination.

In an embodiment, parameters that are defined in the compliance module are adjusted contingently upon whether the user provides or fails to provide a treatment event (e.g. a stimulation treatment) that meets a schedule or in response to a notification signal. For example, the schedule of the treatment regimen that defines scheduled doses of neurostimulation can be adjusted in step 308 according to whether treatment was provided by the user. For example, a missed scheduled treatment session can be rescheduled so that a dose is still realized, or if a session is provided by the patient earlier than that scheduled, the scheduled session can be cancelled. Accordingly, the provision of user notification to prompt stimulation under control of the compliance module for the later session is cancelled so that this does not annoy a user unnecessarily. In the event of a missed or incomplete treatment session, the compliance module may provide reminder alarms, reschedule for next day, notify the user that they provided stimulation that was insufficient to meet a dosage or session criterion and it will be rescheduled. Further, a compliance criterion relate to dosage may implement a substitution rule that relies upon total dosage over time. For example, if a user provides 60 minutes of stimulation instead of 30, and the stimulation session is defined only for 30 minutes, then the stimulation session and associated reminder that were scheduled for the next day are cancelled.

In an embodiment, the treatment regimen includes an established treatment schedule 302 that is adjusted by a compliance algorithm of the compliance module 200 as realized by the compliance and non-compliance operations 307a, 307b and also by evaluation of patient input data related to symptoms. The evaluation of symptoms occurs in step 313, which provides status on symptom presence, absence, or severity. For example, in the presence of symptoms or if severity is above a selected amount then an induction treatment schedule may be extended and longer stimulation sessions may be used.

Alternatively, in the absence of symptoms or when severity is less, the treatment schedule defined for various treatment events can be made less frequent and sessions may be set to 30 minutes. A change in symptoms reflected by a change score calculated as the amount of improvement or worsening of at least one current symptom score compared to a reference symptom score (such as a baseline score assessed at start of therapy) may also cause an adjustment of the treatment schedule 302 according to treatment regimen rules with respect to a duration or dose of stimulation scheduled to be provided within a defined interval. This can also cause a change in the criteria and rules used during compliance assessment 304.

In an embodiment, notification signals provided to a user as part of step 318 occur according to at least one notification rule that is set in relation to a defined neurostimulation schedule with dates and times. Alternatively, an adjustable neurostimulation schedule is used which is adjusted as a function of elapsed time since a prior treatment. The schedule may also be adjusted due to symptom severity, with more or longer sessions scheduled for more severe symptom scores or less/shorter sessions scheduled after a symptom improvement above a selected level occurs. The schedule can also be adjusted due to an evaluation of the history of neurostimulator usage in relation to meeting a dose criterion. The notifications based upon treatment schedule are adjusted, for example, as a function of elapsed time since last treatment and a score calculated upon patient input data about symptoms that serves as a proxy for presence, absence, or size of symptom improvement.

In an embodiment, the notification that is provided to a user according to at least one notification rule occurs at times defined to be at, prior to, or after dates and times when stimulation is scheduled. Alternatively, the notification occurs at a user-selected, doctor-selected, or default setting which is an interval that occur before, or after expiration of at least one inter-treatment interval defined in the treatment regimen. When notification occurs after missing the scheduled treatment session, this is prompted by failure to provide the stimulation within a selected time after the scheduled day and time.

In an embodiment, the treatment schedule is adjusted by a treatment regimen algorithm using patient input data that is received within a defined interval. The patient input data is compared to data obtained during a reference interval about a subjective score, for example, related to symptoms. The adjustment is defined in a look-up table 350 of the control module for symptom improvement, no change in symptoms, and symptom worsening. For example, in look-up table 350 the treatment regimen allows for adjustment of the treatment schedule from 7 days a week to 3 days a week at either 4 or 8 weeks if a quality of life score has improved by at least 20 or a bladder diary score has improved by 10.

In an embodiment the compliance module is configured to calculate a measure of compliance in steps 304 or 312 over at least one interval such as a day, several days, a week, a month, a year, since the beginning of therapy, or other interval of interest (e.g. during induction or maintenance, etc). Appropriate criteria are used to determine compliance for these different periods such as criteria defined for daily compliance, nightly compliance, weekly compliance, monthly compliance, induction compliance, etc. The notifications provided in step 318 are contingent not only on compliance measurements 304 but also upon a schedule that is adjusted as a function of time (e.g. more notifications may occur earlier on in the therapy regimen such as during induction or as a function of symptom severity. In addition to the notification schedule, the notifications content be adjusted as therapy progresses or based upon symptoms or symptom changes, with respect to obtaining patient input about various aspects of symptoms. For example, if a patient does not indicate a symptom related to nocturia, or the answers consistently do not reflect a change, then a notification rule can cause questions about nocturia to be removed from those presented to a patient. Alternatively, the notifications provided to a user may be adjusted to be more relevant to a user and may promote relevant patient behavior. For example, if nocturia is a symptom, then notifications can be sent about going to the bathroom before bed.

In an embodiment, the user notification module 360 is configured provide notifications related to prompting or reminding selected user behaviors. The notifications for treatment of OAB include, for example, reminders to: attempt voiding before an event such as leaving the house or going to bed; performing pelvic floor exercises; reduce fluid intake; reduce fluid intake after a certain time such as during the evening: take medication; and, provide user input data relate to objective or subjective measures such as symptom severity. In the treatment of various disorders, the severity of a measure may be related to related to overactive bladder symptoms, anxiety, depression, or both. User input related to objective measures may include input of a measurement such as blood pressure if the system is not able to sense this measurement automatically, for example, using a device incorporated into a smartwatch-like form factor that is worn by a user (e.g., Samsung Gear X, Omron HeartGuide) or other manner.

In an embodiment, the treatment regimen or compliance criterion defined for the provision of neurostimulation is modified based upon a user's compliance for the provision of medication. For example, if a patient shows increasing non-compliance for a medication then the dose of stimulation can be increased to compensate. Unlike medication, increasing the dose of stimulation may be accomplished without causing large side-effects. While a patient should not typically take 5 doses of medication on a particular day if they missed taking a medication daily, providing 5 hours of stimulation instead of one can be done to attempt to compensate when a user does not provide a daily course of stimulation. Likewise, increasing peripherally supplied stimulation duration may be helpful when users fail to be compliant with medication. Similarly, a treatment regimen or compliance criterion for providing medication treatment according to a medication treatment schedule may be decreased based upon neurostimlaution dosage provided over a selected interval and/or an assessment of compliance related to the provision of an ongoing course of neurostimulation, and or assessment of symptoms. In other words, the provision of more stimulation can entail a decrease or eventual stopping of a medication dose, as long as symptoms do not worsen. Although the dose of stimulation may be increased, clearly with respect to duration or number of stimulation sessions and less so for amplitude, an upper limit to stimulation may be used simply to deter side-effects such as skin irritation and accordingly the compliance module 200 is configured to operate to assess 304 and realize compliance restrictions to deter this. These restrictions are defined according to interval rules and preventing the provision of stimulation during a single session or across sessions from exceeding a defined duration within a selected interval. The restrictions can be defined and assessed in step 304 using interval-strength rules that take into account amplitude and do not permit a user to provide a dose of stimulation that exceeds a defined maximum dose within a selected interval. In the case of non-compliance the operation 307b causes the neurostimulator to be deactivated and a message provided to a user 318 disclosing the reason for this action.

Alternatively, the notification is sent 312 to a remote clinic or doctor computer 71 using a communication module so that compliance can be assessed, and the doctor may choose to increase the maximum allowable stimulation dose after talking with a user. The neurostimulator or user/physician programmer 70 or other system component is configured so that parameters are adjusted in the treatment regimen and compliance module 200 by clinician using a clinic computer. Other types of non-compliance may be defined to cause the system to restrict use. The compliance module 200 is further configured to operate according to compliance rules that are defined to cause the compliance module to cause the control module to disable the stimulation operations provided by a stimulation module 54 of the neurostimulator if at least one compliance criterion is assessed as false because the criterion was not met. At home therapy requires the cooperation of a patient, and use can be restricted, for example, if a user fails to provide patient input data about symptoms so that therapy benefit can be tracked accurately by a physician monitoring a user remotely. Accordingly, the compliance module is further configured to operate according to compliance rules defined for non-compliance operations 307b that cause the notification module to communicate a notification signal 318 to a computer operated by third party such as a doctor or medical monitoring service if the patient does not meet at least one selected compliance criterion.

In line with the need to have a user actively participate during at-home therapy, the compliance module 200 is further configured to operate according to compliance rules in the non-compliance operations 307b that cause a restriction in the user/programmer 70 that withholds permission of communication with, or provision of stimulation by, a neurostimulator until selected outstanding or omitted user input data is received. The user input data may include, for example, one of the following: input data related to presence, absence, or severity of symptoms; input data related to information scheduled to be input by a user; input data including an activation code provided to re-activate the system after a flag status has been set to false (the patient was non-compliant for treatment or subscription/token payment); input data related to a code on a disposable stimulation pad; and, input data scanned in or received by RFID or otherwise for a system component or disposable.

When a user schedules at least one treatment event such as a session (by selecting a day of the week, time, and treatment duration that serves as a recurring scheduled treatment of the treatment regimen) then the compliance module compares treatment event history against the treatment regimen to determine compliance 304. The system can be configured to query a user to select the parameter for a recurring scheduled treatment when the systems is first used by a user, or at a time thereafter. The establishment of a treatment regimen 302 and monitoring of compliance 304 may be done using a treatment regimen that is defined for an implanted neurostimulator, an external neurostimulator, or the combination, as may be defined by selecting appropriate controls 180. In the case of combination treatment using more than one neurostimulator such as an implanted and external treatment regimen, the compliance module calculates compliances for a treatment schedule which includes the combination of a first treatment provided by at least one implantable neurostimulator and at least a second treatment selected from the group of: treatment provided by a percutaneous neurostimulator with a needle stimulator; treatment provided in conjunction with an intravaginal stimulation device; treatment provided by a magnetic pelvic floor stimulation device; treatment provided by a transcutaneous electric or magnetic stimulator; treatment provided by a pelvic floor stimulator; treatment provided by pharmaceuticals as may be indicated by at least one of: patient input, electronic tracking or communication related to the provision of pills, delivery of injected drug, cutaneous drug delivery systems, drug eluting patches, or implantable drug delivery. The compliance module can be configured to adjust the second treatment schedule based upon provision of the first treatment, or vice-versa. For example, if an external treatment is provided that exceeds a defined dose then the implanted treatment schedule may be adjusted to provide a decreased dose of stimulation. In this manner, if the user provides sufficient stimulation by an external stimulator then the implanted neurostimulator 300 can save battery by decreasing its stimulation. The implantable neurostimulator can serve as a back-up if a user fails to provide sufficient stimulation using an external neurostimulator.

In an embodiment, the notification signal provided in step 318 is an auditory, visual, textual, vibrotactile, or multimedia message provided by the notification module 360 or is a digital signal transmitted by wired or wireless protocols of the communication module 68. The notification step 318 can also include accepting user input in response to the notification and operating based upon the user input data. The notification module 360 is configured to interact with a communication module 68 which communicates with voice service technology such as Alexa™. In turn, the voice service then operates at pre-defined times to cause notifications to be provided using either auditory notification signals over its speakers or visual notification signals, or both. For example, the voice-service may present a message to a user using a smart appliance such as a smart-TV, user smartphone, smartwatch, or other smart interface. The voice service technology is also configured to receive a user vocal response or other user input (e.g. response provided using a gesture sensed by a video camera of a smartphone) that is provided in response to the notification. In an example, at least one of the following responsively occurs during the notification operations: the user is asked and answers a question prompted by the voice-service within a selected interval or the user is notified stimulation is scheduled to occur and confirms or rejects this beginning of a treatment session; the user provides a verbal instruction that controls therapy by causing the voice service technology to transmit or control the transmission of a command signal that is intended for reception by an external user/physician programmer 70, system component, or external or implanted neurostimulator; and, the user provides vocal instructions that are received by the voice service technology which instructs the system to provide an additional reminder at a future time when the elapsed time since last stimulation treatment exceeds a clock value measured by the control module 52.

In an embodiment, the compliance module is configured to maintain a historical record of treatment events, parameter values, and compliance status flags and states that are related to assessing compliance. It evaluates the historical record using at least one compliance criterion 304 that can assess compliance for a treatment event type across a selected interval such as weeks, months, etc. The historical record includes information such as: parameters of stimulation treatment that has been provided; treatment events provided according to a treatment schedule; user behavior (e.g., drinking, voiding) and user activity (e.g., sleeping, walking) data obtained by user input or sensing; other types of user input data and sensed data; and, a history of treatment events such as notification messages provided to a user.

The compliance module is configured to use the historical record to track compliance over time to generate summary statistics and trend graphs. Assessing the log history allows determination of whether a patient meets at least one compliance criterion related to multiple therapy events. The historical record is used for adjusting a treatment schedule and similarly adjust the compliance rules and criteria used to assess compliance in relation to the schedule or used for selecting compliance criteria from a lookup table and is used to calculate and displaying statistics related to at least one compliance measure 312. The historical record can also be used to adjust notification parameters related to the provision of notification defined in relation to successfully meeting or failing to meet at least one compliance criterion.

For example, if a history of non-compliance for a treatment event is detected, the notifications can be increased for that event. In an embodiment, a notification parameters and rules look-up table 352 of FIG. 18 dictates that the maximum number of reminders that occur if the provision of stimulation does not take place is 3. If evaluation of a historical record of compliance determines that the patient is non-compliant for providing stimulation during (e.g., non-compliance has occurred for at least 4 of the prior 8 weeks) then the maximum number of reminders sent due to a missed treatment session can be increased to 5.

Table 352 of FIG. 18 shows an illustrative embodiment of notification parameters and rules. For example, during induction notifications are sent 15 minutes before a treatment session is scheduled to occur. If the user does not provide the treatment at the scheduled time then a notification is sent 1 hour afterwards. The notification provided to alert to an upcoming session includes a text message displayed by the neurostimulator or user/physician programmer 70 or other system component. The notification sent if the stimulation does not occur includes both text and auditory signals. A notification rule dictates that the notification occurs a maximum of 3 times, unless the patient has been non-compliant for at least 4 of the prior 8 stimulation sessions, in which case the maximum number of reminder alarms is increased to 5. The permissions is set to "All" which indicates that either the doctor, patient, or caregiver may adjust the parameters of the notification rule. In this example, the notification rule for survey/diary events is set to "text+tone+voice" indicting that if the patient is at home that notification will be provided using text, sound, and also through communication with a voice service if available. In this example, the notification for disposable pad replacement may include these same notification types but additionally include notification in a shopping cart feature of the ecosystem provided by a digital shopping cart module 364.

Therapy Gamification

In an embodiment, the treatment regimen is realized within a game structure. "Gamification" of the therapy includes providing game-like rewards, punishments, and experiences as part of the therapy regimen to promote improved compliance, user interest, and fun. Similar to a game, points may be gained or lost depending upon how well the user "plays the game" which in this case is being a compliant patient and performing behaviors that increase therapy benefit. The rules of the game and point allocations are defined in the regimen, defined by the patient, or doctor depending upon various factors. For example, a doctor may assign a point value to a behavior the has been found to improve therapy outcome in a group of patient or which is designed to cause increased compliance of a behavior for the patient. A scoring method and associated look-up table of points to be used during treatment are shown in FIG. 19 and FIG. 20, respectively.

Figure 19:
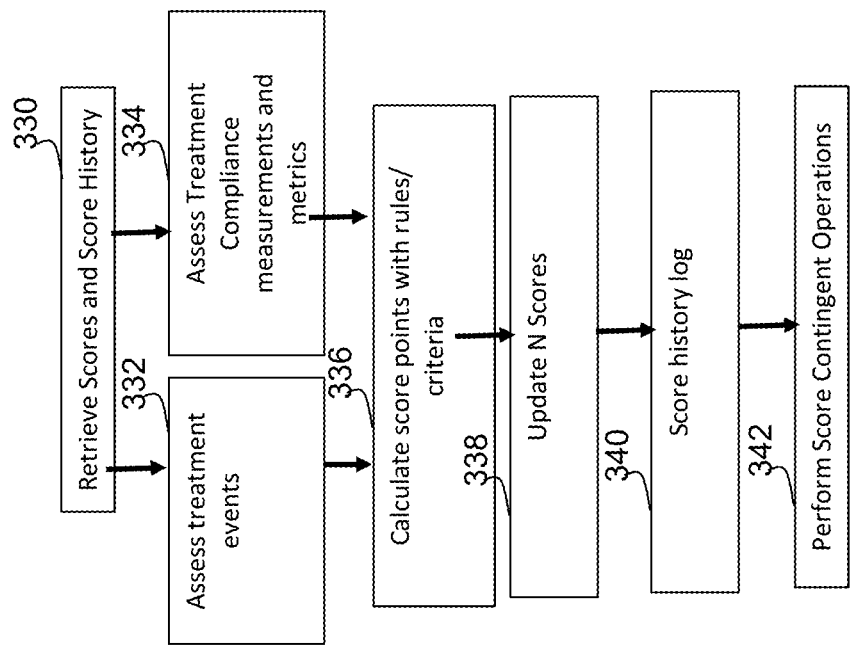
FIG. 19 shows an example of a method related to gamification of a treatment regimen.

As shown in FIG. 19, in an embodiment a neurostimulation gamification system has at least a first processor of a control module 52 that is configured for operating a gamification module 370. The gamification module is configured for retrieving the score and score history of a user 330 which may be invoked by step 322 implemented by the compliance module, invoked directly as part of step 303, or otherwise by the control module 52. In step 332, treatment events are assessed. This assessment can include sensing, detecting, registering, tracking, monitoring, and assessing treatment events that have occurred as well as the event characteristics. The score subroutine also assesses treatment compliance measurements and metrics 334 as well as any flags states that are set as part of step 309. In the next step, the event and compliance data results obtained in steps 332 and 334 are analyzed in step 336 which uses score rules having score criteria to derive score points that result from implementing the score rules. In the next step scores are updated 338, by adjusting at least one score according to at least one score rule based upon event data. This may include updating a global treatment score as well as scores related to treatment events (providing stimulation, answering survey questions provided by the system), compliance, timely replacement of disposables, and use of ecosystem features such as videos, virtual meeting with medical professionals, etc. The score rule calculations use event data measures and associated flag states which reflect for example event occurrence, event absence, event count, and at least one characteristic of an event. The score rule can assess event data in relation to a characteristic of a programmable treatment regimen such as compliance for a schedule of treatment events, using the data from step 334. In the next step 340 the score history log is updated with any changes to scores as well as the reasons for the changes in points (i.e. the results of assessing the different score criteria are stored in addition to the changes in points so that the reasons for the score changes can be reviewed by a medical professional). In step 342 score contingent operations occur. For example, a score is displayed on the housing of a neurostimulator, or is updated on the display of an external patient controller 70 configured to display information including at least one score associated with a game to a user, accept user input, and to communicate data to and from the at least one neurostimulator 52*a* that is functionally coupled to a processor of the control module 52. Other score related contingent operations may be alerting the user that they have won a symbolic award such as a gold star, or "good patients" status. Another score contingent operation can be alerting the user that they have obtained a discount that may be applied to the cost of the treatment or disposables.

In embodiments, a score contingent operation may result in the user obtaining a reward realized as a real-world reward. For example, if the neurostimulation treatment is related to a weight management program, and the user has been compliant with stimulation, then the system can authorize a dessert to be included in the next order of food from a food plan delivery service that is part of the weight management program. In another example, in the treatment of a psychiatric or other disorder, the score results in credit that provides access that allows a user to play a selected video game over the internet for a selected period to provide an incentive when the system is used to provide treatment in children, teenagers, and in cases of treatment of addiction.

FIG. 20 shows an example of a portion of a look-up table 354 that is used by the score rule to determine the points that are used to change a user's score. There are points defined for treatment behavior related to the provision of neurostimulation treatment which include providing a 2 point bonus of the user provides treatment within 1 hour from the time the user is alerted about a scheduled treatment session. Failure to provide the treatment in a timely fashion results in a 1 point decrement. In this example the treatment session is defined as 30 minutes of stimulation, and the user obtains additional points for stimulating for at least 60 minutes or over 2 hours Failure to stimulate for longer than the defined treatment session does not result in any point decrement. Points are also obtained for providing one quality of life set of questions per week, completing one digital bladder diary per month, and answering a short symptom survey on a daily basis. The bladder diary completion results in greater point change because it requires more effort from a user. The symptom survey results in a small increase in points because it is easy, but a larger decrement to incentivize users to complete that task since it is simple and allows symptom changes to be tracked on an ongoing basis. Points are also defined for ecosystem features such as watching videos related to the provision of treatment of lifestyle changes, or using digital software tools such as participating in (leaving comments) in an online community using a software application of the system or conducting a virtual-meeting with a nurse-practitioner who can review the treatment progress with a user and answer questions, etc. Point additions and decrements are also defined for replacement of disposable system components according to a defined schedule or number of uses. The values shown are simply for illustration and can be adjusted by a user, doctor, caretaker, or otherwise in order to promote therapy compliance and behaviors that increase the chance for therapy benefit. The score rules access the point values during their implementation.

In example embodiments, the gamification module 370 is configured for assessing a treatment event by sensing a treatment event (e.g. operating with a sensing module 55 to determine that a blood pressure reading has been obtained or assessing IoT sensor information to determine if a user has gone to the bathroom), detecting a treatment event (e.g. operating with a stimulation module 54 and detecting that a neurostimulation session has been carried out by a user), registering a treatment event (e.g. operating with the survey module 61 to determine the a user has answered a set of survey questions), tracking treatment events (e.g. assessing if a user has consistently provided above a minimum number of stimulation treatments over a prior period of a month), monitoring treatment events (e.g., communicating with a voice services device to monitor that a user has provided user information to the voice service system that is relevant to treatment events), and assessing characteristics of treatment events (e.g. determining the duration of a treatment session) that have occurred and adjusting at least one score according to at least one score rule based upon event data. For example, a score rule can assess event data by evaluating two characteristics of treatment events according to two score rule criteria. The first criterion of the score rule evaluates if a selected number of minimum treatment sessions have occurred for a prior period such as 1 week and the second criterion assess total treatment time for the last week as being over a selected amount. The rule dictates that if the first criterion of the score rule is not met then the score is decremented by 1 point, unless the second criterion exceeds an amount such as 2 hours. Accordingly, if the user provided 3 treatment sessions of 2 hours, 30 minutes, and 25 minutes, then if the first criterion requires 3 sessions of at least 30 minutes each, then this will not be met. However, since the user provided a 2 hour session, the second criterion is met. In this example, score rule results in no decrement to the score, but also no increment since the 3-session criterion was not met. Score rule#1: If score rule #1 criterion #1 is met (# complete treatment sessions for defined interval >2) then increment treatment score by 1 point (treatment score=treatment score+1); AND If score rule #1 criterion #1 is not met (# complete treatment sessions <3) then decrement treatment score by 1 point (treatment score=treatment score−1); AND If score rule #1 criterion #2 is met (total treatment time for defined interval >2 hours) then increment treatment score by 1 point (treatment score=treatment score+1).

In an embodiment, a neurostimulation gamification system comprises a first processor configured for operating a gamification module 370 under control of a control module 52, and a neurostimulator coupled to the processor for control and communication related to the provision of stimulation as part of a therapy regimen. The gamification module 370 is configured for registering and assessing therapy events that have occurred or failed to occur and adjusting at least one type of score according to at least one score rule. The calculation of score adjustment occurs using points derived by evaluation of compliance and event data such that the scores reflect therapy event occurrence, absence, and count. The scores can also be adjusted based upon a characteristic of an event (e.g. duration of a stimulation session), and assessment of event data in relation to a characteristic of a programmable treatment regimen, which may be assessed with respect to compliance or otherwise. The system includes an external patient controller 70 configured to display scores, information related to the score, and other features of a game that is designed to reflect therapy status and progress, as well as user compliance. The external device 70 is also configured to accept user input data and to communicate data to and from the at least one neurostimulator.

In embodiments, the scores result in promotion to a higher status level in a manner that is fun, funny, or amusing to a user. For example, in the treatment of overactive bladder, as a user's score increase, their status may increase from, for example, "Peon of Pee", "Serf of Pee", "Pee Apprentice", "Knight of Pee", "Pee Warrior", "King of Pee", toward a top status of "Emperor of Pee". For a female user the status can be adjusted to "Queen of Pee" etc. As points accumulate, higher status, new game levels, and options unlock. As part of the "Sapho" online community scoreboards or "leader boards" may be shown with individuals who collected the most points. When used in the treatment of disorders such as children with depression or autism, symbolic status may be a serve as a good incentive.

In embodiments, increases in score result in rewards having a symbolic, virtual, or monetary value, or associated with a monitory discount, coupon code, or reward/loyalty points. For example, if the system is configured to provide neurostimulation only when a treatment credit or subscription is active, and this requires a monthly payment, then improved compliance may result in a score increase that leads to a coupon code. The code may be applied directly to a shopping cart module 364 of the system.

In embodiments, the adjustment of at least one score by the gamification module occurs according to at least one score rule that assess event data and occurs using parameters of a lookup table 354 having positive and negative points that are used to change the score. Score algorithms include formulas and rules that may limit adjustment of a score. For example, the score algorithm may restrict a maximum increase in points for a particular therapy event type. This serves to inhibit a user from gaining points through frequent interaction with an online community using the social app of the system, while failing to be compliant for other therapy event types. Restricting points for event types provide an increased balance to how points are awarded by the system. The points shown in the table are examples, and can have programmable point values, where larger values are set by a doctor or patient based upon events that have greater importance to treatment. Point maximums may also be applied to usage data related to a patient providing neurostimulation wherein the usage data is assessed by integrate the amount of stimulation time or dosage that has been provided across a selected time interval. In this case, the total amount of points obtainable by providing many hours of treatment is restricted and cannot substitute for a user being compliant to other therapy event such as providing electronic survey data about symptoms. The scores can also be adjusted according to points associated with a measurement of compliance, and the additional of points may be restricted if a measurement of compliance does not meet a treatment criterion.

When the gamification module is configured for adjusting at least one score calculated based upon the user providing neurostimulation which is assessed in relation to compliance with respect to a defined stimulation schedule, then points are rewarded for adherence to this schedule. Alternatively, there may be no schedule defined and the treatment criterion may simply be that the user provide stimulation at least every 2-3 days and the score value is calculated based upon assessment of elapsed time between stimulation sessions being less than a selected amount. As shown in the table 354, points can be allocated when a notification is provided to a user that stimulation should occur and the elapsed time between the notification and when the stimulation is provided by the user is below a selected amount.

When scores are adjusted based upon compliance with treatment events, points can be allocated to adjust at least one score based upon the user providing or failing to provide answers to at least one set of questions. Further the points may be increased if the user opts to answer a larger set of questions since that will provide a more complete assessment of patient benefit. The points can be allocated based upon completeness of, for example, the user inputting data to a bladder diary or completing items of a quality-of-life survey instrument, with respect to the timing and completeness of the user input data and the schedule of when these data to be input by the user.

As shown in table 354, in the category treatment, the gamification module is configured for adjusting a score if the user provides treatment within an elapsed time from receiving a notification that a treatment session is scheduled. Further, the gamification module is configured for adjusting at least one score based upon the patient providing additional stimulation treatments that exceed a defined treatment program that has been curated to provide a minimum dose required for induction or maintenance of therapeutic benefit. In this case providing a stimulation session of at least 1 hour results in an improved score, with a further point reward if that exceeds two hours.

As shown in Table 354, in the "behavioral category" the scoring algorithm of the control module is configured for adjusting at least one score based upon the patient providing adjunctive therapy such as pelvic floor exercises, as may be registered in the system by user input. If the user learns about pelvic floor exercises by watching videos the point gain is higher since this is being rewarded as a more important behavior. Additionally, the gamification module is configured for adjusting at least one score based upon the patient input data assessed as positive defined lifestyle changes such as reducing amount of coffee intake per week. The gamification module is also configured for adjusting at least one score based upon assessment of the patient input data in relation to the user following a doctor's orders such as performing kegal exercises a minimum number of times per week. The gamification module is also configured for adjusting at least one score based upon scheduling and participating in web-based meetings with medical support staff to review treatment progress and answer questions which in the table is rewarded with 7 points since this is encouraged. Although not shown in the table, the gamification module is also configured for adjusting at least one score based upon the compliance of, or frequency with which, the user provides input related to sensor data such as results of testing the user's blood pressure. Although not shown in the table, the gamification module 370 is configured for adjusting at least one score based upon compliance to a medication treatment regimen which may be obtained by a review of user input data or sensed data about medication delivered to patient orally, by injection, dermally applied, applied via a patch or otherwise.

In an embodiment, the gamification module is configured for adjusting at least one score based upon analysis of data input by the patient or sensed by the system about timely replacement of disposable components according to a schedule and/or regularly recharging a battery of the neurostimulator.

In an embodiment, the gamification module evaluates at least one score that is calculated in relation to at least one score criterion to determine discount or rebate on at least one payment related to cost of disposable products, a monthly subscription payment, insurance, and/or medication. The discount can be provided by providing a user with an electronic credit token or discount code or coupon that is only operable or accepted by the neurostimulation system that is associated with the user. A reward may also be provided as positive benefit, reinforcement of behavior associated with good therapy outcomes which is selected to be increased insurance coverage terms or an extension of a period of service coverage or subscription period. Alternatively, a score can be assessed in relation to at least one score criterion to provide a punishment in the case of non-compliance such as increased cost of co-pay, revocation of coverage, denial of coverage, and change in patient status such as a ranking or status within the game environment.

The present score of a patient can be assessed by the gamification module in relation to at least one score that is evaluated in relation to at least one score criterion and results in the user earning score points, award badges, improved patient status. The gamification module also can present the current score and progress graphically to patients so that they can view their progress toward achieving at least one treatment goal set for the patient. The graphic presentation may also provide a table of rewards that are contingently tied to the accumulation of points. Treatment goals may be defined for the patient and related to various treatment event types such as user adherence to the provision of treatment according to a regimen, compliance with answering survey item data, provision of sensed data with the assistance of the user, and other treatment event types.

In embodiments, the compliance module, gamification module, and other modules of the system are related to the provision of therapy regimen which includes using an external neurostimulator or controller in the treatment of disorders including for example, migraine, headache, depression, pain, a sleep disorder, insomnia, a psychiatric disorder, an anxiety disorder, an unwanted medical condition, disorder, or patient state, a movement disorder, tremor, a cardiovascular disorder, a blood pressure disorder, arrhythmia, a disorder which is treated by modulation of the vagus nerve, median nerve, and/or a disorder treated by stimulation of a nerve of a lower limb of the patient. Additionally, the treatment may also be related to at least one of: addictions, substance use disorder, opioid use disorder, insomnia, psychiatric disorders including depression, schizophrenia, anxiety, traumatic brain Injury, epilepsy, a cognitive disorder or unwanted cognitive state, Alzheimer's, dementia, PTSD, movement disorders, Parkinson's, multiple sclerosis, Autism Spectrum Disorder, attentional disorder, oncology disorder, inflammation, and gastrointestinal, cardiac and respiratory disorders. The system can also be used to promote a healthy state, to improve performance, or during rehabilitation. For example, an athlete can use the system using during training to improve performance or for rehabilitation from injury. While not treatment a disorder such as stroke, the system can be used to assist with recovery of function.

The modules described for the apparatus 50 are for illustration purposes only and the subject invention can have less than or more than the modules and system components described in this specification, or can be realized in alternative embodiments. For example, rather than having a protocols and parameters module 66, the information related to stimulation protocols and parameters can be simply stored in the memory module 60. Disclosed components and modules may be omitted and modules may communicate with, and share, resources of other modules. Any of the system components or modules can be realized partially or fully in the physician/patient programmer 70, remote computer 70', or neurostimulation system 50. The modules may reside within the device 50 housing or may exist externally and communicate. The apparatus 50 may be realized as a portable or desktop instrument that controls accessories. The system can be implemented, at least in part, as customized hardware that operates with a smart-phone or tablet computer or which communicates with the smartphone or computer so that some disclosed modules are realized by the smart phone or computer.

The subject systems and methods may be realized using various instruments and tissue stimulators patented and/or distributed by companies such as Cogentix, Electrocore, Cyberonics, Medtronic, Valencia Technologies, StimGuard, Halo Neuroscience, eNEURA (e.g., TMS), Bioness, and Cephaly, for providing stimulation of human tissue. This includes electrical, magnetic, microwave or other forms of energy directed either to implantable components that stimulate tissue or to the tissue itself. This can include cranial electrotherapy, transcranial stimulation (e.g., direct-current or alternating current), ultrasonic neuromodulation. Stimulation provided by at least one of TENS, eTENS, percutaneous, external, partially or fully implantable systems can be operated to provide stimulation using the protocols and nerve targets disclosed herein. Patients (including children with urinary disorders) may be treated with either TENS, percutaneous, or implanted devices as a means of reducing their OAB symptoms that include incontinence, enuresis, and nocturia, or treating various pelvic floor disorders by SAFN stimulation.

Embodiments disclosed herein for treatment of OAB are applicable to treatment of specific symptoms and disorders such as incontinence, urge related to and frequency of urination, bladder pain, fecal incontinence, sexual disorders, and pelvic floor disorders and their symptoms. Treatment can include relief from symptoms, improvement of abnormal activity, etc.

In the specification, section titles are provided for convenience only and are not meant to limit the invention. Methods disclosed herein include method steps, but these steps and the related operations may be omitted or occur in a different order during operation of the system.

The foregoing description of preferred embodiments for this disclosure have been presented for purposes of illustration and description. They are not intended to limit the invention to the precise forms disclosed. Obvious modifications or variations are possible in light of the above teachings. The different embodiments are chosen and described to provide the best illustrations of the principles of the invention and its practical application, and to thereby enable one of ordinary skill in the art to utilize the invention in various embodiments and with various modifications as are suited to the particular use contemplated. All these modifications and variations are within the scope of the invention as determined by the appended claims when interpreted in accordance with the breadth to which they are entitled.

What is claimed is:

1. A patient pelvic disorder treatment regimen compliance system for managing a pelvic disorder treatment regimen that includes the provision of neurostimulation comprising:
   at least a first processor configured for operating a control module;
   at least one neurostimulator coupled to said at least one processor and configured to communicate data or control signals to and from the at least one first processor;
   the control module configured to establish a programmable treatment regimen for the treatment of a pelvic floor disorder which includes at least operation of said neurostimulator and control of a compliance module configured for calculating and storing a measurement of compliance by the user for at least one characteristic of the programmable treatment regimen for a patient's pelvic disorder treatment having a treatment schedule with at least one set of scheduled events, the programmable treatment regimen defined for at least one neurostimulation pelvic disorder treatment provided by the at least one neurostimulator having a stimulation protocol defined to treat the pelvic disorder;
   at least one notification module coupled to the control module and configured to provide a notification signal to a user related to patient compliance for the at least one set of scheduled events provided by said programmable treatment regimen, said notification signal being responsive to at least one notification rule which defines notification to be provided to said user if said patient has not met a compliance criterion for said at least one characteristic of said programmable pelvic disorder treatment regimen;
   at least one patient interface module coupled to the control module and said notification module, said patient interface module being configured to provide compliance information to said user related to said patient compliance criteria defined for the at least one set of scheduled events of the programmable treatment regimen and,
   at least one external patient/physician device in communication with said at least one notification module, said at least one external patient/physician device configured to display compliance information provided by the patient interface module, accept user input data, and communicate data or control signals to the processor.

2. The system of claim 1, wherein said patient interface module is configured to provide compliance information and operates at least partially under control of the compliance module based upon assessment of compliance for at least one parameter defined for treatment regimen operations.

3. The system of claim 2, wherein said at least one parameter defined for treatment regimen operations includes a defined dose of stimulation to be provided within a selected time interval.

4. The system of claim 2, wherein said at least one parameter defined for treatment regimen operations includes assessment of compliance of said patient to answer a defined set of questions to be to be posed to said patient and answered within a selected time interval.

5. The system of claim 2, wherein said at least one parameter defined for treatment regimen operations includes assessment of compliance for viewing by said patient or user of a defined set of training videos to be to be viewed within a selected time interval.

6. The system of claim 2, wherein said at least one parameter defined for treatment regimen operations includes a defined set of messages about lifestyle changes to be viewed within a selected time interval.

7. The system of claim 1, wherein the measurement of compliance of at least one characteristic of a programmable treatment regimen related to the at least one neurostimulation pelvic disorder treatment defined for the at least one neurostimulator, includes determining if a compliance criterion has been met which includes a minimum stimulation dose delivered across a selected time interval.

8. The system of claim 1, wherein the measurement of compliance of at least one characteristic of a programmable treatment regimen related to neurostimulation defined for at least one neurostimulator, includes determining if a minimum number of treatment sessions lasting a minimum defined period of 30 minutes have been delivered within a selected interval.

9. The system of claim 1, wherein the measurement of compliance of at least one characteristic of a programmable treatment regimen, includes at least one of:
   a. determining if a maximum number of treatment sessions lasting a minimum defined period have been delivered within a selected interval;
   b. determining if a maximum defined dosage has been delivered within a selected interval;

c. determining if a user has alternated stimulation sites between the two sides of the body or two sites after a selected interval of stimulation, as defined by a stimulation location criterion;

d. determining if a user has replaced disposable stimulation pads within a selected interval, as defined by a replacement of disposables criterion;

e. determining if a user has scheduled a doctor visit at a clinic or virtually using a web-meeting medical assistance module within a selected interval, as defined by a check-up criterion;

f. determining if a user has performed a minimum number of defined behaviors such as user performed kegel exercises, or electrically assisted intravaginal stimulation, within a selected interval, as defined by a check-up criterion;

g. determining if a user has been compliant with respect to a medication regimen that is intended to occur over the same time period as the neurostimulation, as defined by a medication criterion;

h. determining if a user has been compliant with respect to a digital health regimen that includes being engaged at least a minimum amount using digital health tool programs, as defined by a digital health tools criterion;

i. determining if a user has been compliant with respect providing stimulation within selected intervals of scheduled treatment times, as defined by a latency criterion; and j. determining if a user has been compliant with respect providing stimulation according to a minimum number of scheduled treatments that occur at night, as defined by a therapy criterion.

10. The system of claim 1, wherein the measurement of compliance of at least one characteristic of a programmable treatment regimen related to neurostimulation defined for at least one neurostimulator, includes determining if a compliance criterion has been met for at least one stimulation session and graphically displaying a status related to whether the criterion was met or not.

11. The system of claim 1, wherein the measurement of compliance of at least one characteristic of a programmable treatment regimen related to neurostimulation defined for at least one neurostimulator, includes determining if a compliance criterion has been met relating to a treatment regimen operation occurring contingently based upon at least one of the following: according to a calendar schedule, according to the presence, absence, severity, change, or trend of patient symptoms evidenced by evaluation of a history of user input, according to both a calendar schedule and evaluation of user input data from a previous period.

12. The system of claim 11, wherein the treatment regimen operation includes receiving user input data to 1 or more questions contingently presented to a user.

13. The system of claim 1, wherein the compliance module is realized as at least one of: a module of the at least one neurostimulator, and module of the at least one patient/physician device, or as a module realized distributed across the at least one neurostimulator and external patient controller.

14. The system of claim 1 wherein the treatment regimen includes a treatment schedule that is adjusted by a compliance algorithm of the compliance module using patient or user input data concerning least one of the group of: symptom presence, absence, severity, or change reflected by a change score calculated as the amount of improvement or worsening of at least one current symptom score compared to a reference symptom score, a duration or dose of stimulation provided within defined interval, and elapsed time since last stimulation treatment.

15. The system of claim 1 wherein notification signals are provided to a user according to at least one of: a defined neurostimulation schedule, an adjustable neurostimulation schedule that is adjusted as a function of at least one of the following: elapsed time, symptom severity, neurostimulator usage.

16. The system of claim 1 wherein notification signals are provided to a user, by at least one of: a user device; a neurostimulation device; a physician computer; a smartphone device; and a physician programmer.

17. The system as recited in claim 1 wherein said external patient/physician device is further configured to provide compliance information to said user when said user provides a user action which is non-compliant with at least one characteristic of said programmable treatment regimen whereby the user is alerted to non-compliance of said at least one characteristic of said programmable treatment regimen.

18. The system as recited in claim 1, wherein compliance data is presented to a user as a calendar view and indicates days on which the user was compliant in providing a scheduled activity related to the treatment regimen.

19. The system as recited in claim 1, wherein compliance is presented to a user as summary statistics computed for being compliant with at least one type of scheduled events of the treatment protocol.

20. The system as recited in claim 1 wherein the pelvic floor disorder is at least one of: overactive bladder, a bladder disorder, nocturia, incontinence, urge incontinence, fecal incontinence.

21. The system as recited in claim 1 wherein said a programmable treatment regimen is configured for the stimulation of at least one of: the saphenous nerve and the posterior tibial nerve.

22. The system as recited in claim 1 wherein a user provides input to said external patient/physician device to adjust at least one parameter of at least one set of user scheduled events of the said programmable treatment regimen.

23. The system of claim 22 wherein at least one parameter defined for said programmable treatment regimen includes a defined dose of stimulation to be provided within a said user defined scheduled time interval.

24. The system of claim 22 wherein at least one parameter defined for said programmable treatment regimen includes a defined set of questions to be provided and answered within a said user defined scheduled time interval.

25. The system of claim 22 wherein at least one parameter defined for said programmable treatment regimen includes a defined set of training videos to be viewed within a said user defined scheduled time interval.

26. The system of claim 22 wherein at least one parameter defined for said programmable treatment regimen includes a defined set of messages about lifestyle changes to be viewed within a said user defined scheduled time interval.

27. The system of claim 22 wherein said user provided input to said external patient/physician device includes user specified dates and times to provide at least one set of user scheduled events of the said programmable treatment regimen.

* * * * *